US012692536B2

(12) United States Patent
Bharadwaj et al.

(10) Patent No.: US 12,692,536 B2
(45) **Date of Patent: *Jul. 28, 2026**

(54) SYSTEMS AND METHODS FOR PROCESSING OPTICALLY TAGGED BEADS

(71) Applicant: 10X GENOMICS, INC., Pleasanton, CA (US)

(72) Inventors: Rajiv Bharadwaj, Pleasanton, CA (US); Zachary Bent, Pleasanton, CA (US)

(73) Assignee: 10x Genomics, Inc., Pleasanton, CA (US)

( * ) Notice: Subject to any disclaimer, the term of this patent is extended or adjusted under 35 U.S.C. 154(b) by 8 days.

This patent is subject to a terminal disclaimer.

(21) Appl. No.: 18/428,058

(22) Filed: Jan. 31, 2024

(65) Prior Publication Data

US 2024/0360493 A1 Oct. 31, 2024

Related U.S. Application Data

(63) Continuation of application No. 16/814,908, filed on Mar. 10, 2020, now Pat. No. 11,920,183.

(60) Provisional application No. 62/816,692, filed on Mar. 11, 2019.

(51) Int. Cl.
| | |
|---|---|
| *C12Q 1/6806* | (2018.01) |
| *C12N 15/10* | (2006.01) |
| *C12Q 1/686* | (2018.01) |

(52) U.S. Cl.
CPC ....... *C12Q 1/6806* (2013.01); *C12N 15/1006* (2013.01); *C12Q 1/686* (2013.01); *C12Q 2531/113* (2013.01); *C12Q 2563/149* (2013.01); *C12Q 2565/629* (2013.01)

(58) Field of Classification Search
CPC ................ C12N 15/1006; C12Q 1/686; C12Q 2563/149; C12Q 2563/107
See application file for complete search history.

(56) References Cited

U.S. PATENT DOCUMENTS

| | | | |
|---|---|---|---|
| 4,124,638 | A | 11/1978 | Hansen |
| 5,185,099 | A | 2/1993 | Delpuech et al. |
| 5,270,183 | A | 12/1993 | Corbett et al. |
| 5,478,893 | A | 12/1995 | Ghosh et al. |
| 5,503,980 | A | 4/1996 | Cantor |
| 5,736,330 | A | 4/1998 | Fulton |
| 5,756,334 | A | 5/1998 | Perler et al. |
| 5,846,719 | A | 12/1998 | Brenner et al. |
| 5,900,481 | A | 5/1999 | Lough et al. |
| 5,942,609 | A | 8/1999 | Hunkapiller et al. |
| 5,994,056 | A | 11/1999 | Higuchi |
| 6,033,880 | A | 3/2000 | Haff et al. |
| 6,057,149 | A | 5/2000 | Burns et al. |
| 6,123,798 | A | 9/2000 | Gandhi et al. |
| 6,171,850 | B1 | 1/2001 | Nagle et al. |
| 6,172,218 | B1 | 1/2001 | Brenner |
| 6,176,962 | B1 | 1/2001 | Soane et al. |
| 6,306,590 | B1 | 10/2001 | Mehta et al. |
| 6,327,410 | B1 | 12/2001 | Walt et al. |
| 6,379,929 | B1 | 4/2002 | Burns et al. |
| 6,406,848 | B1 | 6/2002 | Bridgham et al. |
| 6,409,832 | B2 | 6/2002 | Weigl et al. |
| 6,492,118 | B1 | 12/2002 | Abrams et al. |
| 6,524,456 | B1 | 2/2003 | Ramsey et al. |
| 6,586,176 | B1 | 7/2003 | Trnovsky et al. |
| 6,632,655 | B1 | 10/2003 | Mehta et al. |
| 6,915,679 | B2 | 7/2005 | Chien et al. |
| 7,041,481 | B2 | 5/2006 | Anderson et al. |
| 7,115,400 | B1 | 10/2006 | Adessi et al. |
| 7,129,091 | B2 | 10/2006 | Ismagilov et al. |
| 7,268,167 | B2 | 9/2007 | Higuchi et al. |
| 7,282,370 | B2 | 10/2007 | Bridgham et al. |
| 7,294,503 | B2 | 11/2007 | Quake et al. |
| 7,323,305 | B2 | 1/2008 | Leamon et al. |
| 7,544,473 | B2 | 6/2009 | Brenner |
| 7,622,076 | B2 | 11/2009 | Davies et al. |
| 7,622,280 | B2 | 11/2009 | Holliger et al. |
| 7,645,596 | B2 | 1/2010 | Williams et al. |
| 7,708,949 | B2 | 5/2010 | Stone et al. |
| 7,772,287 | B2 | 8/2010 | Higuchi et al. |
| 7,776,927 | B2 | 8/2010 | Chu et al. |
| 7,842,457 | B2 | 11/2010 | Berka et al. |

(Continued)

FOREIGN PATENT DOCUMENTS

| | | |
|---|---|---|
| CN | 103781918 A | 5/2014 |
| CN | 105492607 A | 4/2016 |

(Continued)

OTHER PUBLICATIONS

Co-pending U.S. Appl. No. 18/959,351, inventor Schnalll-Levin; Michael, filed Nov. 25, 2024.
Co-pending U.S. Appl. No. 19/044,383, inventors Smibert; Peter et al., filed Feb. 3, 2025.
Co-pending U.S. Appl. No. 19/093,986, inventors Bloju; Octavian Marian et al., filed Mar. 28, 2025.
Co-pending U.S. Appl. No. 18/392,684, inventors Fernandes; Sunjay Jude et al., filed Dec. 21, 2023.
Co-pending U.S. Appl. No. 18/643,684, inventor Bava; Felice Alessio, filed Apr. 23, 2024.
Co-pending U.S. Appl. No. 18/743,583, inventor Nagendran; Monica, filed Jun. 14, 2024.
Co-pending U.S. Appl. No. 18/795,976, inventors Meer; Elliott et al., filed Aug. 6, 2024.

(Continued)

*Primary Examiner* — Joseph G. Dauner
(74) *Attorney, Agent, or Firm* — Saul Ewing LLP; Justin W. Crotty; Thomas Murray

(57) ABSTRACT

The present disclosure provides methods and systems for generating and processing optically tagged beads. A nucleic acid probe comprising a fluorescent tag may be hybridized to a bead to generate an optically tagged bead. The nucleic acid probe hybridized to the optically tagged bead may be detectable by one or more signals and may be substantially unreactive to one or more chemical reactions performed with, or in the presence of, the optically tagged bead.

17 Claims, 12 Drawing Sheets

Specification includes a Sequence Listing.

(56) References Cited

U.S. PATENT DOCUMENTS

| | | | |
|---|---|---|---|
| 7,910,354 | B2 | 3/2011 | Drmanac et al. |
| 7,927,797 | B2 | 4/2011 | Nobile et al. |
| 7,960,104 | B2 | 6/2011 | Drmanac et al. |
| 7,968,287 | B2 | 6/2011 | Griffiths et al. |
| 8,003,312 | B2 | 8/2011 | Krutzik et al. |
| 8,053,192 | B2 | 11/2011 | Bignell et al. |
| 8,133,719 | B2 | 3/2012 | Drmanac et al. |
| 8,168,385 | B2 | 5/2012 | Brenner |
| 8,268,564 | B2 | 9/2012 | Roth et al. |
| 8,273,573 | B2 | 9/2012 | Ismagilov et al. |
| 8,298,767 | B2 | 10/2012 | Brenner et al. |
| 8,304,193 | B2 | 11/2012 | Ismagilov et al. |
| 8,318,433 | B2 | 11/2012 | Brenner |
| 8,329,407 | B2 | 12/2012 | Ismagilov et al. |
| 8,592,150 | B2 | 11/2013 | Drmanac et al. |
| 8,658,430 | B2 | 2/2014 | Miller et al. |
| 8,822,148 | B2 | 9/2014 | Ismagilov et al. |
| 8,835,358 | B2 | 9/2014 | Fodor et al. |
| 8,871,444 | B2 | 10/2014 | Griffiths et al. |
| 8,889,083 | B2 | 11/2014 | Ismagilov et al. |
| 8,975,302 | B2 | 3/2015 | Light et al. |
| 9,012,390 | B2 | 4/2015 | Holtze et al. |
| 9,029,083 | B2 | 5/2015 | Griffiths et al. |
| 9,029,085 | B2 | 5/2015 | Agresti et al. |
| 9,085,798 | B2 | 7/2015 | Chee |
| 9,089,844 | B2 | 7/2015 | Hiddessen et al. |
| 9,126,160 | B2 | 9/2015 | Ness et al. |
| 9,156,010 | B2 | 10/2015 | Colston et al. |
| 9,194,861 | B2 | 11/2015 | Hindson et al. |
| 9,216,392 | B2 | 12/2015 | Hindson et al. |
| 9,238,206 | B2 | 1/2016 | Rotem et al. |
| 9,266,104 | B2 | 2/2016 | Link |
| 9,290,808 | B2 | 3/2016 | Fodor et al. |
| 9,328,382 | B2 | 5/2016 | Drmanac et al. |
| 9,347,059 | B2 | 5/2016 | Saxonov |
| 9,371,598 | B2 | 6/2016 | Chee |
| 9,388,465 | B2 | 7/2016 | Hindson et al. |
| 9,417,190 | B2 | 8/2016 | Hindson et al. |
| 9,486,757 | B2 | 11/2016 | Romanowsky et al. |
| 9,498,761 | B2 | 11/2016 | Holtze et al. |
| 9,500,664 | B2 | 11/2016 | Ness et al. |
| 9,567,631 | B2 | 2/2017 | Hindson et al. |
| 9,593,365 | B2 | 3/2017 | Frisen et al. |
| 9,623,384 | B2 | 4/2017 | Hindson et al. |
| 9,637,799 | B2 | 5/2017 | Fan et al. |
| 9,644,204 | B2 | 5/2017 | Hindson et al. |
| 9,689,024 | B2 | 6/2017 | Hindson et al. |
| 9,694,361 | B2 | 7/2017 | Bharadwaj et al. |
| 9,701,998 | B2 | 7/2017 | Hindson et al. |
| 9,714,897 | B2 | 7/2017 | Kim et al. |
| 9,764,322 | B2 | 9/2017 | Hiddessen et al. |
| 9,824,068 | B2 | 11/2017 | Wong |
| 9,868,979 | B2 | 1/2018 | Chee et al. |
| 9,879,313 | B2 | 1/2018 | Chee et al. |
| 9,915,598 | B2 | 3/2018 | Kim et al. |
| 9,946,577 | B1 | 4/2018 | Stafford et al. |
| 9,951,386 | B2 | 4/2018 | Hindson et al. |
| 9,957,558 | B2 | 5/2018 | Leamon et al. |
| 9,975,122 | B2 | 5/2018 | Masquelier et al. |
| 10,011,872 | B1 | 7/2018 | Belgrader et al. |
| 10,017,759 | B2 | 7/2018 | Kaper et al. |
| 10,030,261 | B2 | 7/2018 | Frisen et al. |
| 10,059,989 | B2 | 8/2018 | Giresi et al. |
| 10,221,436 | B2 | 3/2019 | Hardenbol et al. |
| 10,221,442 | B2 | 3/2019 | Hindson et al. |
| 10,253,364 | B2 | 4/2019 | Hindson et al. |
| 10,273,541 | B2 | 4/2019 | Hindson et al. |
| 10,323,279 | B2 | 6/2019 | Hindson et al. |
| 10,347,365 | B2 | 7/2019 | Wong et al. |
| 10,357,771 | B2 | 7/2019 | Bharadwaj et al. |
| 10,395,758 | B2 | 8/2019 | Schnall-Levin |
| 10,400,280 | B2 | 9/2019 | Hindson et al. |
| 10,428,326 | B2 | 10/2019 | Belhocine et al. |
| 10,481,068 | B2 | 11/2019 | Kim et al. |
| 10,533,221 | B2 | 1/2020 | Hindson et al. |
| 10,544,413 | B2 | 1/2020 | Bharadwaj et al. |
| 10,549,279 | B2 | 2/2020 | Bharadwaj et al. |
| 10,557,158 | B2 | 2/2020 | Hardenbol et al. |
| 10,590,244 | B2 | 3/2020 | Delaney et al. |
| 10,745,742 | B2 | 8/2020 | Bent et al. |
| 10,752,949 | B2 | 8/2020 | Hindson et al. |
| 10,774,374 | B2 | 9/2020 | Frisen et al. |
| 10,815,525 | B2 | 10/2020 | Lucero et al. |
| 10,829,815 | B2 | 11/2020 | Bharadwaj et al. |
| 10,837,047 | B2 | 11/2020 | Delaney et al. |
| 10,874,997 | B2 | 12/2020 | Weitz et al. |
| 10,876,147 | B2 | 12/2020 | Bent et al. |
| 10,995,333 | B2 | 5/2021 | Pfeiffer |
| 11,371,094 | B2 | 6/2022 | Ryvkin et al. |
| 11,459,607 | B1 | 10/2022 | Terry et al. |
| 11,467,153 | B2 | 10/2022 | Belhocine et al. |
| 11,655,499 | B1 | 5/2023 | Pfeiffer |
| 11,845,983 | B1 | 12/2023 | Belhocine et al. |
| 11,851,683 | B1 | 12/2023 | Maheshwari et al. |
| 11,851,700 | B1 | 12/2023 | Bava et al. |
| 11,920,183 | B2 | 3/2024 | Bharadwaj et al. |
| 11,952,626 | B2 | 4/2024 | Pfeiffer et al. |
| 12,065,688 | B2 | 8/2024 | Bell |
| 12,084,715 | B1 | 9/2024 | Lund |
| 12,163,179 | B2 | 12/2024 | Bell et al. |
| 12,169,198 | B2 | 12/2024 | Price et al. |
| 12,188,014 | B1 | 1/2025 | Price et al. |
| 12,235,262 | B1 | 2/2025 | Giresi |
| 2002/0005354 | A1 | 1/2002 | Spence et al. |
| 2002/0051971 | A1 | 5/2002 | Stuelpnagel et al. |
| 2002/0058332 | A1 | 5/2002 | Quake et al. |
| 2002/0092767 | A1 | 7/2002 | Bjornson et al. |
| 2002/0119455 | A1 | 8/2002 | Chan |
| 2002/0127736 | A1 | 9/2002 | Chou et al. |
| 2003/0036206 | A1 | 2/2003 | Chien et al. |
| 2003/0075446 | A1 | 4/2003 | Culbertson et al. |
| 2003/0124509 | A1 | 7/2003 | Kenis et al. |
| 2003/0215862 | A1 | 11/2003 | Parce et al. |
| 2004/0068019 | A1 | 4/2004 | Higuchi et al. |
| 2005/0130188 | A1 | 6/2005 | Walt et al. |
| 2005/0226129 | A1 | 10/2005 | Carr |
| 2005/0250147 | A1 | 11/2005 | Macevicz |
| 2005/0266582 | A1 | 12/2005 | Modlin et al. |
| 2005/0287572 | A1 | 12/2005 | Mathies et al. |
| 2006/0177832 | A1 | 8/2006 | Brenner |
| 2006/0275782 | A1 | 12/2006 | Gunderson et al. |
| 2007/0020640 | A1 | 1/2007 | McCloskey et al. |
| 2007/0042419 | A1 | 2/2007 | Barany et al. |
| 2007/0128656 | A1 | 6/2007 | Agrawal et al. |
| 2007/0172873 | A1 | 7/2007 | Brenner et al. |
| 2007/0190543 | A1 | 8/2007 | Livak |
| 2007/0196397 | A1 | 8/2007 | Torii et al. |
| 2007/0264320 | A1 | 11/2007 | Lee et al. |
| 2008/0056948 | A1 | 3/2008 | Dale et al. |
| 2008/0166720 | A1 | 7/2008 | Hsieh et al. |
| 2008/0242560 | A1 | 10/2008 | Gunderson et al. |
| 2009/0011943 | A1 | 1/2009 | Drmanac et al. |
| 2009/0047713 | A1 | 2/2009 | Handique |
| 2009/0099041 | A1 | 4/2009 | Church et al. |
| 2009/0131543 | A1 | 5/2009 | Weitz et al. |
| 2009/0148961 | A1 | 6/2009 | Luchini et al. |
| 2009/0155563 | A1 | 6/2009 | Petsev et al. |
| 2009/0202984 | A1 | 8/2009 | Cantor |
| 2009/0235990 | A1 | 9/2009 | Beer |
| 2009/0269248 | A1 | 10/2009 | Falb et al. |
| 2009/0286687 | A1 | 11/2009 | Dressman et al. |
| 2010/0035254 | A1 | 2/2010 | Williams |
| 2010/0069263 | A1 | 3/2010 | Shendure et al. |
| 2010/0086914 | A1 | 4/2010 | Bentley et al. |
| 2010/0105112 | A1 | 4/2010 | Holtze et al. |
| 2010/0105866 | A1 | 4/2010 | Fraden et al. |
| 2010/0184928 | A1 | 7/2010 | Kumacheva |
| 2010/0216153 | A1 | 8/2010 | Lapidus et al. |
| 2010/0248991 | A1 | 9/2010 | Roesler et al. |
| 2010/0304982 | A1 | 12/2010 | Hinz et al. |
| 2011/0143340 | A1 | 6/2011 | Fan et al. |
| 2011/0217736 | A1 | 9/2011 | Hindson |
| 2011/0305761 | A1 | 12/2011 | Shum et al. |
| 2012/0071331 | A1 | 3/2012 | Casbon et al. |

(56) References Cited

U.S. PATENT DOCUMENTS

| | | |
|---|---|---|
| 2012/0172259 A1 | 7/2012 | Rigatti et al. |
| 2012/0190032 A1 | 7/2012 | Ness et al. |
| 2012/0196288 A1 | 8/2012 | Beer |
| 2012/0219947 A1 | 8/2012 | Yurkovetsky et al. |
| 2013/0028812 A1 | 1/2013 | Prieto et al. |
| 2013/0109575 A1 | 5/2013 | Kleinschmidt et al. |
| 2013/0261196 A1 | 10/2013 | Diamond et al. |
| 2013/0302792 A1 | 11/2013 | Hindson et al. |
| 2014/0065234 A1 | 3/2014 | Shum et al. |
| 2014/0155295 A1 | 6/2014 | Hindson et al. |
| 2014/0171341 A1 | 6/2014 | Jouvenot et al. |
| 2014/0221239 A1 | 8/2014 | Carman et al. |
| 2014/0272996 A1 | 9/2014 | Bemis |
| 2014/0274740 A1 | 9/2014 | Srinivasan et al. |
| 2014/0302503 A1 | 10/2014 | Lowe et al. |
| 2014/0338753 A1 | 11/2014 | Sperling et al. |
| 2014/0378345 A1 | 12/2014 | Hindson et al. |
| 2015/0005199 A1 | 1/2015 | Hindson et al. |
| 2015/0066385 A1 | 3/2015 | Schnall-Levin et al. |
| 2015/0220532 A1 | 8/2015 | Wong |
| 2015/0267191 A1 | 9/2015 | Steelman et al. |
| 2015/0292988 A1 | 10/2015 | Bharadwaj et al. |
| 2015/0361418 A1 | 12/2015 | Reed |
| 2015/0376605 A1 | 12/2015 | Jarosz et al. |
| 2015/0376608 A1 | 12/2015 | Kaper et al. |
| 2015/0376609 A1 | 12/2015 | Hindson et al. |
| 2015/0376700 A1 | 12/2015 | Schnall-Levin et al. |
| 2015/0379196 A1 | 12/2015 | Schnall-Levin et al. |
| 2016/0008778 A1 | 1/2016 | Weitz et al. |
| 2016/0024558 A1 | 1/2016 | Hardenbol et al. |
| 2016/0024572 A1 | 1/2016 | Shishkin et al. |
| 2016/0053253 A1 | 2/2016 | Salathia et al. |
| 2016/0059204 A1 | 3/2016 | Hindson et al. |
| 2016/0060621 A1 | 3/2016 | Agresti et al. |
| 2016/0115473 A1* | 4/2016 | Kim .................. C12N 15/1068 |
| | | 506/26 |
| 2016/0122753 A1 | 5/2016 | Mikkelsen et al. |
| 2016/0122817 A1 | 5/2016 | Jarosz et al. |
| 2016/0145683 A1 | 5/2016 | Fan et al. |
| 2016/0203196 A1 | 7/2016 | Schnall-Levin et al. |
| 2016/0232291 A1 | 8/2016 | Kyriazopoulou-Panagiotopoulou et al. |
| 2016/0244809 A1 | 8/2016 | Belgrader et al. |
| 2016/0281160 A1 | 9/2016 | Jarosz et al. |
| 2016/0289769 A1 | 10/2016 | Schwartz et al. |
| 2016/0314242 A1 | 10/2016 | Schnall-Levin et al. |
| 2016/0348093 A1 | 12/2016 | Price et al. |
| 2017/0016041 A1 | 1/2017 | Greenfield et al. |
| 2017/0128937 A1 | 5/2017 | Hung et al. |
| 2017/0144161 A1 | 5/2017 | Hindson et al. |
| 2017/0145476 A1 | 5/2017 | Ryvkin et al. |
| 2017/0159109 A1 | 6/2017 | Zheng et al. |
| 2017/0235876 A1 | 8/2017 | Jaffe et al. |
| 2017/0260584 A1 | 9/2017 | Zheng et al. |
| 2018/0030515 A1 | 2/2018 | Regev et al. |
| 2018/0080075 A1 | 3/2018 | Brenner et al. |
| 2018/0105808 A1 | 4/2018 | Mikkelsen et al. |
| 2018/0216162 A1 | 8/2018 | Belhocine et al. |
| 2018/0275040 A1 | 9/2018 | Kim et al. |
| 2018/0312822 A1 | 11/2018 | Lee et al. |
| 2018/0312873 A1 | 11/2018 | Zheng |
| 2018/0340169 A1 | 11/2018 | Belhocine et al. |
| 2018/0340171 A1 | 11/2018 | Belhocine et al. |
| 2018/0371545 A1 | 12/2018 | Wong et al. |
| 2019/0060890 A1 | 2/2019 | Bharadwaj et al. |
| 2019/0060904 A1 | 2/2019 | Bharadwaj et al. |
| 2019/0060905 A1 | 2/2019 | Bharadwaj et al. |
| 2019/0064173 A1 | 2/2019 | Bharadwaj et al. |
| 2019/0071656 A1 | 3/2019 | Chang et al. |
| 2019/0085391 A1 | 3/2019 | Hindson et al. |
| 2019/0127731 A1 | 5/2019 | McDermott |
| 2019/0134633 A1 | 5/2019 | Bharadwaj et al. |
| 2019/0136316 A1 | 5/2019 | Hindson et al. |
| 2019/0153532 A1 | 5/2019 | Bharadwaj et al. |
| 2019/0176152 A1 | 6/2019 | Bharadwaj et al. |
| 2019/0177800 A1 | 6/2019 | Boutet et al. |
| 2019/0249226 A1 | 8/2019 | Bent et al. |
| 2019/0323088 A1 | 10/2019 | Boutet et al. |
| 2019/0345636 A1 | 11/2019 | McDermott et al. |
| 2019/0352717 A1 | 11/2019 | Schnall-Levin |
| 2019/0367997 A1 | 12/2019 | Bent et al. |
| 2019/0376118 A1 | 12/2019 | Belhocine et al. |
| 2020/0002763 A1 | 1/2020 | Belgrader et al. |
| 2020/0005902 A1 | 1/2020 | Mellen et al. |
| 2020/0032335 A1 | 1/2020 | Martinez |
| 2020/0033237 A1 | 1/2020 | Hindson et al. |
| 2020/0033366 A1 | 1/2020 | Alvarado Martinez |
| 2020/0056223 A1 | 2/2020 | Bell |
| 2020/0105373 A1 | 4/2020 | Zheng |
| 2020/0150020 A1 | 5/2020 | Kim et al. |
| 2020/0263232 A1 | 8/2020 | Bell et al. |
| 2020/0291454 A1 | 9/2020 | Belhocine et al. |
| 2020/0407775 A1 | 12/2020 | Bharadwaj et al. |
| 2021/0190770 A1 | 6/2021 | Delaney et al. |
| 2021/0270703 A1 | 9/2021 | Abousoud |
| 2022/0162671 A1 | 5/2022 | Pfeiffer et al. |
| 2022/0403375 A1 | 12/2022 | Alvarado Martinez |
| 2023/0167496 A1 | 6/2023 | Bava |
| 2024/0002914 A1 | 1/2024 | Pfeiffer et al. |
| 2024/0044877 A1 | 2/2024 | Price et al. |
| 2024/0272044 A1 | 8/2024 | Bava |

FOREIGN PATENT DOCUMENTS

| | | | |
|---|---|---|---|
| CN | 107208158 A | 9/2017 | |
| EP | 1019496 B1 | 9/2004 | |
| EP | 1726941 A2 | 11/2006 | |
| EP | 1841879 A2 | 10/2007 | |
| EP | 1923471 A1 | 5/2008 | |
| EP | 1967592 B1 | 4/2010 | |
| EP | 2540389 A1 | 1/2013 | |
| EP | 2635679 B1 | 4/2017 | |
| EP | 3375889 A1 | 9/2018 | |
| GB | 2097692 A | 11/1982 | |
| GB | 2097692 B | 5/1985 | |
| WO | WO-8402000 A1 | 5/1984 | |
| WO | WO-9530782 A1 | 11/1995 | |
| WO | WO-9952708 A1 | 10/1999 | |
| WO | WO-2000008212 A1 | 2/2000 | |
| WO | WO-0063437 A2 * | 10/2000 | .......... C12Q 1/6837 |
| WO | WO-2001002850 A1 | 1/2001 | |
| WO | WO-0114589 A2 | 3/2001 | |
| WO | WO-0190418 A1 | 11/2001 | |
| WO | WO-2001089787 A2 | 11/2001 | |
| WO | WO-2004002627 A2 | 1/2004 | |
| WO | WO-2004003233 A1 | 1/2004 | |
| WO | WO-2004065617 A2 | 8/2004 | |
| WO | WO-2004069849 A2 | 8/2004 | |
| WO | WO-2004091763 A2 | 10/2004 | |
| WO | WO-2005021151 A1 | 3/2005 | |
| WO | WO-2005049787 A9 | 6/2005 | |
| WO | WO-2005082098 A2 | 9/2005 | |
| WO | WO-2006040551 A2 | 4/2006 | |
| WO | WO-2006078841 A1 | 7/2006 | |
| WO | WO-2006096571 A2 | 9/2006 | |
| WO | WO-2007081385 A2 | 7/2007 | |
| WO | WO-2007081387 A1 | 7/2007 | |
| WO | WO-2007089541 A2 | 8/2007 | |
| WO | WO-2007133710 A2 | 11/2007 | |
| WO | WO-2007140015 A2 | 12/2007 | |
| WO | WO-2007147079 A2 | 12/2007 | |
| WO | WO-2008021123 A1 | 2/2008 | |
| WO | WO-2008109176 A2 | 9/2008 | |
| WO | WO-2008121342 A2 | 10/2008 | |
| WO | WO-2008134153 A1 | 11/2008 | |
| WO | WO-2008150432 A1 | 12/2008 | |
| WO | WO-2009011808 A1 | 1/2009 | |
| WO | WO-2009015296 A1 | 1/2009 | |
| WO | WO-2009085215 A1 | 7/2009 | |
| WO | WO-2009152928 A2 | 12/2009 | |
| WO | WO-2010033200 A2 | 3/2010 | |
| WO | WO-2010104604 A1 | 9/2010 | |
| WO | WO-2010117620 A2 | 10/2010 | |
| WO | WO-2010148039 A2 | 12/2010 | |

(56) References Cited

FOREIGN PATENT DOCUMENTS

| | | |
|---|---|---|
| WO | WO-2011028539 A1 | 3/2011 |
| WO | WO-2011047870 A1 | 4/2011 |
| WO | WO-2011056546 A1 | 5/2011 |
| WO | WO-2011066476 A1 | 6/2011 |
| WO | WO-2012048341 A1 | 4/2012 |
| WO | WO-2012061832 A1 | 5/2012 |
| WO | WO-2012083225 A2 | 6/2012 |
| WO | WO-2012106546 A2 | 8/2012 |
| WO | WO-2012112804 A1 | 8/2012 |
| WO | WO-2012112970 A2 | 8/2012 |
| WO | WO-2012116331 A2 | 8/2012 |
| WO | WO-2012140224 A1 | 10/2012 |
| WO | WO-2012142531 A2 | 10/2012 |
| WO | WO-2012142611 A2 | 10/2012 |
| WO | WO-2012149042 A2 | 11/2012 |
| WO | WO-2012166425 A2 | 12/2012 |
| WO | WO-2012167142 A2 | 12/2012 |
| WO | WO-2013019751 A1 | 2/2013 |
| WO | WO-2013036929 A1 | 3/2013 |
| WO | WO-2013055955 A1 | 4/2013 |
| WO | WO-2013096643 A1 | 6/2013 |
| WO | WO-2013126741 A1 | 8/2013 |
| WO | WO-2013134261 A1 | 9/2013 |
| WO | WO-2014028378 A2 | 2/2014 |
| WO | WO-2014108810 A2 | 7/2014 |
| WO | WO-2014165559 A2 | 10/2014 |
| WO | WO-2015015199 A2 | 2/2015 |
| WO | WO-2015044428 A1 | 4/2015 |
| WO | WO-2015164212 A1 | 10/2015 |
| WO | WO-2016040476 A1 | 3/2016 |
| WO | WO-2016061517 A2 | 4/2016 |
| WO | WO-2016126871 A2 | 8/2016 |
| WO | WO-2016130489 A1 | 8/2016 |
| WO | WO-2016138496 A1 | 9/2016 |
| WO | WO-2016145409 A1 | 9/2016 |
| WO | WO-2016149661 A1 | 9/2016 |
| WO | WO-2016168584 A1 | 10/2016 |
| WO | WO-2017015075 A1 | 1/2017 |
| WO | WO-2017066231 A1 | 4/2017 |
| WO | WO-2017079593 A1 | 5/2017 |
| WO | WO-2017180949 A1 | 10/2017 |
| WO | WO-2017184707 A1 | 10/2017 |
| WO | WO-2017197343 A2 | 11/2017 |
| WO | WO-2018039338 A1 | 3/2018 |
| WO | WO-2018064640 A1 | 4/2018 |
| WO | WO-2018091676 A1 | 5/2018 |
| WO | WO-2018119301 A1 | 6/2018 |
| WO | WO-2018119447 A2 | 6/2018 |
| WO | WO-2018172726 A1 | 9/2018 |
| WO | WO-2018191701 A1 | 10/2018 |
| WO | WO-2018213643 A1 | 11/2018 |
| WO | WO-2018226546 A1 | 12/2018 |
| WO | WO-2018236615 A1 | 12/2018 |
| WO | WO-2018237209 A1 | 12/2018 |
| WO | WO-2019028166 A1 | 2/2019 |
| WO | WO-2019040637 A1 | 2/2019 |
| WO | WO-2019083852 A1 | 5/2019 |
| WO | WO-2019084043 A1 | 5/2019 |
| WO | WO-2019084165 A1 | 5/2019 |
| WO | WO-2019099908 A1 | 5/2019 |
| WO | WO-2019108851 A1 | 6/2019 |
| WO | WO-2019113235 A1 | 6/2019 |
| WO | WO-2019118355 A1 | 6/2019 |
| WO | WO-2019126789 A1 | 6/2019 |
| WO | WO-2019148042 A1 | 8/2019 |
| WO | WO-2019152108 A1 | 8/2019 |
| WO | WO-2019157529 A1 | 8/2019 |
| WO | WO-2019165318 A1 | 8/2019 |
| WO | WO-2019169028 A1 | 9/2019 |
| WO | WO-2019169347 A1 | 9/2019 |
| WO | WO-2019191321 A1 | 10/2019 |
| WO | WO-2019217758 A1 | 11/2019 |
| WO | WO-2020028882 A1 | 2/2020 |
| WO | WO-2020041148 A1 | 2/2020 |
| WO | WO-2020142779 A1 | 7/2020 |
| WO | WO-2020167862 A1 | 8/2020 |
| WO | WO-2020167866 A1 | 8/2020 |
| WO | WO-2020168013 A1 | 8/2020 |
| WO | WO-2020185791 A1 | 9/2020 |
| WO | WO-2020198532 A1 | 10/2020 |
| WO | WO-2021046475 A1 | 3/2021 |
| WO | WO-2021133845 A1 | 7/2021 |
| WO | WO-2021207610 A1 | 10/2021 |
| WO | WO-2021212042 A1 | 10/2021 |
| WO | WO-2021/222302 A1 | 11/2021 |
| WO | WO-2021222301 A1 | 11/2021 |
| WO | WO-2022103712 A1 | 5/2022 |
| WO | WO-2022182682 A1 | 9/2022 |
| WO | WO-2022182785 A1 | 9/2022 |
| WO | WO-2022271908 A1 | 12/2022 |
| WO | WO-2023076528 A2 | 5/2023 |
| WO | WO-2024243444 A1 | 11/2024 |

OTHER PUBLICATIONS

Co-pending U.S. Appl. No. 18/824,258, inventor Stott; Ryan Timothy, Sep. 4, 2024.

10X Genomics, Inc. CG000153 Rev A. Chromium Single Cell DNA Reagent Kits User Guide. 2018. 62 pages.

10X Genomics, Inc. CG000184 Rev A. Chromium Single Cell 3' Reagent Kits v3 User Guide with Feature Barcoding Technology for CRISPR Screening. 2018. 70 pages.

10X Genomics, Inc. CG000185 Rev B. Chromium Single Cell 3' Reagent Kits User Guide with Feature Barcoding Technology for Cell Surface Protein. 2018. 66 pages.

10X Genomics, Inc. CG000208 Rev E. Chromium Next GEM Single Cell V(D)J reagent Kits v1.1 User Guide with Feature Barcode Technology for Cell Surface Protein. 2020. 88 pages.

10X Genomics, Inc. CG000209 Rev D. Chromium Next GEM Single Cell ATAC Reagent Kits v1.1 User Guide. 2020.

10X Genomics, Inc. CG000239 Rev B. Visium Spatial Gene Expression Reagent Kits User Guide. 2020.

10X Genomics, Inc. CG00026. Chromium Single Cell 3' Reagent Kit User Guide. 2016.

10X Genomics, Inc. LIT00003 Rev B Chromium Genome Solution Application Note. 2017.

Abate A.R et al. "Beating Poisson encapsulation statistics using close-packed ordering" Lab on a Chip (Sep. 21, 2009) 9(18):2628-2631.

Adamson et al., "Production of arrays of chemically distinct nanolitre plugs via repeated splitting in microfluidic devices", Lab Chip 6(9): 1178-1186 (Sep. 2006).

Agast, S.S. et al. "Photocleavable DNA barcode-antibody conjugates allow sensitive and multiplexed protein analysis in single cell" J Am Chem Soc (2012) 134(45):18499-18502.

Amini S. et al. "Haplotype-resolved whole-genome sequencing by contiguity-preserving transposition and combinatorial indexing" Nature Genetics (2014) 46:1343-1349 doi:10.1038/ng.3119.

Anna et al.: Formation of dispersions using "flow focusing" in microchannels: Applied Physics Letters, vol. 82, No. 3, pp. 364-366 (2003).

Baret, "Surfactants in droplet-based microfluidics" Lab Chip (12(3):422-433 (2012).

Beer et al. On-Chip, Real-Time, Single-Copy Polymerase Chain Reaction in Picoliter Droplets. Anal Chem 79:8471-8475 (2007).

Braeckmans et al., Scanning the Code. Modern Drug Discovery. 2003:28-32.

Brenner, Sydney et al. In Vitro Cloning of Complex Mixtures of DNA on Microbeads: Physical Separation of Differentially Expressed cDNAs. Proceedings of the National Academy of Sciences of the United States of America 97(4):1665-1670 (2000).

Buchman, GW et al. Selective RNA amplification: a novel method using dUMP-containing primers and uracil DNA glycosylase. PCR Methods Appl. Aug. 1993; 3(1):28-31.

Burns et al. An Integrated Nanoliter DNA Analysis Device. Science. Oct. 16, 1998;282(5388):484-7.

Burns et al. Microfabricated structures for integrated DNA analysis. Proc Natl Acad Sci U S A. May 28, 1996; 93(11): 5556-5561.

(56)         References Cited

OTHER PUBLICATIONS

Burns et al. The intensification of rapid reactions in multiphase systems using slug flow in capillaries. Lab Chip. Sep. 2001;1(1):10-15. Epub Aug. 9, 2001.

Chen et al., A Homogeneous, ligase-mediated DNA diagnostic test. Genome Res. 8(5):549-556 (1998).

Chen et al. Chemical transfection of cells in picoliter aqueous droplets in fluorocarbon oil. Anal Chem. Nov. 15, 2011;83(22):8816-20. doi: 10.1021/ac2022794. Epub Oct. 17, 2011.

Chen, Kok Hao et al. RNA Imaging. Spatially Resolved, Highly Multiplexed RNA Profiling in Single Cells. Science. vol. 348, 6233 : aaa6090, pp. 1-14 (2015).

Chien et al. "Multiport flow-control system for lab-on-a-chip microfluidic devices", Fresenius J. Anal Chem, 371:106-111 (Jul. 27, 2001).

Chu et al. Controllable monodisperse multiple emulsions. Angew Chem Int Ed Engl. 2007;46(47):8970-4.

Clausell-Tormos et al., "Droplet-based microfluidic platforms for the encapsulation and screening of mammalian cells and multicellular organisms", Chem. Biol. 15:427-437 (2008).

Co-pending U.S. Appl. No. 16/434,076, inventor Giresi; Paul, filed Jun. 6, 2019.

Co-pending U.S. Appl. No. 16/434,084, inventor Giresi; Paul, filed Jun. 6, 2019.

Co-pending U.S. Appl. No. 16/434,102, inventors Price; Andrew D. et al., filed Jun. 6, 2019.

Co-pending U.S. Appl. No. 16/737,762, inventors Price; Andrew D. et al., filed Jan. 8, 2020.

Co-pending U.S. Appl. No. 16/737,770, inventors Belhocine; Zahara Kamila et al., filed Jan. 8, 2020.

Co-pending U.S. Appl. No. 16/789,273, inventors Maheshwari; Arundhati Shamoni et al., filed Feb. 12, 2020.

Co-pending U.S. Appl. No. 17/014,909, inventor Giresi; Paul, filed Sep. 8, 2020.

Co-pending U.S. Appl. No. 17/148,942, inventors Mcdermott; Geoffrey et al., filed Jan. 14, 2021.

Co-pending U.S. Appl. No. 17/166,982, inventors Mcdermott; Geoffrey et al., filed Feb. 3, 2021.

Co-pending U.S. Appl. No. 17/175,542, inventors Maheshwari; Arundhati Shamoni et al., filed Feb. 12, 2021.

Co-pending U.S. Appl. No. 17/220,303, inventor Walter; Dagmar, filed Apr. 1, 2021.

Co-pending U.S. Appl. No. 17/381,612, inventor Martinez; Luigi Jhon Alvarado, filed Jul. 21, 2021.

Co-pending U.S. Appl. No. 17/512,241, inventors Hill; Andrew John et al., filed Oct. 27, 2021.

Co-pending U.S. Appl. No. 17/517,408, inventors Salmanzadeh; Alireza et al., filed Nov. 2, 2021.

Co-pending U.S. Appl. No. 17/518,213, inventor Lund; Paul Eugene, filed Nov. 3, 2021.

Co-pending U.S. Appl. No. 17/522,741, inventors Zheng; Xinying et al., filed Nov. 9, 2021.

Co-pending U.S. Appl. No. 17/545,862, inventor Katherine; Pfeiffer, filed Dec. 8, 2021.

Co-pending U.S. Appl. No. 17/573,350, inventor Nemec; Corey M., filed Jan. 11, 2022.

Co-pending U.S. Appl. No. 17/580,947, inventor Gibbons; Michael, filed Jan. 21, 2022.

Co-pending U.S. Appl. No. 18/046,843, inventor Toh; Mckenzi, filed Oct. 14, 2022.

Co-pending U.S. Appl. No. 18/152,650, inventor Shastry; Shankar, filed Jan. 10, 2023.

Co-pending U.S. Appl. No. 17/318,364, inventors Bava; Felice Alessio et al., filed May 12, 2021.

Damean et al. Simultaneous measurement of reactions in microdroplets filled by concentration gradients. Lab Chip. Jun. 21, 2009;9(12):1707-13. doi: 10.1039/b821021g. Epub Mar. 19, 2009.

Drmanac et al., Sequencing by hybridization (SBH): advantages, achievements, and opportunities. Adv Biochem Eng Biotechnol. 2002;77 :75-101.

Duffy et al., Rapid Protyping of Microfluidic Systems and Polydimethylsiloxane, Anal Chem 70:4974-4984 (1998).

Eastburn et al. Ultrahigh-throughput mammalian single-cell reverse-transcriptase polymerase chain reaction in microfluidic droplets. Anal Chem. Aug. 20, 2013;85(16):8016-21. doi: 10.1021/ac402057q. Epub Aug. 8, 2013.

Esser-Kahn et al. Triggered release from polymer capsules. Macromolecules. 2011; 44:5539-5553.

Gericke et al. Functional cellulose beads: preparation, characterization, and applications. Chemical reviews 113.7 (2013): 4812-4836.

Gunderson et al.: Decoding randomly ordered DNA arrays. Genome Research 14(5):870-877 (2004).

Guo et al. Droplet microfluidics for high-throughput biological assays. Lab Chip. Jun. 21, 2012;12(12):2146-55. doi: 10.1039/c2lc21147e. Epub Feb. 9, 2012.

Gyarmati et al. Reversible disulphide formation in polymer networks: a versatile functional group from synthesis to applications. European Polymer Journal. 2013; 49:1268-1286.

Hashimshony, Tamar, et al., CEL-Seq: Single-Cell RNA-Seq by Multiplexed Linear Amplification. Cell Reports 2(3):666-673 (2012).

Holtze et al. Biocompatible surfactants for water-in-fluorocarbon emulsions. Lab Chip. Oct. 2008;8(10):1632-9. doi: 10.1039/b806706f. Epub Sep. 2, 2008.

Hug et al. Measurement of the number of molecules of a single mRNA species in a complex mRNA preparation. J Theor Biol. Apr. 21, 2003;221(4):615-24.

Islam et al. Highly multiplexed and strand-specific single-cell RNA 5' end sequencing. Nat Protoc. Apr. 5, 2012;7(5):813-28. doi: 10.1038/nprot.2012.022.

Jaitin Diego Adhemar, et al., Massively Parallel single-cell RNA-seq for Marker-free Decomposition of Tissues into cell types. Science 343(6172):776-779 (2014).

Jarosz, M. et al. "Using 1ng of DNA to detect haplotype phasing and gene fusions from whole exome sequencing of cancer cell lines" Cancer Res (2015) 75(supp15):4742.

Kaper et al. Supporting Information for "Whole-genome haplotyping by dilution, amplification, and sequencing." Proc Natl Acad Sci U S A. Apr. 2, 2013;110(14):5552-7. doi: 10.1073/pnas. 1218696110. Epub Mar. 18, 2013.

Kaper et al. Whole-genome haplotyping by dilution, amplification, and sequencing. Proc Natl Acad Sci U S A. Apr. 2, 2013;110(14):5552-7. doi: 10.1073/pnas.1218696110. Epub Mar. 18, 2013.

Kenis et al. Microfabrication Inside Capillaries Using Multiphase Laminar Flow Patterning. Science. 1999; 285:83-85.

Kivioja, Teemu et al. Counting Absolute Numbers Of Molecules Using Unique Molecular Identifiers. Nature Methods 9(1):72-74 (2012).

Klein, Allon M, et al., Droplet Barcoding for Single-cell Transcriptomics Applied to Embryonic Stem Cells. Cell 161(5):1187-1201 (2015).

Korlach et al., Methods in Enzymology, Real-Time DNA Sequencing from Single Polymerase Molecules, (2010) 472:431-455.

Koster et al., "Drop-based microfluidic devices for encapsulation of single cells", Lab on a Chip The Royal Soc. of Chern. 8: 1110-1115 (2008).

Lagally et al. Single-Molecular DNA Amplification and Analysis in an Integrated Microfluidic Device. Anal Chem. Feb. 1, 2001;73(3):565-70.

Lennon et al. A scalable, fully automated process for construction of sequence-ready barcoded libraries for 454. Genome Biology 11:R15 (2010).

Macosko, Evan Z, et al., Highly Parallel Genome-wide Expression Profiling of Individual Cells Using Nanoliter Droplets. Cell 161(5):1202-1214 (2015).

Madl et al. "Bioorthogonal Strategies for Engineering Extracellular matrices", Madal, Chritopher, Adv. Funct. Master. Jan. 19, 2018, vol. 28, 1706046, pp. 1-21.

Mair et al. Injection molded microfluidic chips featuring integrated interconnects. Lab Chip. Oct. 2006;6(10):1346-54. Epub Jul. 31, 2006.

McCoy, R. et al. "Illumina TruSeq Synthetic Long-Reads Empower De Novo Assembly and Resolve Complex, Highly-Repetitive Transposable Elements" PLOS (2014) 9(9):e1016689.

(56) References Cited

OTHER PUBLICATIONS

Microfluidic ChipShop. Microfluidic product catalogue. Oct. 2009. 48 pages.

Navin, The first five years of single-cell cancer genomics and beyond. Genome Res. Oct. 2015;25(10):1499-507. doi: 10.1101/gr.191098.115.

Nisisako et al. Droplet formation in a microchannel network. Lab Chip. Feb. 2002;2(1):24-6. Epub Jan. 18, 2002.

Nisisako, T. et al. Droplet Formation in a Microchannel on PMMA Plate. Micro Total Analysis Systems. 2001. Kluwer Academic Publishers. pp. 137-138.

Nisisako, T. et al., Microfluidics large-scale integration on a chip for mass production of monodisperse droplets and particles, The Royal Society of Chemistry: Lab Chip, (Nov. 23, 2007) 8:287-293.

Novak, Richard, et al., Single-Cell Multiplex Gene Detection and Sequencing with Microfluidically Generated Agarose Emulsions. Angewandte Chemie 50(2): 390-395 (2011).

Orakdogen, N. "Novel responsive poly(N,N-dimethylaminoethyl methacrylate) gel beads: preparation, mechanical properties and pH-dependent swelling behavior" J Polym Res (2012) 19:9914.

Perrott, Jimmy. Optimization and Improvement of Emulsion PCR for the Ion Torrent Next-Generation Sequencing Platform. (2011) Thesis.

Peters, B.A. et al. Accurate whole-genome sequencing and haplotyping from 10 to 20 human cells. Nature, 487(7406):190-195 (Jul. 2012).

Plunkett et al. Chymotrypsin responsive hydrogel: application of a disulfide exchange protocol for the preparation of methacrylamide containing peptides. Biomacromolecules. Mar.-Apr. 2005;6(2):632-7.

Priest et al. Generation of Monodisperse Gel Emulsions in a Microfluidic Device, Applied Physics Letters, 88:024106 (2006).

Pushkarev et al. "Single-molecule sequencing of an individual human genome," Nature Biotech (2009) 27:847-850.

Ramsey, J.M. "The burgeoning power of the shrinking laboratory" Nature Biotech (1999) 17:1061-1062.

Ramskold et al. (2012) "Full-length mRNA-Seq from single-cell levels of RNA and individual circulating tumor cells" Nature Biotechnology 30(8):777-782.

Roche, Using Multiplex Identifier (MID) Adaptors for the GS FLX Titanium Chemistry Basic MID Set Genome Sequencer FLX System, Technical Bulletin 004-2009, (Apr. 1, 2009) pp. 1-11.

Rotem A. et al., "High-throughput single-cell labeling (Hi-SCL) for RNA-Seq using drop-based microfluidics" PLOS One (May 22, 2015) 0116328 (14 pages).

Saikia et al. Simultaneous multiplexed amplicon sequencing and transcriptome profiling in single cells. Nat Methods. Jan. 2019; 16(1):59-62. doi: 10.1038/s41592-018-0259-9. Epub Dec. 17, 2018.

Schubert et al. Microemulsifying fluorinated oils with mixtures of fluorinated and hydrogenated surfactants. Colloids and Surfaces A; Physicochemical and Engineering Aspects, 84(1994) 97-106.

Seiffert et al. Microfluidic fabrication of smart microgels from macromolecular precursors. 2010. Polymer.

Seiffert, S. et al., "Smart microgel capsules from macromolecular precursors" J. Am. Chem. Soc. (2010) 132:6606-6609.

Shah et al. "Fabrication of mono disperse thermosensitive microgels and gel capsules in micro fluidic devices", Soft Matter, 4:2303-2309 (2008).

Shendure, Jay. et al. Accurate Multiplex Polony Sequencing Of An Evolved Bacterial Genome. Science 309(5741):1728-1732 (2005).

Smith et al. Highly-multiplexed barcode sequencing: an efficient method for parallel analysis of pooled samples. Nucleic Acids Research, 38(13): e142 (2010).

Song et al. Reactions in droplets in microfluidic channels. Angew Chem Int Ed Engl. Nov. 13, 2006;45(44):7336-56.

Thaxton, C.S. et al. "A Bio-Bar-Code Assay Based Upon Dithiothreitol Oligonucleotide Release" Anal Chem (2005) 77:8174-8178.

Theberge et al. Microdroplets in microfluidics: an evolving platform for discoveries in chemistry and biology. Angew Chem Int Ed Engl. Aug. 9, 2010;49(34):5846-68. doi: 10.1002/anie.200906653.

Thorsen et al. Dynamic pattern formation in a vesicle-generating microfluidic device. Physical Review Letters. American Physical Society. 2001; 86(18):4163-4166.

Tonelli et al. Perfluoropolyether functional oligomers: unusual reactivity in organic chemistry. Journal of fluorine chemistry. 2002; 118(1)"107-121.

Turchinovich et al. "Capture and Amplification by Tailing and Switching (CATS): An Ultrasensitive Ligation-Independent Method for Generation of DNA Libraries for Deep Sequencing from Picogram Amounts of DNA and RNA." RNA Biology 11.7 (2014): 817-828. PMC. Web. Nov. 13, 2017.

U.S. Appl. No. 16/800,450, inventor Katherine; Pfeiffer, filed Feb. 25, 2020.

Uttamapinant, et al. Fast, cell-compatible click chemistry with copper-chelating azides for biomolecular labeling. Angew. Chem. Int. End. Engl., Jun. 11, 2012: 51(24) pp. 5852-5856.

Wagner, et al. Biocompatible fluorinated polyglycerols for droplet microfluidics as an alternative to PEG-based copolymer surfactants. Lab Chip. Jan. 7, 2016;16(1):65-9. doi: 10.1039/c5lc00823a. Epub Dec. 2, 2015.

Weigl et al. Microfluidic Diffusion-Based Separation and Detection. Science. 1999; pp. 346-347.

Williams et al. Amplification of complex gene libraries by emulsion PCR. Nature Methods. 3(7):545-50 (2006).

Zhang et al. One-step fabrication of supramolecular microcapsules from microfluidic droplets. Science. Feb. 10, 2012;335(6069):690-4. doi: 10.1126/science.1215416.

Zheng et al. Massively parallel digital transcriptional profiling of single cells. Nat Commun. Jan. 16, 2017;8:14049. doi: 10.1038/ncomms14049.

Zheng, X.Y. et al. "Haplotyping germline and cancer genomes with high-throughput linked-read sequencing" Nature Biotech (Feb. 1, 2016) 34(3):303-311.

Zhu et al., Reverse transcriptase template switching: a SMART approach for full-length cDNA library construction. Biotechniques 30(4):892-7 (2001).

* cited by examiner

400

SEQUENCE LISTING

```
Sequence total quantity: 1
SEQ ID NO: 1              moltype = DNA   length = 15
FEATURE                  Location/Qualifiers
source                   1..15
                         mol_type = other DNA
                         organism = synthetic construct
SEQUENCE: 1
aagagcgtcg tgtag                                              15
```

SYSTEMS AND METHODS FOR PROCESSING OPTICALLY TAGGED BEADS

CROSS-REFERENCE

This application is a continuation of U.S. patent application Ser. No. 16/814,908, filed Mar. 10, 2020, now issued as U.S. Pat. No. 11,920,183, which claims the benefit of U.S. Provisional Patent Application No. 62/816,692, filed Mar. 11, 2019, each of which is entirely incorporated herein by reference.

REFERENCE TO SEQUENCE LISTING

This application contains a Sequence Listing which has been submitted electronically in XML format and is hereby incorporated by reference in its entirety. The XML copy, created on Oct. 3, 2025, is named 394320-1018US2_sequence_listing.xml and is 1,946 bytes in size.

BACKGROUND

A sample may be processed for various purposes, such as detection, quantitation, identification, and/or characterization of a type of moiety within the sample. The sample may be a biological sample. Biological samples may be processed, such as for detection of a disease (e.g., cancer) or identification of a particular species. There are various approaches for processing samples, such as polymerase chain reaction (PCR) and sequencing.

Biological samples may be processed within various reaction environments, such as partitions. Partitions may be wells or droplets. Droplets or wells may be employed to process biological samples in a manner that enables the biological samples to be partitioned and processed separately. For example, such droplets may be fluidically isolated from other droplets, enabling accurate control of respective environments in the droplets.

Biological samples in partitions may be subjected to various processes, such as chemical processes or physical processes. Samples in partitions may be subjected to heating or cooling, or chemical reactions, such as to yield species that may be qualitatively or quantitatively processed.

SUMMARY

Biological samples may be co-partitioned with barcode carrying beads to allow attribution of barcodes to the biological samples, or constituents thereof (e.g., macromolecular constituents), such as cells and nucleic acid molecules (e.g., messenger ribonucleic acid (mRNA)), and provide identification to the biological samples for later analysis. Such analysis may involve sequencing, such as next generation sequencing. During sample preparation for downstream analysis, it may be beneficial to characterize various input or intermediary materials and reagents, such as beads, partitions (e.g., droplets), bead-containing partitions, and the biological samples. For more direct characterization, the beads can be optically tagged to provide signals that may be analyzed to determine certain parameters including, for example, concentration of primers, size of beads, cell occupancy, and bead occupancy, among other parameters. These parameters may provide data independent of downstream chemical reactions. Such characterization may provide sequencing-orthogonal data and can be useful for various applications, such as quality control purposes during product development, or optimization of process flows. Hence, there is a need to develop methods and systems for processing the bead for direct characterization.

The present disclosure provides methods and systems for generating and processing optically tagged beads. The optically tagged beads can be generated without chemically modifying, or without substantial modification to, the beads. A nucleic acid probe comprising a fluorescent tag may be hybridized to a bead to generate an optically tagged bead. The nucleic acid probe hybridized to the optically tagged bead may be detectable by one or more signals (e.g., fluorescent signals) and may be substantially unreactive to one or more chemical reactions performed with, or in the presence of, the optically tagged bead.

In an aspect, provided is a method for processing a bead, comprising: (a) hybridizing a bead and a modified probe to generate an optically tagged bead, wherein the bead comprises a binding sequence, wherein the modified probe hybridizes to the binding sequence, wherein the modified probe comprises a fluorescent tag, and wherein the modified probe hybridized to the bead is substantially unreactive to one or more chemical reactions; (b) detecting one or more signals indicative of the fluorescent tag from the optically tagged bead; and (c) conducting a chemical reaction of the one or more chemical reactions with, or in a presence of, the optically tagged bead.

In some embodiments, the method comprises, prior to hybridizing, subjecting a nucleic acid probe comprising the fluorescent tag under conditions sufficient to modify the nucleic acid probe to yield the modified probe.

In some embodiments, the nucleic acid probe comprises the fluorescent tag at a 5' end.

In some embodiments, the conditions comprise adding a 3' chain-terminating modification to the nucleic acid probe.

In some embodiments, the conditions comprise adding a fluorophore to a 3' end of the nucleic acid probe, wherein the fluorophore is in addition to the fluorescent tag.

In some embodiments, the conditions comprise adding a 3 carbon spacer to a 3' end of the nucleic acid probe. In some embodiments, the conditions comprise adding a 6 carbon spacer to a 3' end of the nucleic acid probe. In some embodiments, the conditions comprise adding a 9 carbon spacer to a 3' end of the nucleic acid probe. In some embodiments, the conditions comprise adding a 18 carbon spacer to a 3' end of the nucleic acid probe.

In some embodiments, the conditions comprise adding a biotin molecule to a 3' end of the nucleic acid probe.

In some embodiments, the nucleic acid probe comprises a probe sequence configured to hybridize to the binding sequence. In some embodiments, the modified probe comprises the probe sequence.

In some embodiments, the conditions comprise inverting a terminal base at a 3' end of the probe sequence.

In some embodiments, the conditions comprise modifying the probe sequence to destabilize hybridization between the bead and the modified probe.

In some embodiments, the hybridization comprises a mismatched base pair. In some embodiments, the hybridization comprises two mismatched base pairs.

In some embodiments, the modified probe comprises unlocked nucleic acid.

In some embodiments, the modified probe comprises the fluorescent tag at a 5' end.

In some embodiments, the detecting is performed prior to conducting the one or more chemical reactions. In some embodiments, the detecting is performed subsequent to conducting the one or more chemical reactions.

In some embodiments, the bead is a gel bead.

In some embodiments, the bead comprises a plurality of barcode molecules. In some embodiments, the plurality of barcode molecules comprise the binding sequence. In some embodiments, the bead comprises a molecule comprising the binding sequence separate from the plurality of barcode molecules.

In some embodiments, the method further comprises determining a parameter of the bead based on the one or more signals. In some embodiments, the bead comprises a plurality of primers and wherein the parameter is a concentration of the plurality of primers on the bead, wherein the modified probe comprises a probe sequence configured to hybridize to a sequence common to the plurality of primers. In some embodiments, the parameter is a size of the bead.

In some embodiments, the method further comprises, subsequent to the hybridizing, partitioning the optically tagged bead in a partition. In some embodiments, the partition is a droplet. In some embodiments, the partition is a well.

In some embodiments, the method further comprises determining a parameter of the partition or contents thereof based on the one or more signals. In some embodiments, the parameter is a cell occupancy of the partition. In some embodiments, the parameter is a bead occupancy of the partition. In some embodiments, the parameter is a concentration of a reagent in the partition. In some embodiments, the parameter is a size of the partition. In some embodiments, the partition comprises a cell, and the parameter is a cell phenotype.

In some embodiments, the method further comprises, subsequent to the hybridizing, co-partitioning the optically tagged bead and a biological analyte. In some embodiments, the method further comprises, subsequent to the hybridizing, co-partitioning the optically tagged bead and a cell bead.

In some embodiments, the method further comprises, prior to the hybridizing, generating the modified probe. In some embodiments, the generating comprises selecting the fluorescent tag from a plurality of fluorophores.

In some embodiments, the modified probe is hybridized to a selected region of the bead, wherein the selected region comprises the binding sequence. In some embodiments, the method further comprises, prior to the hybridizing, selecting the selected region.

In some embodiments, a plurality of modified probes, including the modified probe, is hybridized to the selected region of the bead, wherein the selected region comprises a plurality of binding sequences, including the binding sequence, configured to hybridize to the plurality of modified probes.

In some embodiments, the hybridizing comprises hybridizing a plurality of modified probes, including the modified probe, to the optically tagged bead, wherein the plurality of modified probes comprises a plurality of fluorescent tags, including the fluorescent tag. In some embodiments, the method further comprises, prior to the hybridizing, selecting the plurality of fluorescent tags.

In some embodiments, the plurality of modified probes are hybridized to one or more selected regions of the bead. In some embodiments, the method further comprises, prior to the hybridizing, selecting the one or more selected regions. In some embodiments, the method further comprises, prior to the hybridizing, selecting a density or concentration, or ranges thereof, of modified probes hybridized to the one or more selected regions.

In another aspect, provided is a kit, comprising: a plurality of modified probes configured to hybridize to a bead comprising a binding sequence, wherein a modified probe of the plurality of modified probes comprises a fluorescent tag, wherein the modified probe is configured to hybridize to the binding sequence, and wherein the modified probe, when hybridized to the binding sequence, is substantially unreactive to one or more chemical reactions conducted with, or in a presence of, the bead hybridized to the modified probe.

In some embodiments, the method further comprises the bead.

In some embodiments, a fluorescent signal from the fluorescent tag is detectable prior to the one or more chemical reactions. In some embodiments, a fluorescent signal from the fluorescent tag is detectable subsequent to the one or more chemical reactions.

In some embodiments, the modified probe comprises the fluorescent tag at a 5' end.

In another aspect, provided is a kit, comprising: a plurality of nucleic acid probes configured to hybridize to a bead, wherein the plurality of nucleic acid probes, when hybridized to the bead, are substantially reactive to one or more chemical reactions conducted with, or in a presence of, the bead hybridized to the plurality of nucleic acid probes; a plurality of fluorophores; and reagents for modifying the plurality of nucleic acid probes to generate a plurality of modified probes, wherein the plurality of modified probes are (i) configured to hybridize to the bead, (ii) comprises the plurality of fluorophores, and (iii) when hybridized to the bead, are substantially unreactive to one or more chemical reactions conducted with, or in a presence of, the bead hybridized to the plurality of modified probes.

In some embodiments, the kit further comprises the bead.

In some embodiments, a fluorescent signal from the plurality of fluorophores is detectable prior to the one or more chemical reactions. In some embodiments, a fluorescent signal from the plurality of fluorophores is detectable subsequent to the one or more chemical reactions.

In some embodiments, the plurality of nucleic acid probes comprises the plurality of fluorophores. In some embodiments, the plurality of nucleic acid probes comprises the plurality of fluorophores at a 5' end.

In some embodiments, the plurality of modified probes comprises the plurality of fluorophores at a 5' end.

In some embodiments, the reagents comprise reagents configured to add a 3' chain-terminating modification to the plurality of nucleic acid probes.

In some embodiments, the reagents comprise reagents configured to add a fluorophore to a 5' end of the plurality of nucleic acid probes. In some embodiments, the reagents comprise reagents configured to add a fluorophore to a 3' end of the plurality of nucleic acid probes.

In some embodiments, the reagents comprise reagents configured to add a 3' chain-terminating modification to the plurality of nucleic acid probes, wherein the plurality of nucleic acid probes comprises the plurality of fluorophores at a 5' end.

In some embodiments, the reagents comprise reagents configured to add a 3 carbon spacer to a 3' end of the plurality of nucleic acid probes. In some embodiments, the reagents comprise reagents configured to add a 6 carbon spacer to a 3' end of the plurality of nucleic acid probes. In some embodiments, the reagents comprise reagents configured to add a 9 carbon spacer to a 3' end of the plurality of nucleic acid probes. In some embodiments, the reagents comprise reagents configured to add a 18 carbon spacer to a 3' end of the plurality of nucleic acid probes.

In some embodiments, wherein the reagents comprise reagents configured to add a biotin molecule to a 3' end of the plurality of nucleic acid probes.

In some embodiments, the reagents comprise reagents configured to invert a terminal base at a 3' end of the plurality of nucleic acid probes.

In some embodiments, the plurality of modified probes comprises a probe sequence configured to hybridize to a binding sequence of a bead. In some embodiments, the probe sequence and the binding sequence comprises a mismatched base pair. In some embodiments, the probe sequence and the binding sequence comprises two mismatched base pairs.

In some embodiments, the modified probes comprise unlocked nucleic acid.

Another aspect of the present disclosure provides a non-transitory computer readable medium comprising machine executable code that, upon execution by one or more computer processors, implements any of the methods above or elsewhere herein.

In an aspect, the present disclosure provides a method for processing a bead. The method may comprise hybridizing a bead and a first nucleic acid probe to generate an optically tagged bead, wherein the bead may comprise a first binding sequence, and the first nucleic acid probe may hybridize to the first binding sequence, and the first nucleic acid probe may comprise a first fluorescent tag. The method may further comprise detecting one or more signals indicative of the first fluorescent tag from the optically tagged bead; and using the one or more signals to determine the presence of the first binding sequence on the bead.

In some embodiments, the method may further comprise, hybridizing the bead with a second nucleic acid probe before detecting the one or more signals indicative of the first fluorescent tag from the optically tagged bead. The bead may comprise a second binding sequence which may be different than the first binding sequence, and the second nucleic acid probe may hybridize to the second binding sequence, and the second nucleic acid probe may comprise a second fluorescent tag which may be different than the first fluorescent tag. In some embodiments, the method further comprises detecting one or more additional signals indicative of the second fluorescent tag from the optically tagged bead and using the one or more additional signals to determine the presence of the second binding sequence on the bead.

In some embodiments, the detecting of said one or more signals comprises using a flow cytometer, a fluorescence-activated cell sorting (FACS) instrument, or a combination thereof.

In some embodiments, the method further comprises processing each bead of a population of beads through (a)-(c), and subsequent to (c), using the one or more signals from each bead of the population of beads to determine a quality of the population of beads. In some embodiments, the quality of population of beads comprises a loading efficiency of the binding sequence to the population of beads, an efficiency of hybridization of the modified probe or the first nucleic acid probe to the binding sequence, homogeneity or bead-to-bead variability of the population of beads, or combinations thereof. In some embodiments, the homogeneity or bead-to-bead variability may be quantified or characterized by a coefficient of variance of the one or more signals detected for the population of beads.

Another aspect of the present disclosure provides a system comprising one or more computer processors and computer memory coupled thereto. The computer memory comprises machine executable code that, upon execution by the one or more computer processors, implements any of the methods above or elsewhere herein.

Additional aspects and advantages of the present disclosure will become readily apparent to those skilled in this art from the following detailed description, wherein only illustrative embodiments of the present disclosure are shown and described. As will be realized, the present disclosure is capable of other and different embodiments, and its several details are capable of modifications in various obvious respects, all without departing from the disclosure. Accordingly, the drawings and description are to be regarded as illustrative in nature, and not as restrictive.

INCORPORATION BY REFERENCE

All publications, patents, and patent applications mentioned in this specification are herein incorporated by reference to the same extent as if each individual publication, patent, or patent application was specifically and individually indicated to be incorporated by reference. To the extent publications and patents or patent applications incorporated by reference contradict the disclosure contained in the specification, the specification is intended to supersede and/or take precedence over any such contradictory material.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings (also "Figure" and "FIG." herein), of which:

DETAILED DESCRIPTION

Figure 1:
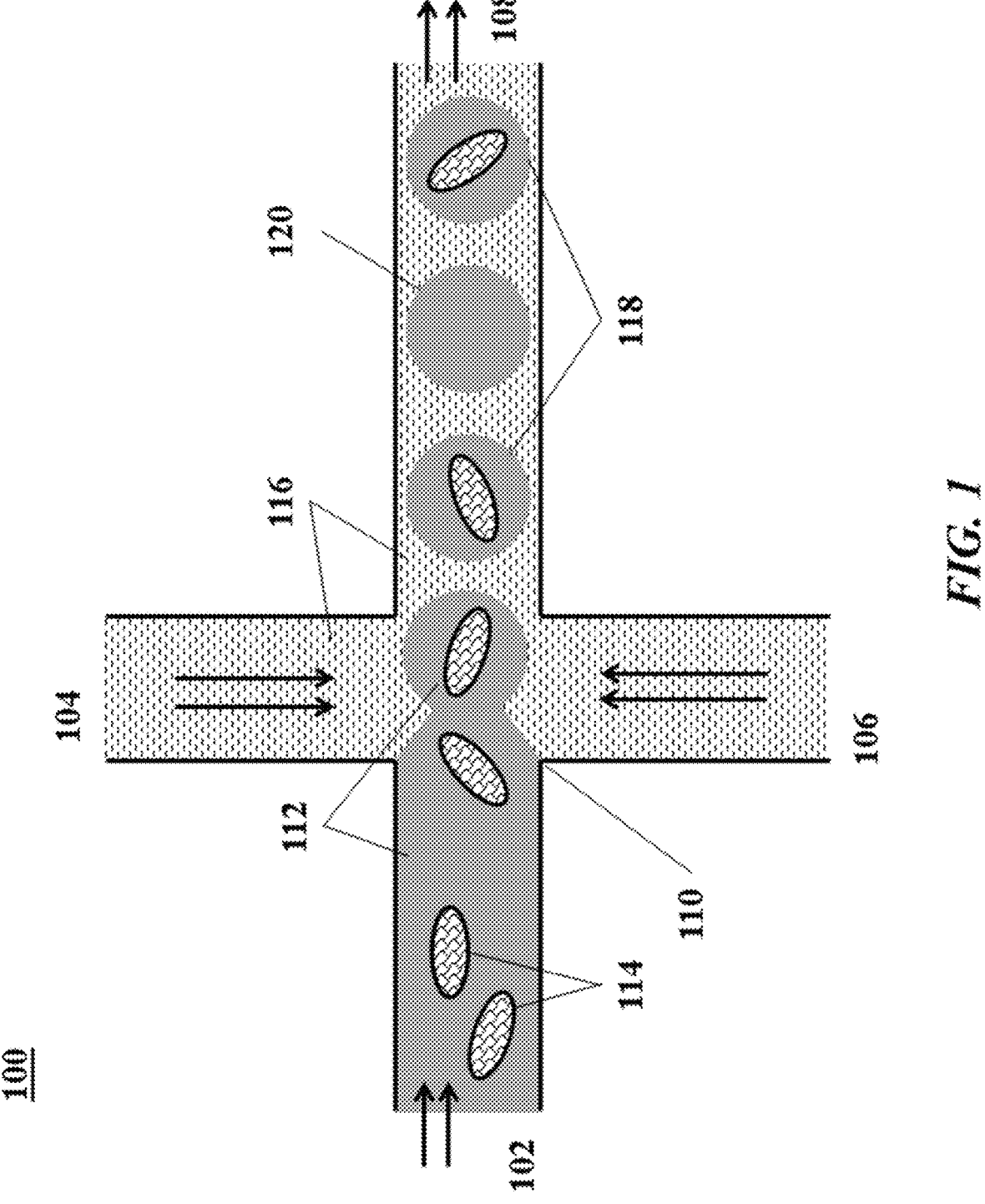
FIG. 1 shows an example of a microfluidic channel structure for partitioning individual biological particles.

While various embodiments of the invention have been shown and described herein, it will be obvious to those skilled in the art that such embodiments are provided by way of example only. Numerous variations, changes, and substitutions may occur to those skilled in the art without departing from the invention. It should be understood that various alternatives to the embodiments of the invention described herein may be employed.

Where values are described as ranges, it will be understood that such disclosure includes the disclosure of all possible sub-ranges within such ranges, as well as specific numerical values that fall within such ranges irrespective of whether a specific numerical value or specific sub-range is expressly stated.

The term "barcode," as used herein, generally refers to a label, or identifier, that conveys or is capable of conveying information about an analyte. A barcode can be part of an analyte. A barcode can be independent of an analyte. A barcode can be a tag attached to an analyte (e.g., nucleic acid molecule) or a combination of the tag in addition to an endogenous characteristic of the analyte (e.g., size of the analyte or end sequence(s)). A barcode may be unique. Barcodes can have a variety of different formats. For example, barcodes can include: polynucleotide barcodes; random nucleic acid and/or amino acid sequences; and synthetic nucleic acid and/or amino acid sequences. A barcode can be attached to an analyte in a reversible or irreversible manner. A barcode can be added to, for example, a fragment of a deoxyribonucleic acid (DNA) or ribonucleic acid (RNA) sample before, during, and/or after sequencing of the sample. Barcodes can allow for identification and/or quantification of individual sequencing-reads.

The term "real time," as used herein, can refer to a response time of less than about 1 second, a tenth of a second, a hundredth of a second, a millisecond, or less. The response time may be greater than 1 second. In some instances, real time can refer to simultaneous or substantially simultaneous processing, detection or identification.

The term "subject," as used herein, generally refers to an animal, such as a mammal (e.g., human) or avian (e.g., bird), or other organism, such as a plant. For example, the subject can be a vertebrate, a mammal, a rodent (e.g., a mouse), a primate, a simian or a human. Animals may include, but are not limited to, farm animals, sport animals, and pets. A subject can be a healthy or asymptomatic individual, an individual that has or is suspected of having a disease (e.g., cancer) or a pre-disposition to the disease, and/or an individual that is in need of therapy or suspected of needing therapy. A subject can be a patient. A subject can be a microorganism or microbe (e.g., bacteria, fungi, archaea, viruses).

The term "genome," as used herein, generally refers to genomic information from a subject, which may be, for example, at least a portion or an entirety of a subject's hereditary information. A genome can be encoded either in DNA or in RNA. A genome can comprise coding regions (e.g., that code for proteins) as well as non-coding regions. A genome can include the sequence of all chromosomes together in an organism. For example, the human genome ordinarily has a total of 46 chromosomes. The sequence of all of these together may constitute a human genome.

The terms "adaptor(s)", "adapter(s)" and "tag(s)" may be used synonymously. An adaptor or tag can be coupled to a polynucleotide sequence to be "tagged" by any approach, including ligation, hybridization, or other approaches.

The term "sequencing," as used herein, generally refers to methods and technologies for determining the sequence of nucleotide bases in one or more polynucleotides. The polynucleotides can be, for example, nucleic acid molecules such as deoxyribonucleic acid (DNA) or ribonucleic acid (RNA), including variants or derivatives thereof (e.g., single stranded DNA). Sequencing can be performed by various systems currently available, such as, without limitation, a sequencing system by Illumina®, Pacific Biosciences (PacBio®), Oxford Nanopore®, or Life Technologies (Ion Torrent®). Alternatively or in addition, sequencing may be performed using nucleic acid amplification, polymerase chain reaction (PCR) (e.g., digital PCR, quantitative PCR, or real time PCR), or isothermal amplification. Such systems may provide a plurality of raw genetic data corresponding to the genetic information of a subject (e.g., human), as generated by the systems from a sample provided by the subject. In some examples, such systems provide sequencing reads (also "reads" herein). A read may include a string of nucleic acid bases corresponding to a sequence of a nucleic acid molecule that has been sequenced. In some situations, systems and methods provided herein may be used with proteomic information.

The terms "a," "an," and "the," as used herein, generally refers to singular and plural references unless the context clearly dictates otherwise.

Whenever the term "at least," "greater than," or "greater than or equal to" precedes the first numerical value in a series of two or more numerical values, the term "at least," "greater than" or "greater than or equal to" applies to each of the numerical values in that series of numerical values. For example, greater than or equal to 1, 2, or 3 is equivalent to greater than or equal to 1, greater than or equal to 2, or greater than or equal to 3.

Whenever the term "no more than," "less than," or "less than or equal to" precedes the first numerical value in a series of two or more numerical values, the term "no more than," "less than," or "less than or equal to" applies to each of the numerical values in that series of numerical values. For example, less than or equal to 3, 2, or 1 is equivalent to less than or equal to 3, less than or equal to 2, or less than or equal to 1.

The term "bead," as used herein, generally refers to a particle. The bead may be a solid or semi-solid particle. The bead may be a gel bead. The gel bead may include a polymer matrix (e.g., matrix formed by polymerization or cross-linking). The polymer matrix may include one or more polymers (e.g., polymers having different functional groups or repeat units). Polymers in the polymer matrix may be randomly arranged, such as in random copolymers, and/or have ordered structures, such as in block copolymers. Cross-linking can be via covalent, ionic, or inductive, interactions, or physical entanglement. The bead may be a macromolecule. The bead may be formed of nucleic acid molecules bound together. The bead may be formed via covalent or non-covalent assembly of molecules (e.g., macromolecules), such as monomers or polymers. Such polymers or monomers may be natural or synthetic. Such polymers or monomers may be or include, for example, nucleic acid molecules (e.g., DNA or RNA). The bead may be formed of a polymeric material. The bead may be magnetic or non-magnetic. The bead may be rigid. The bead may be flexible and/or compressible. The bead may be disruptable or dissolvable. The bead may be a solid particle (e.g., a metal-based particle including but not limited to iron oxide, gold or silver) covered with a coating comprising one or more polymers. Such coating may be disruptable or dissolvable.

The term "sample," as used herein, generally refers to a biological sample of a subject. The biological sample may comprise any number of macromolecules, for example, cellular macromolecules. The sample may be a cell sample. The sample may be a cell line or cell culture sample. The sample can include one or more cells. The sample can include one or more microbes. The biological sample may be a nucleic acid sample or protein sample. The biological sample may also be a carbohydrate sample or a lipid sample. The biological sample may be derived from another sample. The sample may be a tissue sample, such as a biopsy, core biopsy, needle aspirate, or fine needle aspirate. The sample may be a fluid sample, such as a blood sample, urine sample, or saliva sample. The sample may be a skin sample. The sample may be a cheek swab. The sample may be a plasma or serum sample. The sample may be a cell-free or cell free sample. A cell-free sample may include extracellular polynucleotides. Extracellular polynucleotides may be isolated from a bodily sample that may be selected from the group consisting of blood, plasma, serum, urine, saliva, mucosal excretions, sputum, stool and tears.

The term "biological particle," as used herein, generally refers to a discrete biological system derived from a biological sample. The biological particle may be a macromolecule. The biological particle may be a small molecule. The biological particle may be a virus. The biological particle may be a cell or derivative of a cell. The biological particle may be an organelle. The biological particle may be a rare cell from a population of cells. The biological particle may be any type of cell, including without limitation prokaryotic cells, eukaryotic cells, bacterial, fungal, plant, mammalian, or other animal cell type, mycoplasmas, normal tissue cells, tumor cells, or any other cell type, whether derived from single cell or multicellular organisms. The biological particle may be a constituent of a cell. The biological particle may be or may include DNA, RNA, organelles, proteins, or any combination thereof. The biological particle may be or may include a matrix (e.g., a gel or polymer matrix) comprising a cell or one or more constituents from a cell (e.g., cell bead), such as DNA, RNA, organelles, proteins, or any combination thereof, from the cell. The biological particle may be obtained from a tissue of a subject. The biological particle may be a hardened cell. Such hardened cell may or may not include a cell wall or cell membrane. The biological particle may include one or more constituents of a cell, but may not include other constituents of the cell. An example of such constituents is a nucleus or an organelle. A cell may be a live cell. The live cell may be capable of being cultured, for example, being cultured when enclosed in a gel or polymer matrix, or cultured when comprising a gel or polymer matrix.

The term "macromolecular constituent," as used herein, generally refers to a macromolecule contained within or from a biological particle. The macromolecular constituent may comprise a nucleic acid. In some cases, the biological particle may be a macromolecule. The macromolecular constituent may comprise DNA. The macromolecular constituent may comprise RNA. The RNA may be coding or non-coding. The RNA may be messenger RNA (mRNA), ribosomal RNA (rRNA) or transfer RNA (tRNA), for example. The RNA may be a transcript. The RNA may be small RNA that are less than 200 nucleic acid bases in length, or large RNA that are greater than 200 nucleic acid bases in length. Small RNAs may include 5.8S ribosomal RNA (rRNA), 5S rRNA, transfer RNA (tRNA), microRNA (miRNA), small interfering RNA (siRNA), small nucleolar RNA (snoRNAs), Piwi-interacting RNA (piRNA), tRNA-derived small RNA (tsRNA) and small rDNA-derived RNA (srRNA). The RNA may be double-stranded RNA or single-stranded RNA. The RNA may be circular RNA. The macromolecular constituent may comprise a protein. The macromolecular constituent may comprise a peptide. The macromolecular constituent may comprise a polypeptide.

The term "molecular tag," as used herein, generally refers to a molecule capable of binding to a macromolecular constituent. The molecular tag may bind to the macromolecular constituent with high affinity. The molecular tag may bind to the macromolecular constituent with high specificity. The molecular tag may comprise a nucleotide sequence. The molecular tag may comprise a nucleic acid sequence. The nucleic acid sequence may be at least a portion or an entirety of the molecular tag. The molecular tag may be a nucleic acid molecule or may be part of a nucleic acid molecule. The molecular tag may be an oligonucleotide or a polypeptide. The molecular tag may comprise a DNA aptamer. The molecular tag may be or comprise a primer. The molecular tag may be, or comprise, a protein. The molecular tag may comprise a polypeptide. The molecular tag may be a barcode.

The term "partition," as used herein, generally, refers to a space or volume that may be suitable to contain one or more species or conduct one or more reactions. A partition may be a physical compartment, such as a droplet or well. The partition may isolate space or volume from another space or volume. The droplet may be a first phase (e.g., aqueous phase) in a second phase (e.g., oil) immiscible with the first phase. The droplet may be a first phase in a second phase that does not phase separate from the first phase, such as, for example, a capsule or liposome in an aqueous phase. A partition may comprise one or more other (inner) partitions. In some cases, a partition may be a virtual compartment that can be defined and identified by an index (e.g., indexed libraries) across multiple and/or remote physical compartments. For example, a physical compartment may comprise a plurality of virtual compartments.

Provided herein are methods and systems for preparing and processing optically tagged beads. The optically tagged beads may comprise one or more fluorescent tags. A nucleic acid probe comprising a fluorescent tag may be hybridized to a bead to generate an optically tagged bead. The nucleic acid probe hybridized to the optically tagged bead may be detectable by one or more signals and may be substantially unreactive to one or more chemical reactions performed with, or in the presence of, the optically tagged bead.

Optically Tagged Beads

The optically tagged beads disclosed herein may allow for rapid and direct characterization of beads, biological particles, and partitions (e.g., partitions encapsulating one or more beads and/or biological particles).

Provided herein are methods for processing a bead. The methods can comprise hybridizing the bead and a modified probe to generate an optically tagged bead, wherein the modified probe comprises a fluorescent tag. The bead can comprise a binding sequence, and the modified probe can hybridize to the binding sequence. The modified probe hybridized to the bead can be substantially unreactive to one or more chemical reactions.

The methods can further comprise detecting one or more signals indicative of the fluorescent tag from the optically tagged bead. The detection can comprise using an instrument. The instrument can be an optical instrument. In some examples, the instrument comprises a flow cytometer. Instrument may comprise a fluorescence-activated cell sorting (FACS) instrument. In other examples, detection may comprise using any system, device or instrument such as a microscope, a plate reader, a cell sorting device, microfluidic device, other devices or instruments, or any combination of the mentioned devices. In some cases, the method may comprise sorting the cells on a coverslip or in a device before detection. The methods may further comprise conducting a chemical reaction of the one or more chemical reactions with, or in a presence of, the optically tagged bead.

In some instances, the methods can further comprise, prior to hybridizing the modified probe and the bead, subjecting a nucleic acid probe comprising the fluorescent tag under conditions sufficient to modify the nucleic acid probe to yield the modified probe.

In some examples, the method may comprise processing a population of beads, such as each bead of a population of beads. The method may comprise detecting one or more signals for each bead of the population of beads. The detected signals may be subsequently used to analyze or assess a parameter or quality of the population of beads and/or a homogeneity, heterogeneity, or bead-to-bead variation of the population of beads. In some cases, the mean value, median, standard deviation, coefficient of variance, and/or other metrics may be calculated for the detected signals and be used to characterize the population of beads. Such qualities may comprise, for example, the loading efficiency of the binding sequence to the population of beads, the efficiency of hybridization of the modified probe or the first nucleic acid probe (or a fluorophore or fluorescent tag) to the binding sequence. Such qualities may comprise primer loading efficiency and ligation efficiency. In some cases, the population homogeneity, heterogeneity, or bead-to-bead variability may be characterized by a coefficient of variance.

The bead may be any bead described herein. For example, a bead may be porous, non-porous, solid, semi-solid, semi-fluidic, fluidic, and/or a combination thereof. In some instances, a bead may be dissolvable, disruptable, and/or degradable. In some cases, a bead may not be degradable. In some cases, the bead may be a gel bead. A gel bead may be a hydrogel bead. A gel bead may be formed from molecular precursors, such as a polymeric or monomeric species. A semi-solid bead may be a liposomal bead. Solid beads may comprise metals including iron oxide, gold, and silver. In some cases, the bead may be a silica bead. In some cases, the bead can be rigid. In other cases, the bead may be flexible and/or compressible.

A bead may comprise natural and/or synthetic materials. For example, a bead can comprise a natural polymer, a synthetic polymer or both natural and synthetic polymers. Examples of natural polymers include proteins and sugars such as deoxyribonucleic acid, rubber, cellulose, starch (e.g., amylose, amylopectin), proteins, enzymes, polysaccharides, silks, polyhydroxyalkanoates, chitosan, dextran, collagen, carrageenan, ispaghula, acacia, agar, gelatin, shellac, sterculia gum, xanthan gum, Corn sugar gum, guar gum, gum karaya, agarose, alginic acid, alginate, or natural polymers thereof. Examples of synthetic polymers include acrylics, nylons, silicones, spandex, viscose rayon, polycarboxylic acids, polyvinyl acetate, polyacrylamide, polyacrylate, polyethylene glycol, polyurethanes, polylactic acid, silica, polystyrene, polyacrylonitrile, polybutadiene, polycarbonate, polyethylene, polyethylene terephthalate, poly(chlorotrifluoroethylene), poly(ethylene oxide), poly(ethylene terephthalate), polyethylene, polyisobutylene, poly(methyl methacrylate), poly(oxymethylene), polyformaldehyde, polypropylene, polystyrene, poly(tetrafluoroethylene), poly(vinyl acetate), poly(vinyl alcohol), poly(vinyl chloride), poly(vinylidene dichloride), poly(vinylidene difluoride), poly(vinyl fluoride) and/or combinations (e.g., co-polymers) thereof. Beads may also be formed from materials other than polymers, including lipids, micelles, ceramics, glass-ceramics, material composites, metals, other inorganic materials, and others.

The bead may be of any suitable shape. Examples of bead shapes include, but are not limited to, spherical, non-spherical, oval, oblong, amorphous, circular, cylindrical, and variations thereof. Beads may be of uniform size or heterogeneous size. In some cases, the diameter of a bead may be at least about 10 nanometers (nm), 100 nm, 500 nm, 1 micrometer (μm), 5 μm, 10 μm, 20 μm, 30 μm, 40 μm, 50 μm, 60 μm, 70 μm, 80 μm, 90 μm, 100 μm, 250 μm, 500 μm, 1 mm, or greater. In some cases, a bead may have a diameter of less than about 10 nm, 100 nm, 500 nm, 1 μm, 5 μm, 10 μm, 20 μm, 30 μm, 40 μm, 50 μm, 60 μm, 70 μm, 80 μm, 90 μm, 100 μm, 250 μm, 500 μm, 1 mm, or less. In some cases, a bead may have a diameter in the range of about 40-75 μm, 30-75 μm, 20-75 μm, 40-85 μm, 40-95 μm, 20-100 μm, 10-100 μm, 1-100 μm, 20-250 μm, or 20-500 μm.

In certain aspects, beads can be provided as a population or plurality of beads having a relatively monodisperse size distribution. Where it may be desirable to provide relatively consistent amounts of reagents within partitions, maintaining relatively consistent bead characteristics, such as size, can contribute to the overall consistency. In particular, the beads described herein may have size distributions that have a coefficient of variation in their cross-sectional dimensions of less than 50%, less than 40%, less than 30%, less than 20%, and in some cases less than 15%, less than 10%, less than 5%, or less.

In some instances, the bead that is optically tagged may be a cell bead, which are described further elsewhere herein. Beads, and characteristics thereof, are described further elsewhere herein.

A bead may be optically tagged by a nucleic acid probe (e.g., modified probe) comprising a fluorescent tag. One or more signals (e.g., fluorescent signals) detected from the optically tagged bead may be used to determine one or more characteristics or parameters of the bead, such as a bead size and/or bead shape. Beneficially, such characteristics or parameters may be useful as sequencing-orthogonal data, such as for quality control and process optimization purposes.

The methods described herein may involve partitioning a tagged bead. In some instances, a bead may be optically tagged within a partition. Alternatively or in addition, a bead may be optically tagged prior to partitioning. In some instances, one or more beads may be partitioned in isolation such that the partitions comprise the one or more beads. In some instances, one or more beads may be co-partitioned with one or more other objects, such as biological particles (e.g., cells, nucleic acid molecules, proteins, etc.), other types of beads (e.g., gel beads, barcode-carrying beads, cell beads, etc.), and other reagents. In non-limiting examples, a partition may partition a single bead, a partition may partition a single cell, a partition may partition multiple beads, a partition may partition multiple cells, a partition can co-partition a single bead and a single cell, a partition can co-partition any combination of one or more beads and one more cells, a partition can partition an analyte (e.g., target analyte), and a partition can co-partition any combination of one or more beads and one or more analytes (e.g., target analytes). One or more rounds of partitioning may facilitate downstream processing of a bead and/or an analyte, such as by providing isolated reaction chambers for performing one or more chemical reactions. A partition may be a droplet. A partition may be a well. Partitions, and systems and methods for partitioning, are described elsewhere herein.

Beneficially, one or more characteristics or parameters of the partition, such as partition size, partition occupancy, and the like, may be determined based on the methods described herein. Further, one or more characteristics or parameters of an occupant of the partition, such as an analyte (e.g., cell, reagent, etc.) may be determined based on the methods described herein. For example, one or more signals detected from a fluorescent tag of a partitioned (or co-partitioned) optically tagged bead may include cell occupancy in the partition (or cell occupancy rate in a plurality of partitions), bead occupancy in the partition (or bead occupancy in a plurality of partitions), partition size (e.g., bead-occupied partition size, cell-occupied partition size, etc.), reagent occupancy in the partition (e.g., concentrations thereof), cell phenotype (e.g., cell structure, cell size, cell morphology, protein expression, etc.), and the like. Such characteristics or parameters may be useful as sequencing-orthogonal data, such as for quality control and process optimization purposes.

The order of the processing operations involving the optically tagged bead may be varied. For example, in some cases, signals from the fluorescent tag can be detected before conducting chemical reactions with the tagged bead. Alternatively or in addition, the signals can be detected subsequent to conducting chemical reactions. Alternatively or in addition, the signals can be detected concurrently with conducting chemical reactions. In another example, in some cases, a bead may be optically tagged, and thereafter the optically tagged bead may be partitioned or co-partitioned with a biological particle. Alternatively, a bead may be partitioned or co-partitioned with a nucleic acid probe and/or a biological particle, and thereafter optically tagged within the partition.

A bead and a tagged nucleic acid probe can be hybridized to generate an optically tagged bead. In some instances, the bead can comprise a select region, which in turn can comprise a binding sequence that can hybridize with the nucleic acid probe.

The methods described herein provide great flexibility in both probe design and bead design. For example, the binding sequence on the bead may be selected to comprise one or more sequences that are complementary to one or more sequences of the nucleic acid probe. Alternatively or in addition, the nucleic acid probe may be selected to comprise one or more sequences complementary to those of the binding sequence. In some cases, the binding sequence may be 100% complementary to a sequence of the nucleic acid probe. In other cases, the binding sequence may be less than 100% complementary to a sequence of the nucleic acid probe. In some instances, a region on the bead may be selected and configured to comprise the binding sequence, or plurality thereof, to hybridize to the nucleic acid probe, or plurality thereof. In some instances, a plurality of regions on the bead may be selected and configured to comprise the binding sequence, or plurality thereof, to hybridize to the nucleic acid probe, or plurality thereof. For example, the plurality of regions may form a regular or irregular pattern on a bead surface or internally within a bead. Similarly, the sequence, size, density, and/or concentration of one or more binding sequences, and one or more regions thereof on or in the bead may be selected and configured on or in the bead to hybridize to one more nucleic acid probe. In some instances, a bead may comprise one type of binding sequence configured to hybridize to a nucleic acid probe (e.g., tagged by a fluorescent tag). In some instances, a bead may comprise a plurality of different types of binding sequences configured to hybridize to a plurality of different types of nucleic acid probes (e.g., tagged by the same fluorescent tag or tagged by different fluorescent tags). In some instances, the fluorophore(s) on the nucleic acid probes can be selected for detection at a particular frequency, or range thereof.

A bead may comprise a plurality of molecules attached thereto the bead. The plurality of molecules can comprise the binding sequence, as described elsewhere herein. The plurality of molecules can comprise any number of functional and/or barcodes sequences, as described elsewhere herein, such as with respect to FIG. 8. For an example of additional functional sequences that may be attached to beads, see, e.g., U.S. Pat. Nos. 9,951,386; 10,011,872; U.S. Pat. Pub. 20180340171; and U.S. Pat. Pub. 20190249226; the disclosures of which are each incorporated by reference herein in their entireties. In some instances, a single molecule of the plurality of molecules may comprise a plurality of sequences (e.g., functional sequence, barcode sequence, binding sequence). For example, a first molecule of a bead can comprise all of a flow cell adapter sequence, a barcode sequence common to the bead, a unique molecular identifying sequence unique to the first molecule within the plurality of molecules attached to the bead, a binding sequence configured to hybridize to the nucleic acid probe described herein, and a primer sequence configured to hybridize to a target analyte, and/or multiples thereof. In some instances, different molecules on the bead may comprise different sequences (e.g., different combinations of sequences). In some instances, any functional and/or barcode sequence can also act as, or comprise, a binding sequence for the nucleic acid probes described herein, without need for a separate binding sequence. For example a primer sequence configured to hybridize to a target analyte may also act as, or comprise, a binding sequence for the nucleic acid probe. Beneficially, the same nucleic acid probes may simultaneously determine the one or more characteristics and/or parameters of the bead, partition, and/or other partition occupant, and also measure, for example, a primer concentration on a per bead basis.

The nucleic acid probes (e.g., including modified probes as described herein) can comprise deoxyribonucleotides or ribonucleotides. The nucleic acid probes can comprise naturally occurring or synthetic nucleotides. The nucleic acid probes can have modified heterocyclic bases. The modification can be methylated purines or pyrimidines, acylated purines or pyrimidines, alkylated riboses, or other heterocycles. The nucleic acid probes can have modified sugar moieties. The modified sugar moieties can include peptide nucleic acid. The nucleic acid probe can comprise peptide nucleic acid. The nucleic acid probe can comprise threose nucleic acid. The nucleic acid probe can comprise locked nucleic acid. The nucleic acid probe can comprise hexitol nucleic acid. The nucleic acid probe can be flexible nucleic acid. The nucleic acid probe can comprise glycerol nucleic acid. Nucleic acid probes may comprise, or be modified to comprise, 3' chain-terminating modifications, fluorophores at a 3' end (e.g., in addition a fluorophore at a 5' end), one or more carbon spacer at a 3' end (e.g., a 3 carbon (C3) spacer), large molecules (e.g., biotin) at a 3' end, an inverted base at the 3' end, or any combination thereof. Nucleic acid probes may comprise, or be modified to comprise, unlocked nucleic acids. Nucleic acid probes may comprise, or be modified to comprise a sequence having one or more mismatched bases from a binding sequence of the bead.

The nucleic acid probes can comprise one or more fluorescent tags at the 5' ends. A plurality of nucleic acid probes may comprise different fluorescent tags such that an optically tagged bead, hybridized to the plurality of nucleic acid probes, can emit more than one fluorescent signal. Alternatively, the plurality of nucleic acid probes may comprise the same fluorescent tag, thereby emitting one fluorescent signal when detected from the optically tagged bead. The fluorescent tag can comprise a fluorophore. For example, the fluorophore can be from a group comprising: 7-AAD (7-Aminoactinomycin D), Acridine Orange (+DNA), Acridine Organe (+RNA), Alexa Fluor® 350, Alexa Fluor® 430, Alexa Fluor® 488, Alexa Fluor® 532, Alexa Fluor® 546, Alexa Fluor® 555, Alexa Fluor® 568, Alexa Fluor® 594, Alexa Fluor® 633, Alexa Fluor® 647, Alexa Fluor® 660, Alexa Fluor® 680, Alexa Fluor® 700, Alexa Fluor® 750, Allophycocyanin (APC), AMCA/AMCA-X, 7-Aminoactinomycin D (7-AAD), 7-Amino-4-methylcoumarin, 6-Aminoquinoline, Aniline Blue, ANS, APC-Cy7, ATTO-TAG™ CBQCA, ATTO-TAG™ FQ, Auramine O-Feulgen, BCECF (high pH), BFP (Blue Fluorescent Protein), BFP/GFP FRET, BOBO™-1/BO-PRO™-1, BOBO™-3/BO-PRO™-3, BODIPYR FL, BODIPY® TMR, BODIPY® TR-X, BODIPY® 530/550, BODIPY® 558/568, BODIPY® 564/570, BODIPY® 581/591, BODIPY® 630/650-X, BODIPY® 650-665-X, BTC, Calcein, Calcein Blue, Calcium Crimson™, Calcium Green-1™, Calcium Orange™, Calcofluor® White, 5-Carboxyfluoroscein (5-FAM), 5-Carboxynaphthofluoroscein, 6-Carboxyrhodamine 6G, 5-Carboxytetramethylrhodamine (5-TAMRA), Carboxy-X-rhodamine (5-ROX), Cascade Blue®, Cascade Yellow™, CCF2 (GeneBLAzer™), CFP (Cyan Fluorescent Protein), CFP/YFP FRET, Chromomycin A3, Cl-NERF (low pH), CPM, 6-CR 6G, CTC Formazan, Cy2®, Cy3®, Cy3.5®, Cy5®, Cy5.5®, Cy7®, Cychrome (PE-Cy5), Dansylamine, Dansyl cadaverine, Dansylchloride, DAPI, Dapoxyl, DCFH, DHR, DiA (4-Di-16-ASP), DiD (DilC18 (5)), DIDS, Dil (DilC18 (3)), DiO (DiOC18 (3)), DiR (DilC18 (7)), Di-4 ANEPPS, Di-8 ANEPPS, DM-NERF (4.5-6.5 pH), DsRed (Red Fluorescent Protein), EBFP, ECFP, EGFP, ELF®-97 alcohol, Eosin, Erythrosin, Ethidium bromide, Ethidium homodimer-1 (EthD-1), Europium (III) Chloride, 5-FAM (5-Carboxyfluorescein), Fast Blue, Fluorescein-dT phosphoramidite, FITC, Fluo-3, Fluo-4, FluorX®, Fluoro-Gold™ (high pH), Fluoro-Gold™ (low pH), Fluoro-Jade, FM® 1-43, Fura-2 (high calcium), Fura-2/BCECF, Fura Red™ (high calcium), Fura Red™/Fluo-3, GeneBLAzer™ (CCF2), GFP Red Shifted (rsGFP), GFP Wild Type, GFP/BFP FRET, GFP/DsRed FRET, Hoechst 33342 & 33258, 7-Hydroxy-4-methylcoumarin (pH 9), 1,5 IAEDANS, Indo-1 (high calcium), Indo-1 (low calcium), Indodicarbocyanine, Indotricarbocyanine, JC-1, 6-JOE, JOJO™-1/JO-PRO™-1, LDS 751 (+DNA), LDS 751 (+RNA), LOLO™-1/LO-PRO™-1, Lucifer Yellow, LysoSensor™ Blue (pH 5), LysoSensor™ Green (pH 5), LysoSensor™ Yellow/Blue (pH 4.2), LysoTracker® Green, LysoTracker® Red, LysoTracker® Yellow, Mag-Fura-2, Mag-Indo-1, Magnesium Green™, Marina Blue®, 4-Methylumbelliferone, Mithramycin, MitoTracker® Green, MitoTracker® Orange, MitoTracker® Red, NBD (amine), Nile Red, Oregon Green® 488, Oregon Green® 500, Oregon Green® 514, Pacific Blue, PBF1, PE (R-phycoerythrin), PE-Cy5, PE-Cy7, PE-Texas Red, PerCP (Peridinin chlorphyll protein), PerCP-Cy5.5 (TruRed), PharRed (APC-Cy7), C-phycocyanin, R-phycocyanin, R-phycoerythrin (PE), PI (Propidium Iodide), PKH26, PKH67, POPO™-1/PO-PRO™-1, POPO™-3/PO-PRO™-3, Propidium Iodide (PI), PyMPO, Pyrene, Pyronin Y, Quantam Red (PE-Cy5), Quinacrine Mustard, R670 (PE-Cy5), Red 613 (PE-Texas Red), Red Fluorescent Protein (DsRed), Resorufin, RH 414, Rhod-2, Rhodamine B, Rhodamine Green™, Rhodamine Red™, Rhodamine Phalloidin, Rhodamine 110, Rhodamine 123, 5-ROX (carboxy-X-rhodamine), S65A, S65C, S65L, S65T, SBFI, SITS, SNAFL®-1 (high pH), SNAFL®-2, SNARF®-1 (high pH), SNARFR-1 (low pH), Sodium Green™, SpectrumAqua®, SpectrumGreen® #1, SpectrumGreen® #2, SpectrumOrange®, SpectrumRed®, SYTOR 11, SYTOR 13, SYTOR 17, SYTOR 45, SYTOX® Blue, SYTOX® Green, SYTOX® Orange, 5-TAMRA (5-Carboxytetramethylrhodamine), Tetramethylrhodamine (TRITC), Texas Red®/Texas Red®-X, Texas Red®-X (NHS Ester), Thiadicarbocyanine, Thiazole Orange, TOTO®-1/TO-PRO®-1, TOTO®-3/TO-PRO®-3, TO-PRO®-5, Tri-color (PE-Cy5), TRITC (Tetramethylrhodamine), TruRed (PerCP-Cy5.5), WW 781, X-Rhodamine (XRITC), Y66F, Y66H, Y66 W, YFP (Yellow Fluorescent Protein), YOYO®-1/YO-PRO®-1, YOYO®-3/YO-PRO®-3, 6-FAM (Fluorescein), 6-FAM (NHS Ester), 6-FAM (Azide), HEX, TAMRA (NHS Ester), Yakima Yellow, MAX, TET, TEX615, ATTO 488, ATTO 532, ATTO 550, ATTO 565, ATTO Rho101, ATTO 590, ATTO 633, ATTO 647N, TYE 563, TYE 665, TYE 705, 5' IRDye® 700, 5' IRDye® 800, 5' IRDye® 800CW (NHS Ester), WellRED D4 Dye, WellRED D3 Dye, WellRED D2 Dye, Lightcycler® 640 (NHS Ester), and Dy 750 (NHS Ester). In some instances, the tag can be selected prior to hybridization of the nucleic acid probe and the binding sequence of the bead.

Figure 8:
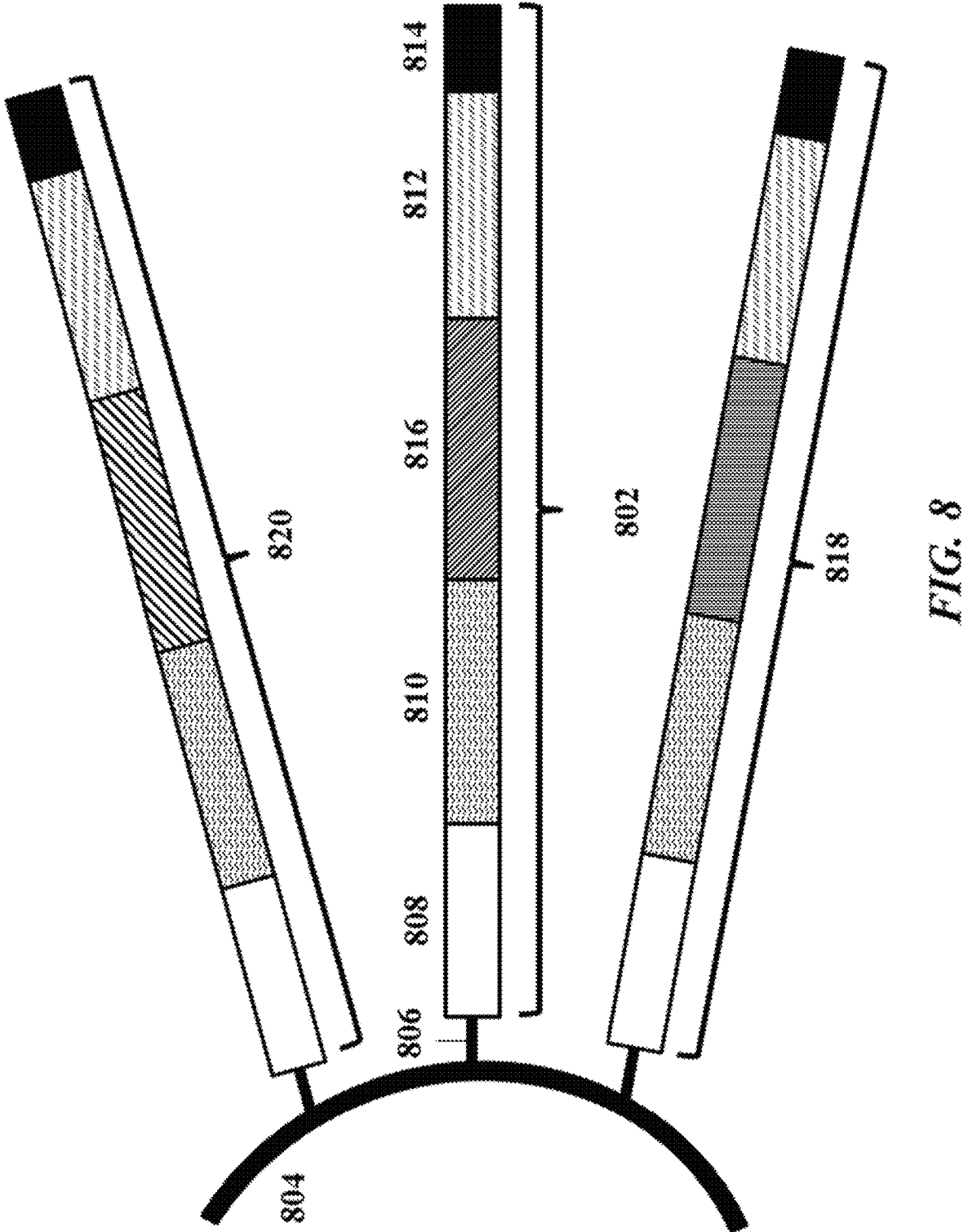
FIG. 8 illustrates an example of a barcode carrying bead.
Figure 9:
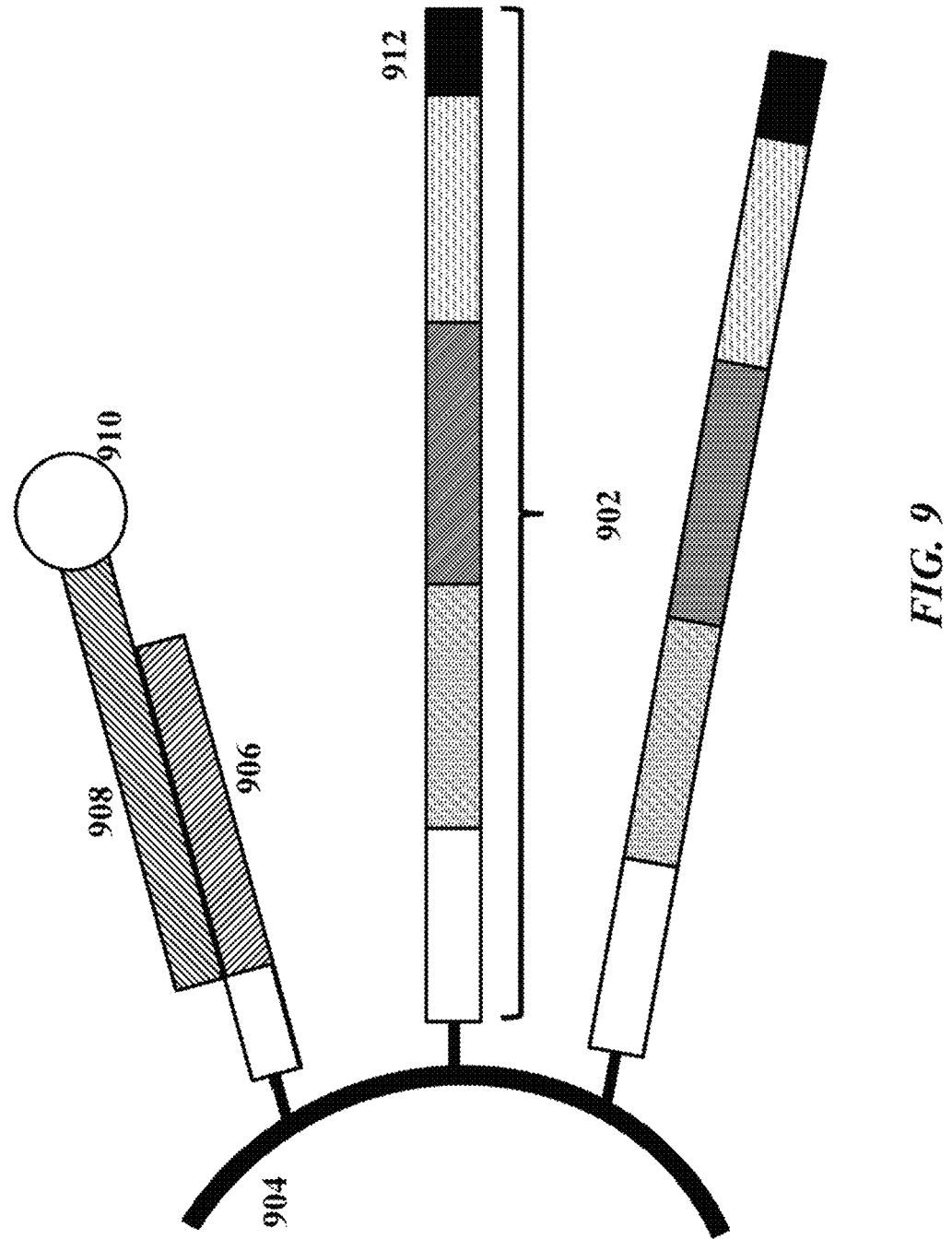
FIG. 9 illustrates an example of hybridization between a tagged nucleic acid probe and a bead to produce an optically tagged bead. The nucleic acid probe hybridizes to a nucleic acid molecule separate from the nucleic acid that comprises a priming sequence.

FIG. 9 illustrates an example of a tagged nucleic acid probe 908 hybridized to a bead 904. The nucleic acid probe 908 may comprise a sequence that is configured to hybridize to a binding sequence 906 of a selected region of the bead 904. The hybridization of the tagged nucleic acid probe 908 to the bead 904 can generate an optically tagged bead, as the nucleic acid probe 908 may further comprise a fluorescent tag 910. The bead may comprise other molecules, such as barcode molecules, that comprise sequences (or combinations of sequences) that are different than the binding sequence 906. In some instances, such other molecules may not include the binding sequence 906. For example, in a second molecule, the nucleic acid sequence 902 may comprise a priming sequence 912 such as an mRNA specific priming sequence (e.g., poly-T or targeted priming sequence) that can hybridize to a biological molecule (e.g. mRNA) but not the binding sequence 906. The bead 904 may comprise any number of functional and/or barcode sequences, such as described with respect to FIG. 8.

Figure 10:
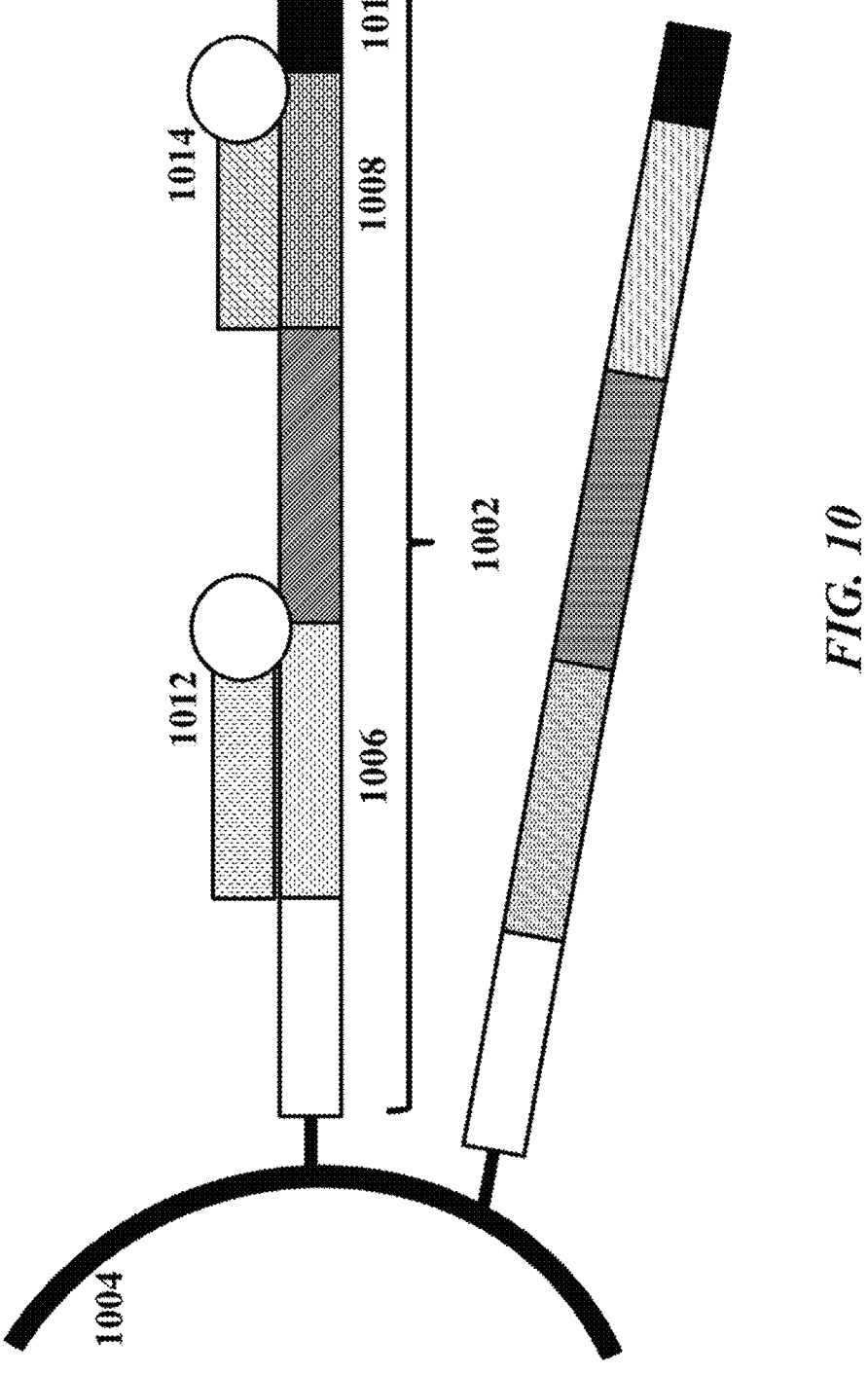
FIG. 10 shows another example of hybridization between a tagged nucleic acid probe and a bead. The nucleic acid probe hybridizes to the nucleic acid molecule that further comprises a priming sequence.

In another example, a bead 1004 may comprise a nucleic acid molecule 1002 that can in turn comprise two binding sequences 1006 and 1008, as shown in FIG. 10. Two nucleic acid probes 1012 and 1014 can be hybridized to the binding sequences 1006 and 1008, respectively. The nucleic acid probes 1012 and 1014 can comprise the same or distinct fluorescent tags at the respective 5'ends. For example, one of the probes may comprise a fluorophore with green fluorescence (e.g., FAM), and another probe may comprise a fluorophore with red fluorescence (e.g., Alexa). Each fluorophore may be visualized using appropriate optical instruments and protocols at its optimal wavelength. In some examples, multiple light filters may be used to visualize or capture the probes at distinct time intervals or within a short time interval. The nucleic acid molecule 1002 may also comprise a priming sequence 1010 that can be hybridized with a biological particle such as mRNA. A molecule attached to the bead 1004 may comprise any number of binding sequences. A molecule may be releasably attached to the bead (e.g., releasable upon application of one or more stimuli), as described elsewhere herein.

The bead may be subject to, or present in, one or more downstream chemical reactions. Such one or more downstream chemical reactions may be prior to, during, or subsequent to partitioning (or co-partitioning with an analyte or other reagents) of the bead in a partition. One or more modifications to the nucleic acid probe can reduce interference from the nucleic acid probes during the downstream chemical reactions.

In some instances, the modification can be made to a 3' end of the nucleic acid probe to render it substantially unreactive (e.g., unable to participate in hybridization) to the downstream chemical reactions, such as during or after hybridization to the bead. The modification can render the nucleic acid probe at least 60% less reactive in downstream chemical reaction as compared to an equivalent unmodified nucleic acid probe. The modification can render the nucleic acid probe at least 70%, 80%, or 90% less reactive in the downstream chemical reaction. The modification can render the nucleic acid probe at least 95%, 96%, 97%, 98%, or 99% less reactive in the downstream chemical reaction. In certain embodiments, the modification can render the nucleic acid probe completely unreactive (or inert) in the downstream chemical reactions. Various modifications can be performed to produce substantially unreactive (e.g., to one or more chemical reactions) nucleic acid probes. Beneficially, nucleic acid probes which at pre-modification are reactive (e.g., undesirably reactive) to one or more chemical reactions when hybridized to the bead, after modification, may become substantially unreactive to the one or more chemical reactions while maintaining optically detectable properties. Some example modification schemes are provided. A chain-terminating modification can be added to the 3' end of the nucleic acid probe. In some instances, a fluorophore can be attached to the 3' end of the tagged (at 5' end) nucleic acid probe. Spacers, such as spacer C3, spacer C6, spacer C9, spacer C12, and spacer C18, can be attached to the 3' end. Other modifications can include inverting a base at the 3' end. Modifications can include, for example, adding inverted dideoxy-T, amino linker, 2',3' Dideoxyadenosine (2,3ddA), 2',3' Dideoxycytosine (2,3ddC), 2',3' Dideoxythymidine (2,3ddT), 2',3' Dideoxyguanosine (2,3ddG), 3' Phosphate, 3'-Deoxycytidine (3'-dA), 3'-Deoxycytidine (3'-dC), 3'-Deoxycytidine (3'-dG), 3'-Deoxycytidine (3'dT), and 1,2-Dihydro-(3H)-pyrrolo[3,2-e]indole-7-carboxylate tripeptide. Alternatively or in addition, a large molecule can be attached to the 3' end. The large molecule may be biotin, for example.

A modified probe, modified from a nucleic acid probe comprising a probe sequence, may have the same, or substantially the same, probe sequence.

In some instances, the nucleic acid probe can be configured to, or be modified to, have destabilized hybridization with binding sequence of the bead which can help with the removal of the nucleic acid probe. The hybridization can comprise one or more mismatched base pairs, such as one mismatched base pair, two mismatched base pairs, three mismatched base pairs, or more. The nucleic acid probe may comprise unlocked nucleic acid.

One or more signals from the optically tagged bead can be detected to determine the one or more parameters and/or characteristics of the bead, partition, and/or other partition occupant. Such signals may be determined using a detector or one or more sensors configured to detect optical signals (e.g., fluorescent signals). A control system, as described elsewhere herein, may control and facilitate the detection, such as by transmitting instructions for detection to the sensors and receiving sensor data (e.g., raw or processed), process the signals, and determine the one or more characteristics or parameters. In non-limiting examples, one or more signals detected from a fluorescent tag of a partitioned (or co-partitioned) optically tagged bead may include bead size, bead shape, cell occupancy in the partition (or cell occupancy rate in a plurality of partitions), bead occupancy in the partition (bead occupancy in a plurality of partitions), partition size (e.g., bead-occupied partition size, cell-occupied partition size, etc.), reagent occupancy in the partition (e.g., concentrations thereof), cell phenotype (e.g., cell structure, cell size, cell morphology, protein expression, etc.), bead composition (e.g., primer concentration, sequence concentration, etc.) and the like. Such characteristics or parameters may be useful as sequencing-orthogonal data, such as for quality control and process optimization purposes. Particularly beneficial is the dual (or higher degree) ability of the nucleic acid probe to simultaneously probe the composition of the bead and provide the optical signals to characterize the parameters and the characteristics described above. For example a primer sequence on the bead configured to hybridize to a target analyte may also act as, or comprise, a binding sequence for the nucleic acid probe. Beneficially, the same nucleic acid probes may simultaneously determine the one or more characteristics and/or parameters of the bead, partition, and/or other partition occupant, and also measure, for example, a primer concentration on a per bead basis.

Figure 11:
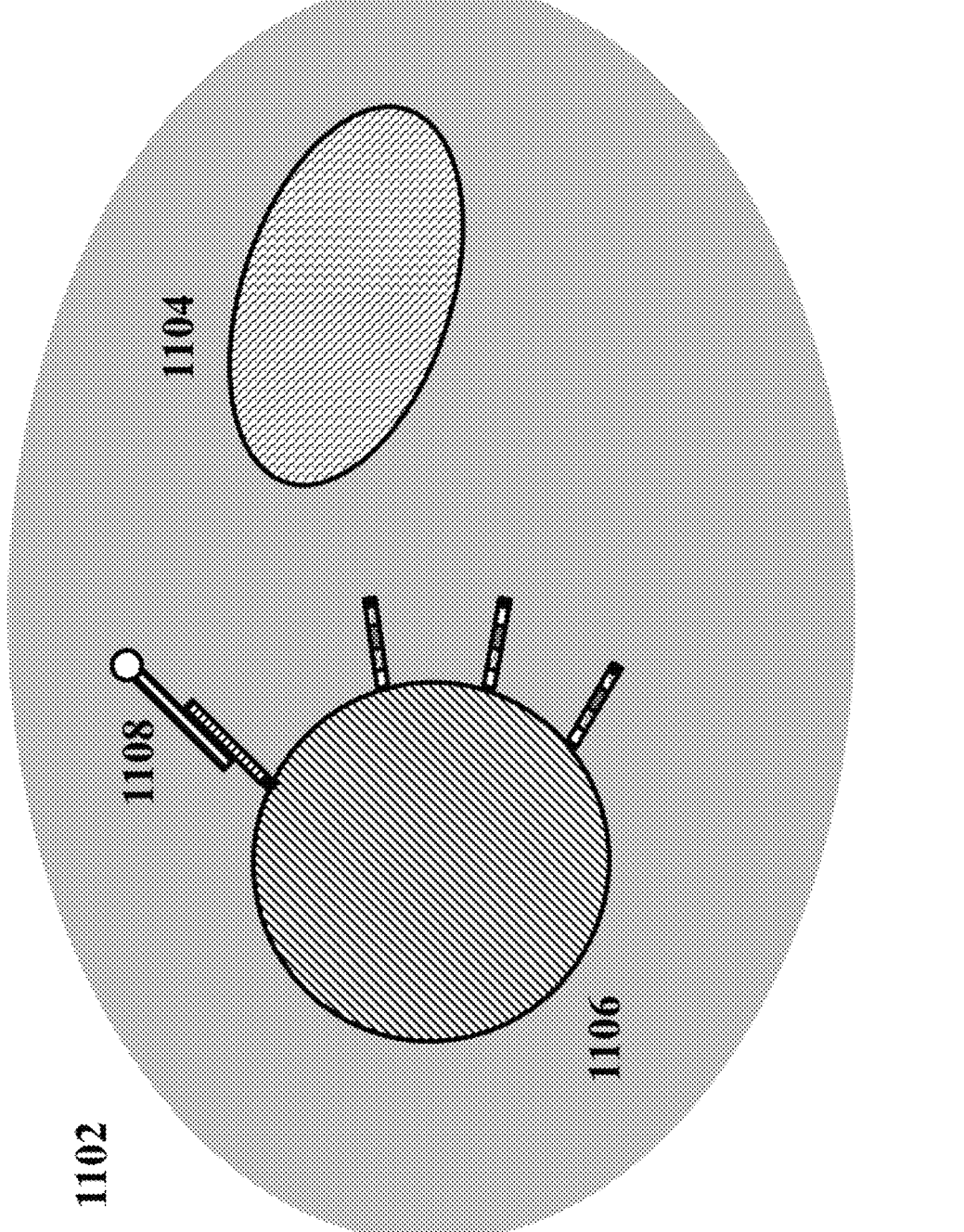
FIG. 11 shows an example of an optically tagged bead that has been partitioned in a partition.

FIG. 11 shows an example of an optically tagged bead 1106 that has been partitioned in a partition 1102. An optically tagged bead 1106 can be partitioned with an individual biological particle 1104. The optically tagged bead 1106 comprises tagged nucleic acid probe 1108 that has a modified 3' end to render the nucleic acid probe 1108 substantially unreactive in subsequent chemical reactions that may or may not be performed in the partition.

The one or more chemical reactions conducted with the bead, or otherwise in the presence of the bead, may be reactions necessary or otherwise helpful for, for example, sequencing and/or amplification of a biological particle, such as nucleic acid molecule. The one or more chemical reactions may be spontaneous or non-spontaneous reactions. In some instances, the one or more chemical reactions may be reactions necessary or otherwise helpful for, for example, PCR reactions. In some instances, a chemical reaction can be initiated by applying a stimuli, such as changing temperature, pressure, pH, and/or other environmental factors (e.g., locally, within a partition, in bulk mixture, etc.), or exposing, introducing, or contacting a first reactant to one or more other reactants (e.g., reagents), and/or applying other stimuli, such as radiation or other electromagnetic, electric, magnetic, optical, acoustic, electronic, or other stimuli.

Also provided herein are kits for bead processing and bead generation. In some instances, a kit may comprise a plurality of modified probes configured to hybridize to a bead comprising a binding sequence, wherein a modified probe of the plurality of modified probes comprises a fluorescent tag, wherein the modified probe is configured to hybridize to the binding sequence, and wherein the modified probe, when hybridized to the binding sequence, is substantially unreactive to one or more chemical reactions conducted with, or in a presence of, the bead hybridized to the modified probe. In some instances, the kit may further comprise the bead (e.g., comprising the binding sequence). For example, the plurality of modified probes may be any combination of probes described herein. Any of the components described herein may be provided in solution.

In some instances, a kit may comprise a plurality of nucleic acid probes configured to hybridize to a bead, wherein the plurality of nucleic acid probes, when hybridized to the bead, are substantially reactive to one or more chemical reactions conducted with, or in a presence of, the bead hybridized to the plurality of nucleic acid probes; a plurality of fluorophores; and reagents for modifying the plurality of nucleic acid probes to generate a plurality of modified probes, wherein the plurality of modified probes are (i) configured to hybridize to the bead, (ii) comprises the plurality of fluorophores, and (iii) when hybridized to the bead, are substantially unreactive to one or more chemical reactions conducted with, or in a presence of, the bead hybridized to the plurality of modified probes. In some instances, the kit may further comprise the bead (e.g., comprising the binding sequence). In some instances, the plurality of nucleic acid probes can comprise the plurality of fluorophores. In other instances, the plurality of nucleic acid probes may be provided separately from the plurality of fluorophores.

In some embodiments, the reagents comprise reagents configured to add a 3' chain-terminating modification to the plurality of nucleic acid probes. In some embodiments, the reagents comprise reagents configured to add a fluorophore to a 5' end of the plurality of nucleic acid probes. In some embodiments, the reagents comprise reagents configured to add a fluorophore to a 3' end of the plurality of nucleic acid probes. In some embodiments, the reagents comprise reagents configured to add a 3' chain-terminating modification to the plurality of nucleic acid probes, wherein the plurality of nucleic acid probes comprises the plurality of fluorophores at a 5' end. In some embodiments, the reagents comprise reagents configured to add a 3 carbon spacer to a 3' end of the plurality of nucleic acid probes. In some embodiments, the reagents comprise reagents configured to add a 6 carbon spacer to a 3' end of the plurality of nucleic acid probes. In some embodiments, the reagents comprise reagents configured to add a 9 carbon spacer to a 3' end of the plurality of nucleic acid probes. In some embodiments, the reagents comprise reagents configured to add a 18 carbon spacer to a 3' end of the plurality of nucleic acid probes. In some embodiments, the reagents comprise reagents configured to add a large molecule to a 3' end of the plurality of nucleic acid probes. For example, such reagents may comprise a biotin molecule for addition to the 3' end of the plurality of nucleic acid probes. In some embodiments, the reagents comprise reagents configured to invert a terminal base at a 3' end of the plurality of nucleic acid probes. In some embodiments, the modified probes comprise unlocked nucleic acid. Any of the components of any kit described herein may be provided in solution.

Systems and Methods for Sample Compartmentalization

In an aspect, the systems and methods described herein provide for the compartmentalization, depositing, or partitioning of one or more particles (e.g., biological particles, macromolecular constituents of biological particles, beads, reagents, etc.) into discrete compartments or partitions (referred to interchangeably herein as partitions), where each partition maintains separation of its own contents from the contents of other partitions. The partition can be a droplet in an emulsion. A partition may comprise one or more other partitions.

A partition may include one or more particles. A partition may include one or more types of particles. For example, a partition of the present disclosure may comprise one or more biological particles and/or macromolecular constituents thereof. A partition may comprise one or more gel beads. A partition may comprise one or more cell beads. A partition may include a single gel bead, a single cell bead, or both a single cell bead and single gel bead. A partition may include one or more reagents. Alternatively, a partition may be unoccupied. For example, a partition may not comprise a bead. A cell bead can be a biological particle and/or one or more of its macromolecular constituents encased inside of a gel or polymer matrix, such as via polymerization of a droplet containing the biological particle and precursors capable of being polymerized or gelled. Unique identifiers, such as barcodes, may be injected into the droplets previous to, subsequent to, or concurrently with droplet generation, such as via a microcapsule (e.g., bead), as described elsewhere herein. Microfluidic channel networks (e.g., on a chip) can be utilized to generate partitions as described herein. Alternative mechanisms may also be employed in the partitioning of individual biological particles, including porous membranes through which aqueous mixtures of cells are extruded into non-aqueous fluids.

The partitions can be flowable within fluid streams. The partitions may comprise, for example, micro-vesicles that have an outer barrier surrounding an inner fluid center or core. In some cases, the partitions may comprise a porous matrix that is capable of entraining and/or retaining materials within its matrix. The partitions can be droplets of a first phase within a second phase, wherein the first and second phases are immiscible. For example, the partitions can be droplets of aqueous fluid within a non-aqueous continuous phase (e.g., oil phase). In another example, the partitions can be droplets of a non-aqueous fluid within an aqueous phase. In some examples, the partitions may be provided in a water-in-oil emulsion or oil-in-water emulsion. A variety of different vessels are described in, for example, U.S. Patent Application Publication No. 2014/0155295, which is entirely incorporated herein by reference for all purposes. Emulsion systems for creating stable droplets in non-aqueous or oil continuous phases are described in, for example, U.S. Patent Application Publication No. 2010/0105112, which is entirely incorporated herein by reference for all purposes.

In the case of droplets in an emulsion, allocating individual particles to discrete partitions may in one non-limiting example be accomplished by introducing a flowing stream of particles in an aqueous fluid into a flowing stream or reservoir of a non-aqueous fluid. In some examples, the droplets may be generated at the junction of the two streams. Examples of droplet generation methods (e.g., with the aid of microfluidic devices) are shown in FIGS. 1-6, 7A and 7B. Fluid properties (e.g., fluid flow rates, fluid viscosities, etc.), particle properties (e.g., volume fraction, particle size, particle concentration, etc.), microfluidic architectures (e.g., channel geometry, etc.), and other parameters may be adjusted to control the occupancy of the resulting partitions (e.g., number of biological particles per partition, number of beads per partition, etc.). For example, partition occupancy can be controlled by providing the aqueous stream at a certain concentration and/or flow rate of particles. To generate single biological particle partitions, the relative flow rates of the immiscible fluids can be selected such that, on average, the partitions may contain less than one biological particle per partition in order to ensure that those partitions that are occupied are primarily singly occupied. In some cases, partitions among a plurality of partitions may contain at most one biological particle (e.g., bead, DNA, cell or cellular material). In some embodiments, the various parameters (e.g., fluid properties, particle properties, microfluidic architectures, etc.) may be selected or adjusted such that a majority of partitions are occupied, for example, allowing for only a small percentage of unoccupied partitions. The flows and channel architectures can be controlled as to ensure a given number of singly occupied partitions, less than a certain level of unoccupied partitions and/or less than a certain level of multiply occupied partitions.

FIG. 1 shows an example of a microfluidic channel structure 100 for partitioning individual biological particles. The channel structure 100 can include channel segments 102, 104, 106 and 108 communicating at a channel junction 110. In operation, a first aqueous fluid 112 that includes suspended biological particles (or cells) 114 may be transported along channel segment 102 into junction 110, while a second fluid 116 that is immiscible with the aqueous fluid 112 is delivered to the junction 110 from each of channel segments 104 and 106 to create discrete droplets 118, 120 of the first aqueous fluid 112 flowing into channel segment 108, and flowing away from junction 110. The channel segment 108 may be fluidically coupled to an outlet reservoir where the discrete droplets can be stored and/or harvested. A discrete droplet generated may include an individual biological particle 114 (such as droplets 118). A discrete droplet generated may include more than one individual biological particle 114 (not shown in FIG. 1). A discrete droplet may contain no biological particle 114 (such as droplet 120). Each discrete partition may maintain separation of its own contents (e.g., individual biological particle 114) from the contents of other partitions.

The second fluid 116 can comprise an oil, such as a fluorinated oil, that includes a fluorosurfactant for stabilizing the resulting droplets, for example, inhibiting subsequent coalescence of the resulting droplets 118, 120. Examples of particularly useful partitioning fluids and fluorosurfactants are described, for example, in U.S. Patent Application Publication No. 2010/0105112, which is entirely incorporated herein by reference for all purposes.

As will be appreciated, the channel segments described herein may be coupled to any of a variety of different fluid sources or receiving components, including reservoirs, tubing, manifolds, or fluidic components of other systems. As will be appreciated, the microfluidic channel structure 100 may have other geometries. For example, a microfluidic channel structure can have more than one channel junction. For example, a microfluidic channel structure can have 2, 3, 4, or 5 channel segments each carrying particles (e.g., biological particles, cell beads, and/or gel beads) that meet at a channel junction. Fluid may be directed to flow along one or more channels or reservoirs via one or more fluid flow units. A fluid flow unit can comprise compressors (e.g., providing positive pressure), pumps (e.g., providing negative pressure), actuators, and the like to control flow of the fluid. Fluid may also or otherwise be controlled via applied pressure differentials, centrifugal force, electrokinetic pumping, vacuum, capillary or gravity flow, or the like.

The generated droplets may comprise two subsets of droplets: (1) occupied droplets 118, containing one or more biological particles 114, and (2) unoccupied droplets 120, not containing any biological particles 114. Occupied droplets 118 may comprise singly occupied droplets (having one biological particle) and multiply occupied droplets (having more than one biological particle). As described elsewhere herein, in some cases, the majority of occupied partitions can include no more than one biological particle per occupied partition and some of the generated partitions can be unoccupied (of any biological particle). In some cases, though, some of the occupied partitions may include more than one biological particle. In some cases, the partitioning process may be controlled such that fewer than about 25% of the occupied partitions contain more than one biological particle, and in many cases, fewer than about 20% of the occupied partitions have more than one biological particle, while in some cases, fewer than about 10% or even fewer than about 5% of the occupied partitions include more than one biological particle per partition.

In some cases, it may be desirable to minimize the creation of excessive numbers of empty partitions, such as to reduce costs and/or increase efficiency. While this minimization may be achieved by providing a sufficient number of biological particles (e.g., biological particles 114) at the partitioning junction 110, such as to ensure that at least one biological particle is encapsulated in a partition, the Poissonian distribution may expectedly increase the number of partitions that include multiple biological particles. As such, where singly occupied partitions are to be obtained, at most about 95%, 90%, 85%, 80%, 75%, 70%, 65%, 60%, 55%, 50%, 45%, 40%, 35%, 30%, 25%, 20%, 15%, 10%, 5% or less of the generated partitions can be unoccupied.

In some cases, the flow of one or more of the biological particles (e.g., in channel segment 102), or other fluids directed into the partitioning junction (e.g., in channel segments 104, 106) can be controlled such that, in many cases, no more than about 50% of the generated partitions, no more than about 25% of the generated partitions, or no more than about 10% of the generated partitions are unoccupied. These flows can be controlled so as to present a non-Poissonian distribution of single-occupied partitions while providing lower levels of unoccupied partitions. The above noted ranges of unoccupied partitions can be achieved while still providing any of the single occupancy rates described above. For example, in many cases, the use of the systems and methods described herein can create resulting partitions that have multiple occupancy rates of less than about 25%, less than about 20%, less than about 15%, less than about 10%, and in many cases, less than about 5%, while having unoccupied partitions of less than about 50%, less than about 40%, less than about 30%, less than about 20%, less than about 10%, less than about 5%, or less.

Figure 2:
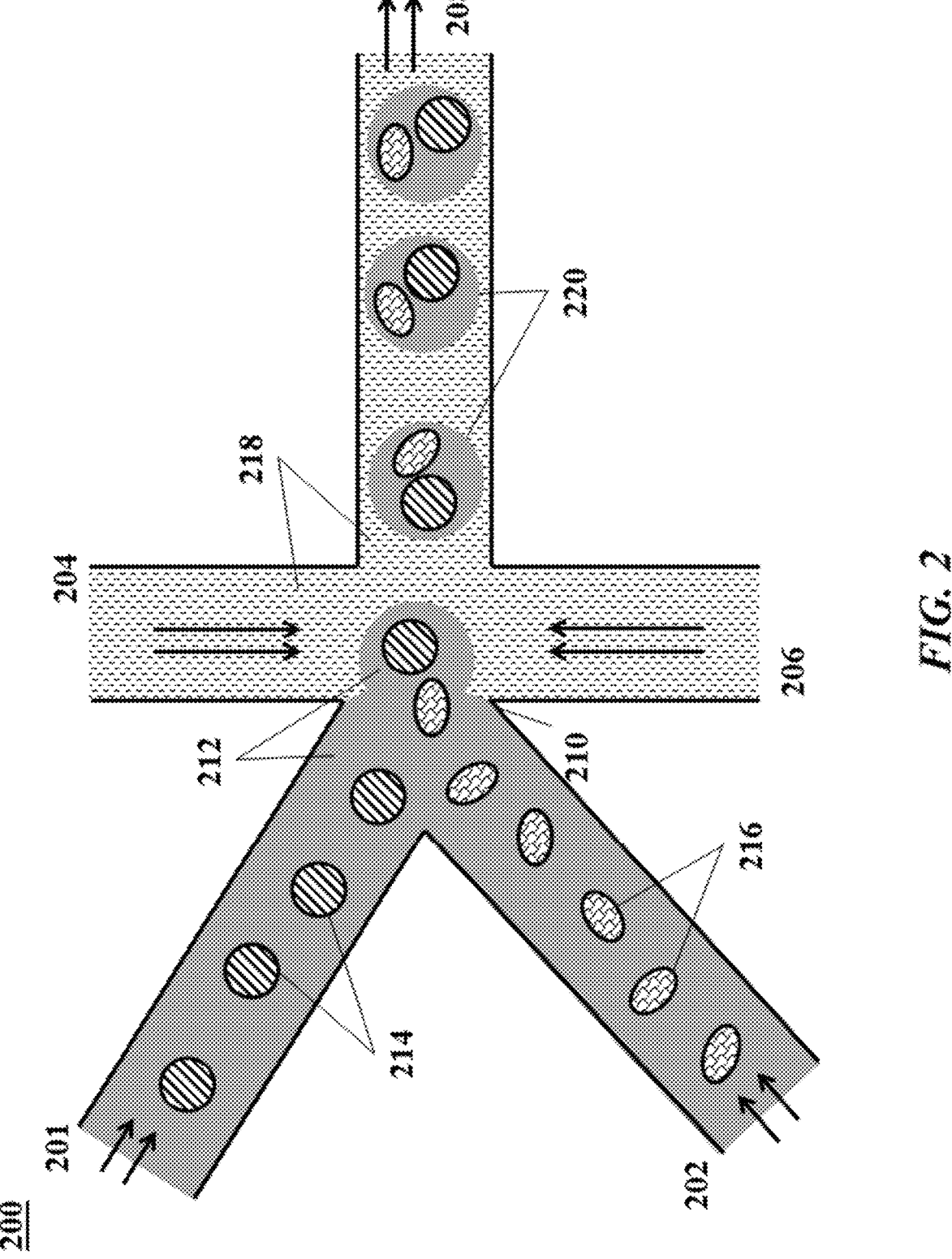
FIG. 2 shows an example of a microfluidic channel structure for delivering barcode carrying beads to droplets.

As will be appreciated, the above-described occupancy rates are also applicable to partitions that include both biological particles and additional reagents, including, but not limited to, microcapsules or beads (e.g., gel beads) carrying barcoded nucleic acid molecules (e.g., oligonucleotides) (described in relation to FIG. 2). The occupied partitions (e.g., at least about 10%, 20%, 30%, 40%, 50%, 60%, 70%, 80%, 90%, 95%, or 99% of the occupied partitions) can include both a microcapsule (e.g., bead) comprising barcoded nucleic acid molecules and a biological particle.

In another aspect, in addition to or as an alternative to droplet based partitioning, biological particles may be encapsulated within a microcapsule that comprises an outer shell, layer or porous matrix in which is entrained one or more individual biological particles or small groups of biological particles. The microcapsule may include other reagents. Encapsulation of biological particles may be performed by a variety of processes. Such processes may combine an aqueous fluid containing the biological particles with a polymeric precursor material that may be capable of being formed into a gel or other solid or semi-solid matrix upon application of a particular stimulus to the polymer precursor. Such stimuli can include, for example, thermal stimuli (e.g., either heating or cooling), photo-stimuli (e.g., through photo-curing), chemical stimuli (e.g., through cross-linking, polymerization initiation of the precursor (e.g., through added initiators)), mechanical stimuli, or a combination thereof.

Preparation of microcapsules comprising biological particles may be performed by a variety of methods. For example, air knife droplet or aerosol generators may be used to dispense droplets of precursor fluids into gelling solutions in order to form microcapsules that include individual biological particles or small groups of biological particles. Likewise, membrane based encapsulation systems may be used to generate microcapsules comprising encapsulated biological particles as described herein. Microfluidic systems of the present disclosure, such as that shown in FIG. 1, may be readily used in encapsulating cells as described herein. In particular, and with reference to FIG. 1, the aqueous fluid 112 comprising (i) the biological particles 114 and (ii) the polymer precursor material (not shown) is flowed into channel junction 110, where it is partitioned into droplets 118, 120 through the flow of non-aqueous fluid 116. In the case of encapsulation methods, non-aqueous fluid 116 may also include an initiator (not shown) to cause polymerization and/or crosslinking of the polymer precursor to form the microcapsule that includes the entrained biological particles. Examples of polymer precursor/initiator pairs include those described in U.S. Patent Application Publication No. 2014/0378345, which is entirely incorporated herein by reference for all purposes.

For example, in the case where the polymer precursor material comprises a linear polymer material, such as a linear polyacrylamide, PEG, or other linear polymeric material, the activation agent may comprise a cross-linking agent, or a chemical that activates a cross-linking agent within the formed droplets. Likewise, for polymer precursors that comprise polymerizable monomers, the activation agent may comprise a polymerization initiator. For example, in certain cases, where the polymer precursor comprises a mixture of acrylamide monomer with a N,N'-bis-(acryloyl) cystamine (BAC) comonomer, an agent such as tetraethyl-methylenediamine (TEMED) may be provided within the second fluid streams 116 in channel segments 104 and 106, which can initiate the copolymerization of the acrylamide and BAC into a cross-linked polymer network, or hydrogel.

Upon contact of the second fluid stream 116 with the first fluid stream 112 at junction 110, during formation of droplets, the TEMED may diffuse from the second fluid 116 into the aqueous fluid 112 comprising the linear polyacrylamide, which will activate the crosslinking of the polyacrylamide within the droplets 118, 120, resulting in the formation of gel (e.g., hydrogel) microcapsules, as solid or semi-solid beads or particles entraining the cells 114. Although described in terms of polyacrylamide encapsulation, other 'activatable' encapsulation compositions may also be employed in the context of the methods and compositions described herein. For example, formation of alginate droplets followed by exposure to divalent metal ions (e.g., Ca$^{2+}$ ions), can be used as an encapsulation process using the described processes. Likewise, agarose droplets may also be transformed into capsules through temperature based gelling (e.g., upon cooling, etc.).

In some cases, encapsulated biological particles can be selectively releasable from the microcapsule, such as through passage of time or upon application of a particular stimulus, that degrades the microcapsule sufficiently to allow the biological particles (e.g., cell), or its other contents to be released from the microcapsule, such as into a partition (e.g., droplet). For example, in the case of the polyacrylamide polymer described above, degradation of the microcapsule may be accomplished through the introduction of an appropriate reducing agent, such as DTT or the like, to cleave disulfide bonds that cross-link the polymer matrix. See, for example, U.S. Patent Application Publication No. 2014/0378345, which is entirely incorporated herein by reference for all purposes.

The biological particle can be subjected to other conditions sufficient to polymerize or gel the precursors. The conditions sufficient to polymerize or gel the precursors may comprise exposure to heating, cooling, electromagnetic radiation, and/or light. The conditions sufficient to polymerize or gel the precursors may comprise any conditions sufficient to polymerize or gel the precursors. Following polymerization or gelling, a polymer or gel may be formed around the biological particle. The polymer or gel may be diffusively permeable to chemical or biochemical reagents. The polymer or gel may be diffusively impermeable to macromolecular constituents of the biological particle. In this manner, the polymer or gel may act to allow the biological particle to be subjected to chemical or biochemical operations while spatially confining the macromolecular constituents to a region of the droplet defined by the polymer or gel. The polymer or gel may include one or more of disulfide cross-linked polyacrylamide, agarose, alginate, polyvinyl alcohol, polyethylene glycol (PEG)-diacrylate, PEG-acrylate, PEG-thiol, PEG-azide, PEG-alkyne, other acrylates, chitosan, hyaluronic acid, collagen, fibrin, gelatin, or elastin. The polymer or gel may comprise any other polymer or gel.

The polymer or gel may be functionalized to bind to targeted analytes, such as nucleic acids, proteins, carbohydrates, lipids or other analytes. The polymer or gel may be polymerized or gelled via a passive mechanism. The polymer or gel may be stable in alkaline conditions or at elevated temperature. The polymer or gel may have mechanical properties similar to the mechanical properties of the bead. For instance, the polymer or gel may be of a similar size to the bead. The polymer or gel may have a mechanical strength (e.g. tensile strength) similar to that of the bead. The polymer or gel may be of a lower density than an oil. The polymer or gel may be of a density that is roughly similar to that of a buffer. The polymer or gel may have a tunable pore size. The pore size may be chosen to, for instance, retain denatured nucleic acids. The pore size may be chosen to maintain diffusive permeability to exogenous chemicals such as sodium hydroxide (NaOH) and/or endogenous chemicals such as inhibitors. The polymer or gel may be biocompatible. The polymer or gel may maintain or enhance cell viability. The polymer or gel may be biochemically compatible. The polymer or gel may be polymerized and/or depolymerized thermally, chemically, enzymatically, and/or optically.

The polymer may comprise poly(acrylamide-co-acrylic acid) crosslinked with disulfide linkages. The preparation of the polymer may comprise a two-step reaction. In the first activation step, poly(acrylamide-co-acrylic acid) may be exposed to an acylating agent to convert carboxylic acids to esters. For instance, the poly(acrylamide-co-acrylic acid) may be exposed to 4-(4,6-dimethoxy-1,3,5-triazin-2-yl)-4-methylmorpholinium chloride (DMTMM). The polyacrylamide-co-acrylic acid may be exposed to other salts of 4-(4,6-dimethoxy-1,3,5-triazin-2-yl)-4-methylmorpholinium. In the second cross-linking step, the ester formed in the first step may be exposed to a disulfide crosslinking agent. For instance, the ester may be exposed to cystamine (2,2'-dithiobis(ethylamine)). Following the two steps, the biological particle may be surrounded by polyacrylamide strands linked together by disulfide bridges. In this manner, the biological particle may be encased inside of or comprise a gel or matrix (e.g., polymer matrix) to form a "cell bead." A cell bead can contain biological particles (e.g., a cell) or macromolecular constituents (e.g., RNA, DNA, proteins, etc.) of biological particles. A cell bead may include a single cell or multiple cells, or a derivative of the single cell or multiple cells. For example after lysing and washing the cells, inhibitory components from cell lysates can be washed away and the macromolecular constituents can be bound as cell beads. Systems and methods disclosed herein can be applicable to both cell beads (and/or droplets or other partitions) containing biological particles and cell beads (and/or droplets or other partitions) containing macromolecular constituents of biological particles.

Encapsulated biological particles can provide certain potential advantages of being more storable and more portable than droplet-based partitioned biological particles. Furthermore, in some cases, it may be desirable to allow biological particles to incubate for a select period of time before analysis, such as in order to characterize changes in such biological particles over time, either in the presence or absence of different stimuli. In such cases, encapsulation may allow for longer incubation than partitioning in emulsion droplets, although in some cases, droplet partitioned biological particles may also be incubated for different periods of time, e.g., at least 10 seconds, at least 30 seconds, at least 1 minute, at least 5 minutes, at least 10 minutes, at least 30 minutes, at least 1 hour, at least 2 hours, at least 5 hours, or at least 10 hours or more. The encapsulation of biological particles may constitute the partitioning of the biological particles into which other reagents are co-partitioned. Alternatively or in addition, encapsulated biological particles may be readily deposited into other partitions (e.g., droplets) as described above.

Beads

A partition may comprise one or more unique identifiers, such as barcodes. Barcodes may be previously, subsequently or concurrently delivered to the partitions that hold the compartmentalized or partitioned biological particle. For example, barcodes may be injected into droplets previous to, subsequent to, or concurrently with droplet generation. The delivery of the barcodes to a particular partition allows for the later attribution of the characteristics of the individual biological particle to the particular partition. Barcodes may be delivered, for example on a nucleic acid molecule (e.g., an oligonucleotide), to a partition via any suitable mechanism. Barcoded nucleic acid molecules can be delivered to a partition via a microcapsule. A microcapsule, in some instances, can comprise a bead. Beads are described in further detail below.

In some cases, barcoded nucleic acid molecules can be initially associated with the microcapsule and then released from the microcapsule. Release of the barcoded nucleic acid molecules can be passive (e.g., by diffusion out of the microcapsule). In addition or alternatively, release from the microcapsule can be upon application of a stimulus which allows the barcoded nucleic acid nucleic acid molecules to dissociate or to be released from the microcapsule. Such stimulus may disrupt the microcapsule, an interaction that couples the barcoded nucleic acid molecules to or within the microcapsule, or both. Such stimulus can include, for example, a thermal stimulus, photo-stimulus, chemical stimulus (e.g., change in pH or use of a reducing agent(s)), a mechanical stimulus, a radiation stimulus; a biological stimulus (e.g., enzyme), or any combination thereof.

The nucleic acid barcode molecules may be delivered to a partition (e.g., a droplet or well) via a support or carrier (e.g., a solid support, a semi-solid support, a bead, or other type of support). In some cases, nucleic acid barcode molecules may be initially associated with the solid support. The nucleic acid barcode molecules may be at some point, released from the solid support. The release of the barcoded nucleic acid molecules can be passive (e.g., by diffusion out of the support). Alternatively or in addition, the release of the nucleic acid barcode molecule from the support can occur upon application of a stimulus. Such stimulus may disrupt the support, disrupt an interaction that couples the barcoded nucleic acid molecule to the support, or both. The stimulus may be chemical, biological, biochemical (e.g., an enzyme), or physical, such as light, a chemical reagent, a change in pH (e.g., due to using a reducing agent) heat (thermal stimulus), a mechanical stimulus, an electrical stimulus, a magnetic stimulus, a radiation stimulus, an energy with any source, any other kind of stimulus, and/or any combination thereof. The release of the nucleic acid barcode molecule from the support (e.g., bead) may allow the nucleic acid barcode molecules to dissociate or to be released from the solid support.

In some cases, a nucleic acid barcode molecule may contain a barcode sequence and/or a functional sequence, such as a nucleic acid primer sequence or a template switch oligonucleotide (TSO) sequence. In some examples, the solid support may be a bead. A solid support, e.g., a bead, may be porous, non-porous, hollow (e.g., a microcapsule), solid, semi-solid, and/or a combination thereof. In addition, beads may be solid, semi-solid, semi-fluidic, fluidic, and/or a combination thereof. In some instances, a solid support, e.g., a bead, may be dissolvable, disruptable, and/or degradable. In some cases, a solid support, e.g., a bead, may not be degradable. In some cases, the solid support, e.g., a bead, may be a gel bead. A gel bead may be a hydrogel bead. A gel bead may be formed from molecular precursors, such as a polymeric or monomeric species. A semi-solid support, e.g., a bead, may be a liposomal bead. Solid supports, e.g., beads, may comprise metals including iron oxide, gold, and silver. In some cases, the solid support, e.g., the bead, may be a silica bead. In some cases, the solid support, e.g., a bead, can be rigid. In other cases, the solid support, e.g., a bead, may be flexible and/or compressible.

FIG. 2 shows an example of a microfluidic channel structure 200 for delivering barcode carrying beads to droplets. The channel structure 200 can include channel segments 201, 202, 204, 206 and 208 communicating at a channel junction 210. In operation, the channel segment 201 may transport an aqueous fluid 212 that includes a plurality of beads 214 (e.g., with nucleic acid molecules, oligonucleotides, molecular tags) along the channel segment 201 into junction 210. The plurality of beads 214 may be sourced from a suspension of beads. For example, the channel segment 201 may be connected to a reservoir comprising an aqueous suspension of beads 214. The channel segment 202 may transport the aqueous fluid 212 that includes a plurality of biological particles 216 along the channel segment 202 into junction 210. The plurality of biological particles 216 may be sourced from a suspension of biological particles. For example, the channel segment 202 may be connected to a reservoir comprising an aqueous suspension of biological particles 216. In some instances, the aqueous fluid 212 in either the first channel segment 201 or the second channel segment 202, or in both segments, can include one or more reagents, as further described below. A second fluid 218 that is immiscible with the aqueous fluid 212 (e.g., oil) can be delivered to the junction 210 from each of channel segments 204 and 206. Upon meeting of the aqueous fluid 212 from each of channel segments 201 and 202 and the second fluid 218 from each of channel segments 204 and 206 at the channel junction 210, the aqueous fluid 212 can be partitioned as discrete droplets 220 in the second fluid 218 and flow away from the junction 210 along channel segment 208. The channel segment 208 may deliver the discrete droplets to an outlet reservoir fluidly coupled to the channel segment 208, where they may be harvested.

As an alternative, the channel segments 201 and 202 may meet at another junction upstream of the junction 210. At such junction, beads and biological particles may form a mixture that is directed along another channel to the junction 210 to yield droplets 220. The mixture may provide the beads and biological particles in an alternating fashion, such that, for example, a droplet comprises a single bead and a single biological particle.

Beads, biological particles and droplets may flow along channels at substantially regular flow profiles (e.g., at regular flow rates). Such regular flow profiles may permit a droplet to include a single bead and a single biological particle. Such regular flow profiles may permit the droplets to have an occupancy (e.g., droplets having beads and biological particles) greater than 5%, 10%, 20%, 30%, 40%, 50%, 60%, 70%, 80%, 90%, or 95%. Such regular flow profiles and devices that may be used to provide such regular flow profiles are provided in, for example, U.S. Patent Publication No. 2015/0292988, which is entirely incorporated herein by reference.

The second fluid 218 can comprise an oil, such as a fluorinated oil, that includes a fluorosurfactant for stabilizing the resulting droplets, for example, inhibiting subsequent coalescence of the resulting droplets 220.

A discrete droplet that is generated may include an individual biological particle 216. A discrete droplet that is generated may include a barcode or other reagent carrying bead 214. A discrete droplet generated may include both an individual biological particle and a barcode carrying bead, such as droplets 220. In some instances, a discrete droplet may include more than one individual biological particle or no biological particle. In some instances, a discrete droplet may include more than one bead or no bead. A discrete droplet may be unoccupied (e.g., no beads, no biological particles).

Beneficially, a discrete droplet partitioning a biological particle and a barcode carrying bead may effectively allow the attribution of the barcode to macromolecular constituents of the biological particle within the partition. The contents of a partition may remain discrete from the contents of other partitions.

As will be appreciated, the channel segments described herein may be coupled to any of a variety of different fluid sources or receiving components, including reservoirs, tubing, manifolds, or fluidic components of other systems. As will be appreciated, the microfluidic channel structure 200 may have other geometries. For example, a microfluidic channel structure can have more than one channel junctions. For example, a microfluidic channel structure can have 2, 3, 4, or 5 channel segments each carrying beads that meet at a channel junction. Fluid may be directed flow along one or more channels or reservoirs via one or more fluid flow units. A fluid flow unit can comprise compressors (e.g., providing positive pressure), pumps (e.g., providing negative pressure), actuators, and the like to control flow of the fluid. Fluid may also or otherwise be controlled via applied pressure differentials, centrifugal force, electrokinetic pumping, vacuum, capillary or gravity flow, or the like.

In some instances, the bead may contain molecular precursors (e.g., monomers or polymers), which may form a polymer network via polymerization of the molecular precursors. In some cases, a precursor may be an already polymerized species capable of undergoing further polymerization via, for example, a chemical cross-linkage. In some cases, a precursor can comprise one or more of an acrylamide or a methacrylamide monomer, oligomer, or polymer. In some cases, the bead may comprise prepolymers, which are oligomers capable of further polymerization. For example, polyurethane beads may be prepared using prepolymers. In some cases, the bead may contain individual polymers that may be further polymerized together. In some cases, beads may be generated via polymerization of different precursors, such that they comprise mixed polymers, co-polymers, and/or block co-polymers. In some cases, the bead may comprise covalent or ionic bonds between polymeric precursors (e.g., monomers, oligomers, linear polymers), nucleic acid molecules (e.g., oligonucleotides), primers, and other entities. In some cases, the covalent bonds can be carbon-carbon bonds, thioether bonds, or carbon-heteroatom bonds.

Cross-linking may be permanent or reversible, depending upon the particular cross-linker used. Reversible cross-linking may allow for the polymer to linearize or dissociate under appropriate conditions. In some cases, reversible cross-linking may also allow for reversible attachment of a material bound to the surface of a bead. In some cases, a cross-linker may form disulfide linkages. In some cases, the chemical cross-linker forming disulfide linkages may be cystamine or a modified cystamine.

In some cases, disulfide linkages can be formed between molecular precursor units (e.g., monomers, oligomers, or linear polymers) or precursors incorporated into a bead and nucleic acid molecules (e.g., oligonucleotides). Cystamine (including modified cystamines), for example, is an organic agent comprising a disulfide bond that may be used as a crosslinker agent between individual monomeric or polymeric precursors of a bead. Polyacrylamide may be polymerized in the presence of cystamine or a species comprising cystamine (e.g., a modified cystamine) to generate polyacrylamide gel beads comprising disulfide linkages (e.g., chemically degradable beads comprising chemically-reducible cross-linkers). The disulfide linkages may permit the bead to be degraded (or dissolved) upon exposure of the bead to a reducing agent.

In some cases, chitosan, a linear polysaccharide polymer, may be crosslinked with glutaraldehyde via hydrophilic chains to form a bead. Crosslinking of chitosan polymers may be achieved by chemical reactions that are initiated by heat, pressure, change in pH, and/or radiation.

In some cases, a bead may comprise an acrydite moiety, which in certain aspects may be used to attach one or more nucleic acid molecules (e.g., barcode sequence, barcoded nucleic acid molecule, barcoded oligonucleotide, primer, or other oligonucleotide) to the bead. In some cases, an acrydite moiety can refer to an acrydite analogue generated from the reaction of acrydite with one or more species, such as, the reaction of acrydite with other monomers and cross-linkers during a polymerization reaction. Acrydite moieties may be modified to form chemical bonds with a species to be attached, such as a nucleic acid molecule (e.g., barcode sequence, barcoded nucleic acid molecule, barcoded oligonucleotide, primer, or other oligonucleotide). Acrydite moieties may be modified with thiol groups capable of forming a disulfide bond or may be modified with groups already comprising a disulfide bond. The thiol or disulfide (via disulfide exchange) may be used as an anchor point for a species to be attached or another part of the acrydite moiety may be used for attachment. In some cases, attachment can be reversible, such that when the disulfide bond is broken (e.g., in the presence of a reducing agent), the attached species is released from the bead. In other cases, an acrydite moiety can comprise a reactive hydroxyl group that may be used for attachment.

Functionalization of beads for attachment of nucleic acid molecules (e.g., oligonucleotides) may be achieved through a wide range of different approaches, including activation of chemical groups within a polymer, incorporation of active or activatable functional groups in the polymer structure, or attachment at the pre-polymer or monomer stage in bead production.

For example, precursors (e.g., monomers, cross-linkers) that are polymerized to form a bead may comprise acrydite moieties, such that when a bead is generated, the bead also comprises acrydite moieties. The acrydite moieties can be attached to a nucleic acid molecule (e.g., oligonucleotide), which may include a priming sequence (e.g., a primer for amplifying target nucleic acids, random primer, primer sequence for messenger RNA) and/or one or more barcode sequences. The one more barcode sequences may include sequences that are the same for all nucleic acid molecules coupled to a given bead and/or sequences that are different across all nucleic acid molecules coupled to the given bead. The nucleic acid molecule may be incorporated into the bead.

In some cases, the nucleic acid molecule can comprise a functional sequence, for example, for attachment to a sequencing flow cell, such as, for example, a P5 sequence for Illumina® sequencing. In some cases, the nucleic acid molecule or derivative thereof (e.g., oligonucleotide or poly-nucleotide generated from the nucleic acid molecule) can comprise another functional sequence, such as, for example, a P7 sequence for attachment to a sequencing flow cell for Illumina sequencing. In some cases, the nucleic acid mol-ecule can comprise a barcode sequence. In some cases, the primer can further comprise a unique molecular identifier (UMI). In some cases, the primer can comprise an R1 primer sequence for Illumina sequencing. In some cases, the primer can comprise an R2 primer sequence for Illumina sequenc-ing. Examples of such nucleic acid molecules (e.g., oligo-nucleotides, polynucleotides, etc.) and uses thereof, as may be used with compositions, devices, methods and systems of the present disclosure, are provided in U.S. Patent Pub. Nos. 2014/0378345 and 2015/0376609, each of which is entirely incorporated herein by reference.

FIG. 8 illustrates an example of a barcode carrying bead. A nucleic acid molecule 802, such as an oligonucleotide, can be coupled to a bead 804 by a releasable linkage 806, such as, for example, a disulfide linker. The same bead 804 may be coupled (e.g., via releasable linkage) to one or more other nucleic acid molecules 818, 820. The nucleic acid molecule 802 may be or comprise a barcode. As noted elsewhere herein, the structure of the barcode may comprise a number of sequence elements. The nucleic acid molecule 802 may comprise a functional sequence 808 that may be used in subsequent processing. For example, the functional sequence 808 may include one or more of a sequencer specific flow cell attachment sequence (e.g., a P5 sequence for Illumina® sequencing systems) and a sequencing primer sequence (e.g., a R1 primer for Illumina® sequencing sys-tems). The nucleic acid molecule 802 may comprise a barcode sequence 810 for use in barcoding the sample (e.g., DNA, RNA, protein, etc.). In some cases, the barcode sequence 810 can be bead-specific such that the barcode sequence 810 is common to all nucleic acid molecules (e.g., including nucleic acid molecule 802) coupled to the same bead 804. Alternatively or in addition, the barcode sequence 810 can be partition-specific such that the barcode sequence 810 is common to all nucleic acid molecules coupled to one or more beads that are partitioned into the same partition. The nucleic acid molecule 802 may comprise a specific priming sequence 812, such as an mRNA specific priming sequence (e.g., poly-T sequence), a targeted priming sequence, and/or a random priming sequence. The nucleic acid molecule 802 may comprise an anchoring sequence 814 to ensure that the specific priming sequence 812 hybridizes at the sequence end (e.g., of the mRNA). For example, the anchoring sequence 814 can include a random short sequence of nucleotides, such as a 1-mer, 2-mer, 3-mer or longer sequence, which can ensure that a poly-T segment is more likely to hybridize at the sequence end of the poly-A tail of the mRNA.

The nucleic acid molecule 802 may comprise a unique molecular identifying sequence 816 (e.g., unique molecular identifier (UMI)). In some cases, the unique molecular identifying sequence 816 may comprise from about 5 to about 8 nucleotides. Alternatively, the unique molecular identifying sequence 816 may compress less than about 5 or more than about 8 nucleotides. The unique molecular iden-tifying sequence 816 may be a unique sequence that varies across individual nucleic acid molecules (e.g., 802, 818, 820, etc.) coupled to a single bead (e.g., bead 804). In some cases, the unique molecular identifying sequence 816 may be a random sequence (e.g., such as a random N-mer sequence). For example, the UMI may provide a unique identifier of the starting mRNA molecule that was captured, in order to allow quantitation of the number of original expressed RNA. As will be appreciated, although FIG. 8 shows three nucleic acid molecules 802, 818, 820 coupled to the surface of the bead 804, an individual bead may be coupled to any number of individual nucleic acid molecules, for example, from one to tens to hundreds of thousands or even millions of individual nucleic acid molecules. The respective barcodes for the individual nucleic acid mol-ecules can comprise both common sequence segments or relatively common sequence segments (e.g., 808, 810, 812, etc.) and variable or unique sequence segments (e.g., 816) between different individual nucleic acid molecules coupled to the same bead.

In operation, a biological particle (e.g., cell, DNA, RNA, etc.) can be co-partitioned along with a barcode bearing bead 804. The barcoded nucleic acid molecules 802, 818, 820 can be released from the bead 804 in the partition. By way of example, in the context of analyzing sample RNA, the poly-T segment (e.g., 812) of one of the released nucleic acid molecules (e.g., 802) can hybridize to the poly-A tail of a mRNA molecule. Reverse transcription may result in a cDNA transcript of the mRNA, but which transcript includes each of the sequence segments 808, 810, 816 of the nucleic acid molecule 802. Because the nucleic acid molecule 802 comprises an anchoring sequence 814, it will more likely hybridize to and prime reverse transcription at the sequence end of the poly-A tail of the mRNA. Within any given partition, all of the cDNA transcripts of the individual mRNA molecules may include a common barcode sequence segment 810. However, the transcripts made from the dif-ferent mRNA molecules within a given partition may vary at the unique molecular identifying sequence 812 segment (e.g., UMI segment). Beneficially, even following any subsequent amplification of the contents of a given partition, the number of different UMIs can be indicative of the quantity of mRNA originating from a given partition, and thus from the biological particle (e.g., cell). As noted above, the transcripts can be amplified, cleaned up and sequenced to identify the sequence of the cDNA transcript of the mRNA, as well as to sequence the barcode segment and the UMI segment. While a poly-T primer sequence is described, other targeted or random priming sequences may also be used in priming the reverse transcription reaction. Likewise, although described as releasing the barcoded oligonucleotides into the partition, in some cases, the nucleic acid molecules bound to the bead (e.g., gel bead) may be used to hybridize and capture the mRNA on the solid phase of the bead, for example, in order to facilitate the separation of the RNA from other cell contents.

In some cases, precursors comprising a functional group that is reactive or capable of being activated such that it becomes reactive can be polymerized with other precursors to generate gel beads comprising the activated or activatable functional group. The functional group may then be used to attach additional species (e.g., disulfide linkers, primers, other oligonucleotides, etc.) to the gel beads. For example, some precursors comprising a carboxylic acid (COOH) group can co-polymerize with other precursors to form a gel bead that also comprises a COOH functional group. In some cases, acrylic acid (a species comprising free COOH groups), acrylamide, and bis(acryloyl) cystamine can be co-polymerized together to generate a gel bead comprising free COOH groups. The COOH groups of the gel bead can be activated (e.g., via 1-Ethyl-3-(3-dimethylaminopropyl) carbodiimide (EDC) and N-Hydroxysuccinimide (NHS) or 4-(4,6-Dimethoxy-1,3,5-triazin-2-yl)-4-methylmorpholinium chloride (DMTMM)) such that they are reactive (e.g., reactive to amine functional groups where EDC/NHS or DMTMM are used for activation). The activated COOH groups can then react with an appropriate species (e.g., a species comprising an amine functional group where the carboxylic acid groups are activated to be reactive with an amine functional group) comprising a moiety to be linked to the bead.

Beads comprising disulfide linkages in their polymeric network may be functionalized with additional species via reduction of some of the disulfide linkages to free thiols. The disulfide linkages may be reduced via, for example, the action of a reducing agent (e.g., DTT, TCEP, etc.) to generate free thiol groups, without dissolution of the bead. Free thiols of the beads can then react with free thiols of a species or a species comprising another disulfide bond (e.g., via thiol-disulfide exchange) such that the species can be linked to the beads (e.g., via a generated disulfide bond). In some cases, free thiols of the beads may react with any other suitable group. For example, free thiols of the beads may react with species comprising an acrydite moiety. The free thiol groups of the beads can react with the acrydite via Michael addition chemistry, such that the species comprising the acrydite is linked to the bead. In some cases, uncontrolled reactions can be prevented by inclusion of a thiol capping agent such as N-ethylmalieamide or iodoacetate.

Activation of disulfide linkages within a bead can be controlled such that only a small number of disulfide linkages are activated. Control may be exerted, for example, by controlling the concentration of a reducing agent used to generate free thiol groups and/or concentration of reagents used to form disulfide bonds in bead polymerization. In some cases, a low concentration (e.g., molecules of reducing agent: gel bead ratios of less than or equal to about 1:100, 000,000,000, less than or equal to about 1:10,000,000,000, less than or equal to about 1:1,000,000,000, less than or equal to about 1:100,000,000, less than or equal to about 1:10,000,000, less than or equal to about 1:1,000,000, less than or equal to about 1:100,000, less than or equal to about 1:10,000) of reducing agent may be used for reduction. Controlling the number of disulfide linkages that are reduced to free thiols may be useful in ensuring bead structural integrity during functionalization. In some cases, optically-active agents, such as fluorescent dyes may be coupled to beads via free thiol groups of the beads and used to quantify the number of free thiols present in a bead and/or track a bead.

In some cases, addition of moieties to a gel bead after gel bead formation may be advantageous. For example, addition of an oligonucleotide (e.g., barcoded oligonucleotide) after gel bead formation may avoid loss of the species during chain transfer termination that can occur during polymerization. Moreover, smaller precursors (e.g., monomers or cross linkers that do not comprise side chain groups and linked moieties) may be used for polymerization and can be minimally hindered from growing chain ends due to viscous effects. In some cases, functionalization after gel bead synthesis can minimize exposure of species (e.g., oligonucleotides) to be loaded with potentially damaging agents (e.g., free radicals) and/or chemical environments. In some cases, the generated gel may possess an upper critical solution temperature (UCST) that can permit temperature driven swelling and collapse of a bead. Such functionality may aid in oligonucleotide (e.g., a primer) infiltration into the bead during subsequent functionalization of the bead with the oligonucleotide. Post-production functionalization may also be useful in controlling loading ratios of species in beads, such that, for example, the variability in loading ratio is minimized. Species loading may also be performed in a batch process such that a plurality of beads can be functionalized with the species in a single batch.

A bead injected or otherwise introduced into a partition may comprise releasably, cleavably, or reversibly attached barcodes. A bead injected or otherwise introduced into a partition may comprise activatable barcodes. A bead injected or otherwise introduced into a partition may be degradable, disruptable, or dissolvable beads.

Barcodes can be releasably, cleavably or reversibly attached to the beads such that barcodes can be released or be releasable through cleavage of a linkage between the barcode molecule and the bead, or released through degradation of the underlying bead itself, allowing the barcodes to be accessed or be accessible by other reagents, or both. In non-limiting examples, cleavage may be achieved through reduction of di-sulfide bonds, use of restriction enzymes, photo-activated cleavage, or cleavage via other types of stimuli (e.g., chemical, thermal, pH, enzymatic, etc.) and/or reactions, such as described elsewhere herein. Releasable barcodes may sometimes be referred to as being activatable, in that they are available for reaction once released. Thus, for example, an activatable barcode may be activated by releasing the barcode from a bead (or other suitable type of partition described herein). Other activatable configurations are also envisioned in the context of the described methods and systems.

In addition to, or as an alternative to the cleavable linkages between the beads and the associated molecules, such as barcode containing nucleic acid molecules (e.g., barcoded oligonucleotides), the beads may be degradable, disruptable, or dissolvable spontaneously or upon exposure to one or more stimuli (e.g., temperature changes, pH changes, exposure to particular chemical species or phase, exposure to light, reducing agent, etc.). In some cases, a bead may be dissolvable, such that material components of the beads are solubilized when exposed to a particular chemical species or an environmental change, such as a change temperature or a change in pH. In some cases, a gel bead can be degraded or dissolved at elevated temperature and/or in basic conditions. In some cases, a bead may be thermally degradable such that when the bead is exposed to an appropriate change in temperature (e.g., heat), the bead degrades. Degradation or dissolution of a bead bound to a species (e.g., a nucleic acid molecule, e.g., barcoded oligonucleotide) may result in release of the species from the bead.

As will be appreciated from the above disclosure, the degradation of a bead may refer to the disassociation of a bound or entrained species from a bead, both with and without structurally degrading the physical bead itself. For example, the degradation of the bead may involve cleavage of a cleavable linkage via one or more species and/or methods described elsewhere herein. In another example, entrained species may be released from beads through osmotic pressure differences due to, for example, changing chemical environments. By way of example, alteration of bead pore sizes due to osmotic pressure differences can generally occur without structural degradation of the bead itself. In some cases, an increase in pore size due to osmotic swelling of a bead can permit the release of entrained species within the bead. In other cases, osmotic shrinking of a bead may cause a bead to better retain an entrained species due to pore size contraction.

A degradable bead may be introduced into a partition, such as a droplet of an emulsion or a well, such that the bead degrades within the partition and any associated species (e.g., oligonucleotides) are released within the droplet when the appropriate stimulus is applied. The free species (e.g., oligonucleotides, nucleic acid molecules) may interact with other reagents contained in the partition. For example, a polyacrylamide bead comprising cystamine and linked, via a disulfide bond, to a barcode sequence, may be combined with a reducing agent within a droplet of a water-in-oil emulsion. Within the droplet, the reducing agent can break the various disulfide bonds, resulting in bead degradation and release of the barcode sequence into the aqueous, inner environment of the droplet. In another example, heating of a droplet comprising a bead-bound barcode sequence in basic solution may also result in bead degradation and release of the attached barcode sequence into the aqueous, inner environment of the droplet.

Any suitable number of molecular tag molecules (e.g., primer, barcoded oligonucleotide) can be associated with a bead such that, upon release from the bead, the molecular tag molecules (e.g., primer, e.g., barcoded oligonucleotide) are present in the partition at a pre-defined concentration. Such pre-defined concentration may be selected to facilitate certain reactions for generating a sequencing library, e.g., amplification, within the partition. In some cases, the pre-defined concentration of the primer can be limited by the process of producing nucleic acid molecule (e.g., oligonucleotide) bearing beads.

In some cases, beads can be non-covalently loaded with one or more reagents. The beads can be non-covalently loaded by, for instance, subjecting the beads to conditions sufficient to swell the beads, allowing sufficient time for the reagents to diffuse into the interiors of the beads, and subjecting the beads to conditions sufficient to de-swell the beads. The swelling of the beads may be accomplished, for instance, by placing the beads in a thermodynamically favorable solvent, subjecting the beads to a higher or lower temperature, subjecting the beads to a higher or lower ion concentration, and/or subjecting the beads to an electric field. The swelling of the beads may be accomplished by various swelling methods. The de-swelling of the beads may be accomplished, for instance, by transferring the beads in a thermodynamically unfavorable solvent, subjecting the beads to lower or high temperatures, subjecting the beads to a lower or higher ion concentration, and/or removing an electric field. The de-swelling of the beads may be accomplished by various de-swelling methods. Transferring the beads may cause pores in the bead to shrink. The shrinking may then hinder reagents within the beads from diffusing out of the interiors of the beads. The hindrance may be due to steric interactions between the reagents and the interiors of the beads. The transfer may be accomplished microfluidically. For instance, the transfer may be achieved by moving the beads from one co-flowing solvent stream to a different co-flowing solvent stream. The swellability and/or pore size of the beads may be adjusted by changing the polymer composition of the bead.

In some cases, an acrydite moiety linked to a precursor, another species linked to a precursor, or a precursor itself can comprise a labile bond, such as chemically, thermally, or photo-sensitive bond e.g., disulfide bond, UV sensitive bond, or the like. Once acrydite moieties or other moieties comprising a labile bond are incorporated into a bead, the bead may also comprise the labile bond. The labile bond may be, for example, useful in reversibly linking (e.g., covalently linking) species (e.g., barcodes, primers, etc.) to a bead. In some cases, a thermally labile bond may include a nucleic acid hybridization based attachment, e.g., where an oligonucleotide is hybridized to a complementary sequence that is attached to the bead, such that thermal melting of the hybrid releases the oligonucleotide, e.g., a barcode containing sequence, from the bead or microcapsule.

The addition of multiple types of labile bonds to a gel bead may result in the generation of a bead capable of responding to varied stimuli. Each type of labile bond may be sensitive to an associated stimulus (e.g., chemical stimulus, light, temperature, enzymatic, etc.) such that release of species attached to a bead via each labile bond may be controlled by the application of the appropriate stimulus. Such functionality may be useful in controlled release of species from a gel bead. In some cases, another species comprising a labile bond may be linked to a gel bead after gel bead formation via, for example, an activated functional group of the gel bead as described above. As will be appreciated, barcodes that are releasably, cleavably or reversibly attached to the beads described herein include barcodes that are released or releasable through cleavage of a linkage between the barcode molecule and the bead, or that are released through degradation of the underlying bead itself, allowing the barcodes to be accessed or accessible by other reagents, or both.

The barcodes that are releasable as described herein may sometimes be referred to as being activatable, in that they are available for reaction once released. Thus, for example, an activatable barcode may be activated by releasing the barcode from a bead (or other suitable type of partition described herein). Other activatable configurations are also envisioned in the context of the described methods and systems.

In addition to thermally cleavable bonds, disulfide bonds and UV sensitive bonds, other non-limiting examples of labile bonds that may be coupled to a precursor or bead include an ester linkage (e.g., cleavable with an acid, a base, or hydroxylamine), a vicinal diol linkage (e.g., cleavable via sodium periodate), a Diels-Alder linkage (e.g., cleavable via heat), a sulfone linkage (e.g., cleavable via a base), a silyl ether linkage (e.g., cleavable via an acid), a glycosidic linkage (e.g., cleavable via an amylase), a peptide linkage (e.g., cleavable via a protease), or a phosphodiester linkage (e.g., cleavable via a nuclease (e.g., DNAase)). A bond may be cleavable via other nucleic acid molecule targeting enzymes, such as restriction enzymes (e.g., restriction endonucleases), as described further below.

Species may be encapsulated in beads during bead generation (e.g., during polymerization of precursors). Such species may or may not participate in polymerization. Such species may be entered into polymerization reaction mixtures such that generated beads comprise the species upon bead formation. In some cases, such species may be added to the gel beads after formation. Such species may include, for example, nucleic acid molecules (e.g., oligonucleotides), reagents for a nucleic acid amplification reaction (e.g., primers, polymerases, dNTPs, co-factors (e.g., ionic cofactors), buffers) including those described herein, reagents for enzymatic reactions (e.g., enzymes, co-factors, substrates, buffers), reagents for nucleic acid modification reactions such as polymerization, ligation, or digestion, and/or reagents for template preparation (e.g., tagmentation) for one or more sequencing platforms (e.g., Nextera® for Illumina®). Such species may include one or more enzymes described herein, including without limitation, polymerase, reverse transcriptase, restriction enzymes (e.g., endonuclease), transposase, ligase, proteinase K, DNAse, etc. Such species may include one or more reagents described elsewhere herein (e.g., lysis agents, inhibitors, inactivating agents, chelating agents, stimulus). Trapping of such species may be controlled by the polymer network density generated during polymerization of precursors, control of ionic charge within the gel bead (e.g., via ionic species linked to polymerized species), or by the release of other species. Encapsulated species may be released from a bead upon bead degradation and/or by application of a stimulus capable of releasing the species from the bead. Alternatively or in addition, species may be partitioned in a partition (e.g., droplet) during or subsequent to partition formation. Such species may include, without limitation, the abovementioned species that may also be encapsulated in a bead.

A degradable bead may comprise one or more species with a labile bond such that, when the bead/species is exposed to the appropriate stimuli, the bond is broken and the bead degrades. The labile bond may be a chemical bond (e.g., covalent bond, ionic bond) or may be another type of physical interaction (e.g., van der Waals interactions, dipole-dipole interactions, etc.). In some cases, a crosslinker used to generate a bead may comprise a labile bond. Upon exposure to the appropriate conditions, the labile bond can be broken and the bead degraded. For example, upon exposure of a polyacrylamide gel bead comprising cystamine crosslinkers to a reducing agent, the disulfide bonds of the cystamine can be broken and the bead degraded.

A degradable bead may be useful in more quickly releasing an attached species (e.g., a nucleic acid molecule, a barcode sequence, a primer, etc) from the bead when the appropriate stimulus is applied to the bead as compared to a bead that does not degrade. For example, for a species bound to an inner surface of a porous bead or in the case of an encapsulated species, the species may have greater mobility and accessibility to other species in solution upon degradation of the bead. In some cases, a species may also be attached to a degradable bead via a degradable linker (e.g., disulfide linker). The degradable linker may respond to the same stimuli as the degradable bead or the two degradable species may respond to different stimuli. For example, a barcode sequence may be attached, via a disulfide bond, to a polyacrylamide bead comprising cystamine. Upon exposure of the barcoded-bead to a reducing agent, the bead degrades and the barcode sequence is released upon breakage of both the disulfide linkage between the barcode sequence and the bead and the disulfide linkages of the cystamine in the bead.

As will be appreciated from the above disclosure, while referred to as degradation of a bead, in many instances as noted above, that degradation may refer to the disassociation of a bound or entrained species from a bead, both with and without structurally degrading the physical bead itself. For example, entrained species may be released from beads through osmotic pressure differences due to, for example, changing chemical environments. By way of example, alteration of bead pore sizes due to osmotic pressure differences can generally occur without structural degradation of the bead itself. In some cases, an increase in pore size due to osmotic swelling of a bead can permit the release of entrained species within the bead. In other cases, osmotic shrinking of a bead may cause a bead to better retain an entrained species due to pore size contraction.

Where degradable beads are provided, it may be beneficial to avoid exposing such beads to the stimulus or stimuli that cause such degradation prior to a given time, in order to, for example, avoid premature bead degradation and issues that arise from such degradation, including for example poor flow characteristics and aggregation. By way of example, where beads comprise reducible cross-linking groups, such as disulfide groups, it will be desirable to avoid contacting such beads with reducing agents, e.g., DTT or other disulfide cleaving reagents. In such cases, treatment to the beads described herein will, in some cases be provided free of reducing agents, such as DTT. Because reducing agents are often provided in commercial enzyme preparations, it may be desirable to provide reducing agent free (or DTT free) enzyme preparations in treating the beads described herein. Examples of such enzymes include, e.g., polymerase enzyme preparations, reverse transcriptase enzyme preparations, ligase enzyme preparations, as well as many other enzyme preparations that may be used to treat the beads described herein. The terms "reducing agent free" or "DTT free" preparations can refer to a preparation having less than about 1/10th, less than about 1/50th, or even less than about 1/100th of the lower ranges for such materials used in degrading the beads. For example, for DTT, the reducing agent free preparation can have less than about 0.01 millimolar (mM), 0.005 mM, 0.001 mM DTT, 0.0005 mM DTT, or even less than about 0.0001 mM DTT. In many cases, the amount of DTT can be undetectable.

Numerous chemical triggers may be used to trigger the degradation of beads. Examples of these chemical changes may include, but are not limited to pH-mediated changes to the integrity of a component within the bead, degradation of a component of a bead via cleavage of cross-linked bonds, and depolymerization of a component of a bead.

In some embodiments, a bead may be formed from materials that comprise degradable chemical crosslinkers, such as BAC or cystamine. Degradation of such degradable crosslinkers may be accomplished through a number of mechanisms. In some examples, a bead may be contacted with a chemical degrading agent that may induce oxidation, reduction or other chemical changes. For example, a chemical degrading agent may be a reducing agent, such as dithiothreitol (DTT). Additional examples of reducing agents may include β-mercaptoethanol, (2S)-2-amino-1,4-dimercaptobutane (dithiobutylamine or DTBA), tris(2-carboxyethyl)phosphine (TCEP), or combinations thereof. A reducing agent may degrade the disulfide bonds formed between gel precursors forming the bead, and thus, degrade the bead. In other cases, a change in pH of a solution, such as an increase in pH, may trigger degradation of a bead. In other cases, exposure to an aqueous solution, such as water, may trigger hydrolytic degradation, and thus degradation of the bead. In some cases, any combination of stimuli may trigger degradation of a bead. For example, a change in pH may enable a chemical agent (e.g., DTT) to become an effective reducing agent.

Beads may also be induced to release their contents upon the application of a thermal stimulus. A change in temperature can cause a variety of changes to a bead. For example, heat can cause a solid bead to liquefy. A change in heat may cause melting of a bead such that a portion of the bead degrades. In other cases, heat may increase the internal pressure of the bead components such that the bead ruptures or explodes. Heat may also act upon heat-sensitive polymers used as materials to construct beads.

Any suitable agent may degrade beads. In some embodiments, changes in temperature or pH may be used to degrade thermo-sensitive or pH-sensitive bonds within beads. In some embodiments, chemical degrading agents may be used to degrade chemical bonds within beads by oxidation, reduction or other chemical changes. For example, a chemical degrading agent may be a reducing agent, such as DTT, wherein DTT may degrade the disulfide bonds formed between a crosslinker and gel precursors, thus degrading the bead. In some embodiments, a reducing agent may be added to degrade the bead, which may or may not cause the bead to release its contents. Examples of reducing agents may include dithiothreitol (DTT), β-mercaptoethanol, (2S)-2-amino-1,4-dimercaptobutane (dithiobutylamine or DTBA), tris(2-carboxyethyl)phosphine (TCEP), or combinations thereof. The reducing agent may be present at a concentration of about 0.1 mM, 0.5 mM, 1 mM, 5 mM, 10 mM. The reducing agent may be present at a concentration of at least about 0.1 mM, 0.5 mM, 1 mM, 5 mM, 10 mM, or greater than 10 mM. The reducing agent may be present at concentration of at most about 10 mM, 5 mM, 1 mM, 0.5 mM, 0.1 mM, or less.

Any suitable number of molecular tag molecules (e.g., primer, barcoded oligonucleotide) can be associated with a bead such that, upon release from the bead, the molecular tag molecules (e.g., primer, e.g., barcoded oligonucleotide) are present in the partition at a pre-defined concentration. Such pre-defined concentration may be selected to facilitate certain reactions for generating a sequencing library, e.g., amplification, within the partition. In some cases, the pre-defined concentration of the primer can be limited by the process of producing oligonucleotide bearing beads.

Although FIG. 1 and FIG. 2 have been described in terms of providing substantially singly occupied partitions, above, in certain cases, it may be desirable to provide multiply occupied partitions, e.g., containing two, three, four or more cells and/or microcapsules (e.g., beads) comprising barcoded nucleic acid molecules (e.g., oligonucleotides) within a single partition. Accordingly, as noted above, the flow characteristics of the biological particle and/or bead containing fluids and partitioning fluids may be controlled to provide for such multiply occupied partitions. In particular, the flow parameters may be controlled to provide a given occupancy rate at greater than about 50% of the partitions, greater than about 75%, and in some cases greater than about 80%, 90%, 95%, or higher.

In some cases, additional microcapsules can be used to deliver additional reagents to a partition. In such cases, it may be advantageous to introduce different beads into a common channel or droplet generation junction, from different bead sources (e.g., containing different associated reagents) through different channel inlets into such common channel or droplet generation junction (e.g., junction 210). In such cases, the flow and frequency of the different beads into the channel or junction may be controlled to provide for a certain ratio of microcapsules from each source, while ensuring a given pairing or combination of such beads into a partition with a given number of biological particles (e.g., one biological particle and one bead per partition).

The partitions described herein may comprise small volumes, for example, less than about 10 microliters (µL), 5 µL, 1 µL, 900 picoliters (µL), 800 pL, 700 pL, 600 pL, 500 pL, 400 pL, 300 pL, 200 pL, 100 pL, 50 pL, 20 pL, 10 pL, 1 pL, 500 nanoliters (nL), 100 nL, 50 nL, or less.

For example, in the case of droplet based partitions, the droplets may have overall volumes that are less than about 1000 pL, 900 pL, 800 pL, 700 pL, 600 pL, 500 pL, 400 pL, 300 pL, 200 pL, 100 pL, 50 pL, 20 pL, 10 pL, 1 pL, or less. Where co-partitioned with microcapsules, it will be appreciated that the sample fluid volume, e.g., including co-partitioned biological particles and/or beads, within the partitions may be less than about 90% of the above described volumes, less than about 80%, less than about 70%, less than about 60%, less than about 50%, less than about 40%, less than about 30%, less than about 20%, or less than about 10% of the above described volumes.

As is described elsewhere herein, partitioning species may generate a population or plurality of partitions. In such cases, any suitable number of partitions can be generated or otherwise provided. For example, at least about 1,000 partitions, at least about 5,000 partitions, at least about 10,000 partitions, at least about 50,000 partitions, at least about 100,000 partitions, at least about 500,000 partitions, at least about 1,000,000 partitions, at least about 5,000,000 partitions, at least about 10,000,000 partitions, at least about 50,000,000 partitions, at least about 100,000,000 partitions, at least about 500,000,000 partitions, at least about 1,000,000,000 partitions, or more partitions can be generated or otherwise provided. Moreover, the plurality of partitions may comprise both unoccupied partitions (e.g., empty partitions) and occupied partitions.

Reagents

In accordance with certain aspects, biological particles may be partitioned along with lysis reagents in order to release the contents of the biological particles within the partition. In such cases, the lysis agents can be contacted with the biological particle suspension concurrently with, or immediately prior to, the introduction of the biological particles into the partitioning junction/droplet generation zone (e.g., junction 210), such as through an additional channel or channels upstream of the channel junction. In accordance with other aspects, additionally or alternatively, biological particles may be partitioned along with other reagents, as will be described further below.

Figure 3:
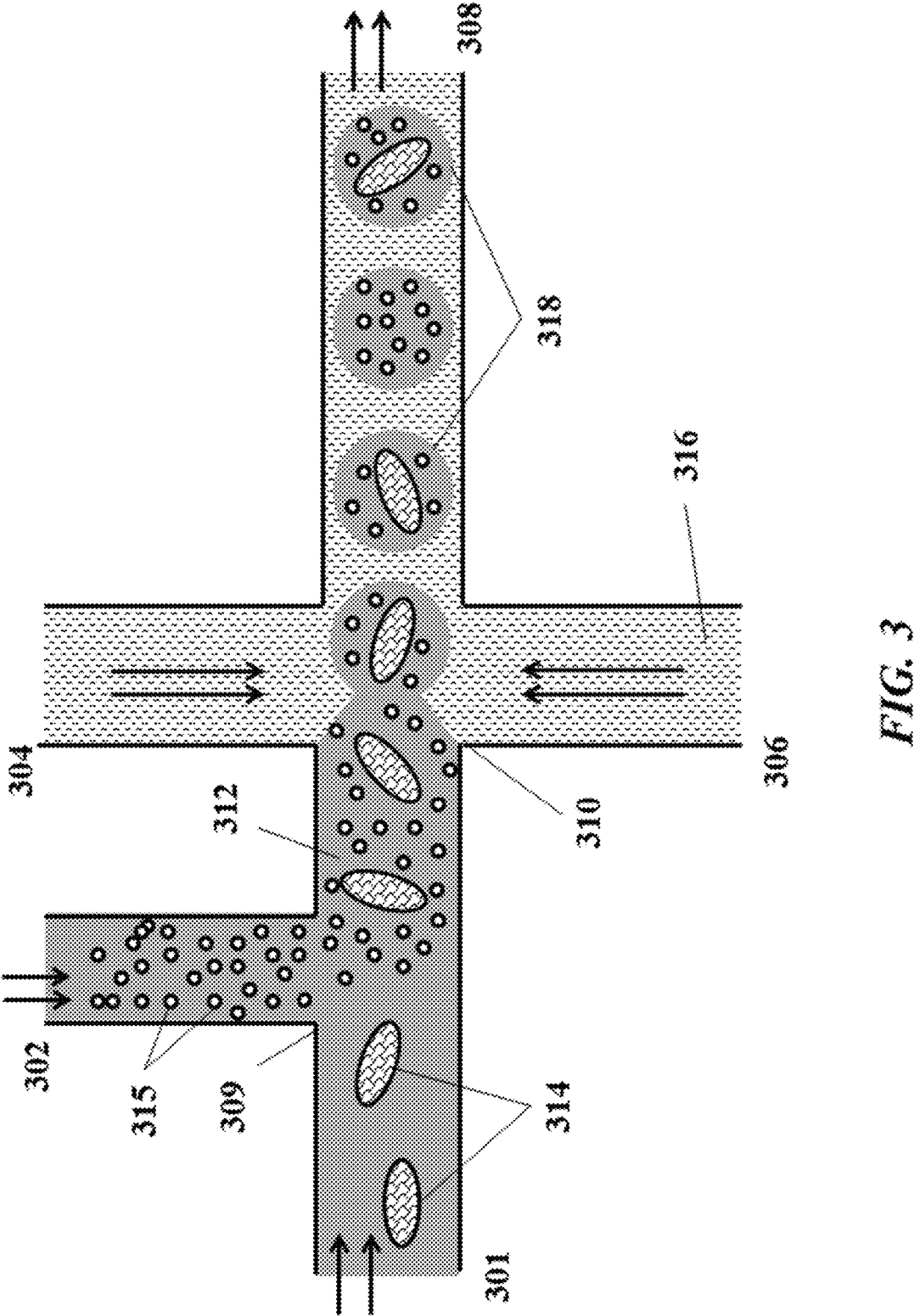
FIG. 3 shows an example of a microfluidic channel structure for co-partitioning biological particles and reagents.

FIG. 3 shows an example of a microfluidic channel structure 300 for co-partitioning biological particles and reagents. The channel structure 300 can include channel segments 301, 302, 304, 306 and 308. Channel segments 301 and 302 communicate at a first channel junction 309. Channel segments 302, 304, 306, and 308 communicate at a second channel junction 310.

In an example operation, the channel segment 301 may transport an aqueous fluid 312 that includes a plurality of biological particles 314 along the channel segment 301 into the second junction 310. As an alternative or in addition to, channel segment 301 may transport beads (e.g., gel beads). The beads may comprise barcode molecules.

For example, the channel segment 301 may be connected to a reservoir comprising an aqueous suspension of biological particles 314. Upstream of, and immediately prior to reaching, the second junction 310, the channel segment 301 may meet the channel segment 302 at the first junction 309. The channel segment 302 may transport a plurality of reagents 315 (e.g., lysis agents) suspended in the aqueous fluid 312 along the channel segment 302 into the first junction 309. For example, the channel segment 302 may be connected to a reservoir comprising the reagents 315. After the first junction 309, the aqueous fluid 312 in the channel segment 301 can carry both the biological particles 314 and the reagents 315 towards the second junction 310. In some instances, the aqueous fluid 312 in the channel segment 301 can include one or more reagents, which can be the same or different reagents as the reagents 315. A second fluid 316 that is immiscible with the aqueous fluid 312 (e.g., oil) can be delivered to the second junction 310 from each of channel segments 304 and 306. Upon meeting of the aqueous fluid 312 from the channel segment 301 and the second fluid 316 from each of channel segments 304 and 306 at the second channel junction 310, the aqueous fluid 312 can be partitioned as discrete droplets 318 in the second fluid 316 and flow away from the second junction 310 along channel segment 308. The channel segment 308 may deliver the discrete droplets 318 to an outlet reservoir fluidly coupled to the channel segment 308, where they may be harvested.

The second fluid 316 can comprise an oil, such as a fluorinated oil, that includes a fluorosurfactant for stabilizing the resulting droplets, for example, inhibiting subsequent coalescence of the resulting droplets 318.

A discrete droplet generated may include an individual biological particle 314 and/or one or more reagents 315. In some instances, a discrete droplet generated may include a barcode carrying bead (not shown), such as via other microfluidics structures described elsewhere herein. In some instances, a discrete droplet may be unoccupied (e.g., no reagents, no biological particles).

Beneficially, when lysis reagents and biological particles are co-partitioned, the lysis reagents can facilitate the release of the contents of the biological particles within the partition. The contents released in a partition may remain discrete from the contents of other partitions.

As will be appreciated, the channel segments described herein may be coupled to any of a variety of different fluid sources or receiving components, including reservoirs, tubing, manifolds, or fluidic components of other systems. As will be appreciated, the microfluidic channel structure 300 may have other geometries. For example, a microfluidic channel structure can have more than two channel junctions. For example, a microfluidic channel structure can have 2, 3, 4, 5 channel segments or more each carrying the same or different types of beads, reagents, and/or biological particles that meet at a channel junction. Fluid flow in each channel segment may be controlled to control the partitioning of the different elements into droplets. Fluid may be directed flow along one or more channels or reservoirs via one or more fluid flow units. A fluid flow unit can comprise compressors (e.g., providing positive pressure), pumps (e.g., providing negative pressure), actuators, and the like to control flow of the fluid. Fluid may also or otherwise be controlled via applied pressure differentials, centrifugal force, electrokinetic pumping, vacuum, capillary or gravity flow, or the like.

Examples of lysis agents include bioactive reagents, such as lysis enzymes that are used for lysis of different cell types, e.g., gram positive or negative bacteria, plants, yeast, mammalian, etc., such as lysozymes, achromopeptidase, lysostaphin, labiase, kitalase, lyticase, and a variety of other lysis enzymes available from, e.g., Sigma-Aldrich, Inc. (St Louis, MO), as well as other commercially available lysis enzymes. Other lysis agents may additionally or alternatively be co-partitioned with the biological particles to cause the release of the biological particle's contents into the partitions. For example, in some cases, surfactant-based lysis solutions may be used to lyse cells, although these may be less desirable for emulsion based systems where the surfactants can interfere with stable emulsions. In some cases, lysis solutions may include non-ionic surfactants such as, for example, TritonX-100 and Tween 20. In some cases, lysis solutions may include ionic surfactants such as, for example, sarcosyl and sodium dodecyl sulfate (SDS). Electroporation, thermal, acoustic or mechanical cellular disruption may also be used in certain cases, e.g., non-emulsion based partitioning such as encapsulation of biological particles that may be in addition to or in place of droplet partitioning, where any pore size of the encapsulate is sufficiently small to retain nucleic acid fragments of a given size, following cellular disruption.

Alternatively or in addition to the lysis agents co-partitioned with the biological particles described above, other reagents can also be co-partitioned with the biological particles, including, for example, DNase and RNase inactivating agents or inhibitors, such as proteinase K, chelating agents, such as EDTA, and other reagents employed in removing or otherwise reducing negative activity or impact of different cell lysate components on subsequent processing of nucleic acids. In addition, in the case of encapsulated biological particles, the biological particles may be exposed to an appropriate stimulus to release the biological particles or their contents from a co-partitioned microcapsule. For example, in some cases, a chemical stimulus may be co-partitioned along with an encapsulated biological particle to allow for the degradation of the microcapsule and release of the cell or its contents into the larger partition. In some cases, this stimulus may be the same as the stimulus described elsewhere herein for release of nucleic acid molecules (e.g., oligonucleotides) from their respective microcapsule (e.g., bead). In alternative aspects, this may be a different and non-overlapping stimulus, in order to allow an encapsulated biological particle to be released into a partition at a different time from the release of nucleic acid molecules into the same partition.

Additional reagents may also be co-partitioned with the biological particles, such as endonucleases to fragment a biological particle's DNA, DNA polymerase enzymes and dNTPs used to amplify the biological particle's nucleic acid fragments and to attach the barcode molecular tags to the amplified fragments. Other enzymes may be co-partitioned, including without limitation, polymerase, transposase, ligase, proteinase K, DNAse, etc. Additional reagents may also include reverse transcriptase enzymes, including enzymes with terminal transferase activity, primers and oligonucleotides, and switch oligonucleotides (also referred to herein as "switch oligos" or "template switching oligonucleotides") which can be used for template switching. In some cases, template switching can be used to increase the length of a cDNA. In some cases, template switching can be used to append a predefined nucleic acid sequence to the cDNA. In an example of template switching, cDNA can be generated from reverse transcription of a template, e.g., cellular mRNA, where a reverse transcriptase with terminal transferase activity can add additional nucleotides, e.g., polyC, to the cDNA in a template independent manner. Switch oligos can include sequences complementary to the additional nucleotides, e.g., polyG. The additional nucleotides (e.g., polyC) on the cDNA can hybridize to the additional nucleotides (e.g., polyG) on the switch oligo, whereby the switch oligo can be used by the reverse transcriptase as template to further extend the cDNA. Template switching oligonucleotides may comprise a hybridization region and a template region. The hybridization region can comprise any sequence capable of hybridizing to the target. In some cases, as previously described, the hybridization region comprises a series of G bases to complement the overhanging C bases at the 3' end of a cDNA molecule. The series of G bases may comprise 1 G base, 2 G bases, 3 G bases, 4 G bases, 5 G bases or more than 5 G bases. The template sequence can comprise any sequence to be incorporated into the cDNA. In some cases, the template region comprises at least 1 (e.g., at least 2, 3, 4, 5 or more) tag sequences and/or functional sequences. Switch oligos may comprise deoxyribonucleic acids; ribonucleic acids; modified nucleic acids including 2-Aminopurine, 2,6-Diaminopurine (2-Amino-dA), inverted dT, 5-Methyl dC, 2'-deoxyInosine, Super T (5-hydroxybutynl-2'-deoxyuridine), Super G (8-aza-7-deazaguanosine), locked nucleic acids (LNAs), unlocked nucleic acids (UNAs, e.g., UNA-A, UNA-U, UNA-C, UNA-G), Iso-dG, Iso-dC, 2' Fluoro bases (e.g., Fluoro C, Fluoro U, Fluoro A, and Fluoro G), or any combination.

In some cases, the length of a switch oligo may be at least about 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249 or 250 nucleotides or longer.

In some cases, the length of a switch oligo may be at most about 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249 or 250 nucleotides.

Once the contents of the cells are released into their respective partitions, the macromolecular components (e.g., macromolecular constituents of biological particles, such as RNA, DNA, or proteins) contained therein may be further processed within the partitions. In accordance with the methods and systems described herein, the macromolecular component contents of individual biological particles can be provided with unique identifiers such that, upon characterization of those macromolecular components they may be attributed as having been derived from the same biological particle or particles. The ability to attribute characteristics to individual biological particles or groups of biological particles is provided by the assignment of unique identifiers specifically to an individual biological particle or groups of biological particles. Unique identifiers, e.g., in the form of nucleic acid barcodes can be assigned or associated with individual biological particles or populations of biological particles, in order to tag or label the biological particle's macromolecular components (and as a result, its characteristics) with the unique identifiers. These unique identifiers can then be used to attribute the biological particle's components and characteristics to an individual biological particle or group of biological particles.

In some aspects, this is performed by co-partitioning the individual biological particle or groups of biological particles with the unique identifiers, such as described above (with reference to FIG. 2). In some aspects, the unique identifiers are provided in the form of nucleic acid molecules (e.g., oligonucleotides) that comprise nucleic acid barcode sequences that may be attached to or otherwise associated with the nucleic acid contents of individual biological particle, or to other components of the biological particle, and particularly to fragments of those nucleic acids. The nucleic acid molecules are partitioned such that as between nucleic acid molecules in a given partition, the nucleic acid barcode sequences contained therein are the same, but as between different partitions, the nucleic acid molecule can, and do have differing barcode sequences, or at least represent a large number of different barcode sequences across all of the partitions in a given analysis. In some aspects, only one nucleic acid barcode sequence can be associated with a given partition, although in some cases, two or more different barcode sequences may be present.

The nucleic acid barcode sequences can include from about 6 to about 20 or more nucleotides within the sequence of the nucleic acid molecules (e.g., oligonucleotides). The nucleic acid barcode sequences can include from about 6 to about 20, 30, 40, 50, 60, 70, 80, 90, 100 or more nucleotides. In some cases, the length of a barcode sequence may be about 6, 7, 8, 9, 10, 11, 12, 13, 14, 15, 16, 17, 18, 19, 20 nucleotides or longer. In some cases, the length of a barcode sequence may be at least about 6, 7, 8, 9, 10, 11, 12, 13, 14, 15, 16, 17, 18, 19, 20 nucleotides or longer. In some cases, the length of a barcode sequence may be at most about 6, 7, 8, 9, 10, 11, 12, 13, 14, 15, 16, 17, 18, 19, 20 nucleotides or shorter. These nucleotides may be completely contiguous, i.e., in a single stretch of adjacent nucleotides, or they may be separated into two or more separate subsequences that are separated by 1 or more nucleotides. In some cases, separated barcode subsequences can be from about 4 to about 16 nucleotides in length. In some cases, the barcode subsequence may be about 4, 5, 6, 7, 8, 9, 10, 11, 12, 13, 14, 15, 16 nucleotides or longer. In some cases, the barcode subsequence may be at least about 4, 5, 6, 7, 8, 9, 10, 11, 12, 13, 14, 15, 16 nucleotides or longer. In some cases, the barcode subsequence may be at most about 4, 5, 6, 7, 8, 9, 10, 11, 12, 13, 14, 15, 16 nucleotides or shorter.

The co-partitioned nucleic acid molecules can also comprise other functional sequences useful in the processing of the nucleic acids from the co-partitioned biological particles. These sequences include, e.g., targeted or random/universal amplification primer sequences for amplifying the genomic DNA from the individual biological particles within the partitions while attaching the associated barcode sequences, sequencing primers or primer recognition sites, hybridization or probing sequences, e.g., for identification of presence of the sequences or for pulling down barcoded nucleic acids, or any of a number of other potential functional sequences. Other mechanisms of co-partitioning oligonucleotides may also be employed, including, e.g., coalescence of two or more droplets, where one droplet contains oligonucleotides, or microdispensing of oligonucleotides into partitions, e.g., droplets within microfluidic systems.

In an example, microcapsules, such as beads, are provided that each include large numbers of the above described barcoded nucleic acid molecules (e.g., barcoded oligonucleotides) releasably attached to the beads, where all of the nucleic acid molecules attached to a particular bead will include the same nucleic acid barcode sequence, but where a large number of diverse barcode sequences are represented across the population of beads used. In some embodiments, hydrogel beads, e.g., comprising polyacrylamide polymer matrices, are used as a solid support and delivery vehicle for the nucleic acid molecules into the partitions, as they are capable of carrying large numbers of nucleic acid molecules, and may be configured to release those nucleic acid molecules upon exposure to a particular stimulus, as described elsewhere herein. In some cases, the population of beads provides a diverse barcode sequence library that includes at least about 1,000 different barcode sequences, at least about 5,000 different barcode sequences, at least about 10,000 different barcode sequences, at least about 50,000 different barcode sequences, at least about 100,000 different barcode sequences, at least about 1,000,000 different barcode sequences, at least about 5,000,000 different barcode sequences, or at least about 10,000,000 different barcode sequences, or more. Additionally, each bead can be provided with large numbers of nucleic acid (e.g., oligonucleotide) molecules attached. In particular, the number of molecules of nucleic acid molecules including the barcode sequence on an individual bead can be at least about 1,000 nucleic acid molecules, at least about 5,000 nucleic acid molecules, at least about 10,000 nucleic acid molecules, at least about 50,000 nucleic acid molecules, at least about 100,000 nucleic acid molecules, at least about 500,000 nucleic acids, at least about 1,000,000 nucleic acid molecules, at least about 5,000,000 nucleic acid molecules, at least about 10,000,000 nucleic acid molecules, at least about 50,000, 000 nucleic acid molecules, at least about 100,000,000 nucleic acid molecules, at least about 250,000,000 nucleic acid molecules and in some cases at least about 1 billion nucleic acid molecules, or more. Nucleic acid molecules of a given bead can include identical (or common) barcode sequences, different barcode sequences, or a combination of both. Nucleic acid molecules of a given bead can include multiple sets of nucleic acid molecules. Nucleic acid molecules of a given set can include identical barcode sequences. The identical barcode sequences can be different from barcode sequences of nucleic acid molecules of another set.

Moreover, when the population of beads is partitioned, the resulting population of partitions can also include a diverse barcode library that includes at least about 1,000 different barcode sequences, at least about 5,000 different barcode sequences, at least about 10,000 different barcode sequences, at least at least about 50,000 different barcode sequences, at least about 100,000 different barcode sequences, at least about 1,000,000 different barcode sequences, at least about 5,000,000 different barcode sequences, or at least about 10,000,000 different barcode sequences. Additionally, each partition of the population can include at least about 1,000 nucleic acid molecules, at least about 5,000 nucleic acid molecules, at least about 10,000 nucleic acid molecules, at least about 50,000 nucleic acid molecules, at least about 100,000 nucleic acid molecules, at least about 500,000 nucleic acids, at least about 1,000,000 nucleic acid molecules, at least about 5,000,000 nucleic acid molecules, at least about 10,000,000 nucleic acid molecules, at least about 50,000,000 nucleic acid molecules, at least about 100,000,000 nucleic acid molecules, at least about 250,000,000 nucleic acid molecules and in some cases at least about 1 billion nucleic acid molecules.

In some cases, it may be desirable to incorporate multiple different barcodes within a given partition, either attached to a single or multiple beads within the partition. For example, in some cases, a mixed, but known set of barcode sequences may provide greater assurance of identification in the subsequent processing, e.g., by providing a stronger address or attribution of the barcodes to a given partition, as a duplicate or independent confirmation of the output from a given partition.

The nucleic acid molecules (e.g., oligonucleotides) are releasable from the beads upon the application of a particular stimulus to the beads. In some cases, the stimulus may be a photo-stimulus, e.g., through cleavage of a photo-labile linkage that releases the nucleic acid molecules. In other cases, a thermal stimulus may be used, where elevation of the temperature of the beads environment will result in cleavage of a linkage or other release of the nucleic acid molecules from the beads. In still other cases, a chemical stimulus can be used that cleaves a linkage of the nucleic acid molecules to the beads, or otherwise results in release of the nucleic acid molecules from the beads. In one case, such compositions include the polyacrylamide matrices described above for encapsulation of biological particles, and may be degraded for release of the attached nucleic acid molecules through exposure to a reducing agent, such as DTT.

In some aspects, provided are systems and methods for controlled partitioning. Droplet size may be controlled by adjusting certain geometric features in channel architecture (e.g., microfluidics channel architecture). For example, an expansion angle, width, and/or length of a channel may be adjusted to control droplet size.

Figure 4:
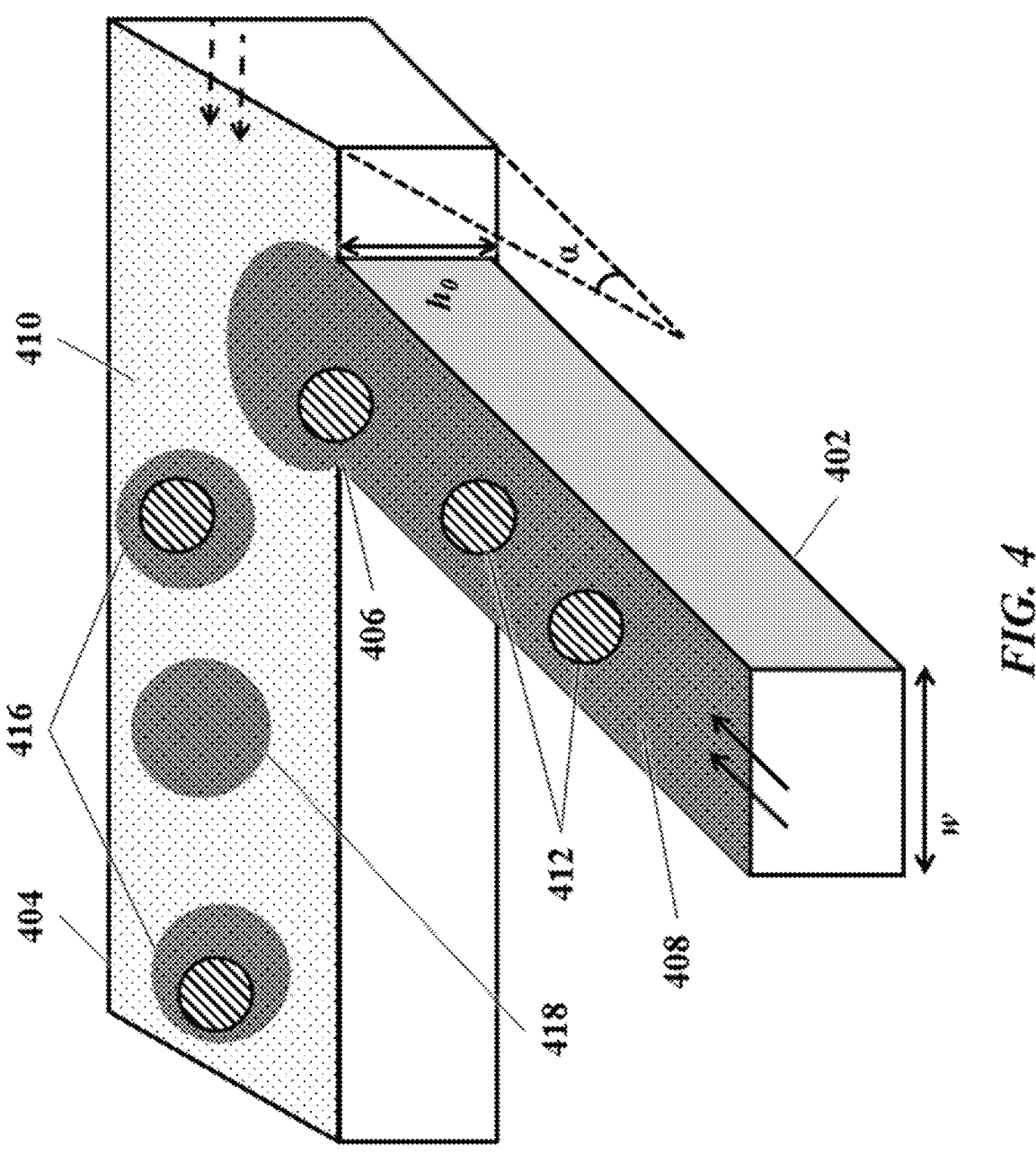
FIG. 4 shows an example of a microfluidic channel structure for the controlled partitioning of beads into discrete droplets.

FIG. 4 shows an example of a microfluidic channel structure for the controlled partitioning of beads into discrete droplets. A channel structure 400 can include a channel segment 402 communicating at a channel junction 406 (or intersection) with a reservoir 404. The reservoir 404 can be a chamber. Any reference to "reservoir," as used herein, can also refer to a "chamber." In operation, an aqueous fluid 408 that includes suspended beads 412 may be transported along the channel segment 402 into the junction 406 to meet a second fluid 410 that is immiscible with the aqueous fluid 408 in the reservoir 404 to create droplets 416, 418 of the aqueous fluid 408 flowing into the reservoir 404. At the junction 406 where the aqueous fluid 408 and the second fluid 410 meet, droplets can form based on factors such as the hydrodynamic forces at the junction 406, flow rates of the two fluids 408, 410, fluid properties, and certain geometric parameters (e.g., w, $h_0$, α, etc.) of the channel structure 400. A plurality of droplets can be collected in the reservoir 404 by continuously injecting the aqueous fluid 408 from the channel segment 402 through the junction 406.

A discrete droplet generated may include a bead (e.g., as in occupied droplets 416). Alternatively, a discrete droplet generated may include more than one bead. Alternatively, a discrete droplet generated may not include any beads (e.g., as in unoccupied droplet 418). In some instances, a discrete droplet generated may contain one or more biological particles, as described elsewhere herein. In some instances, a discrete droplet generated may comprise one or more reagents, as described elsewhere herein.

In some instances, the aqueous fluid 408 can have a substantially uniform concentration or frequency of beads 412. The beads 412 can be introduced into the channel segment 402 from a separate channel (not shown in FIG. 4). The frequency of beads 412 in the channel segment 402 may be controlled by controlling the frequency in which the beads 412 are introduced into the channel segment 402 and/or the relative flow rates of the fluids in the channel segment 402 and the separate channel. In some instances, the beads can be introduced into the channel segment 402 from a plurality of different channels, and the frequency controlled accordingly.

In some instances, the aqueous fluid 408 in the channel segment 402 can comprise biological particles (e.g., described with reference to FIGS. 1 and 2). In some instances, the aqueous fluid 408 can have a substantially uniform concentration or frequency of biological particles. As with the beads, the biological particles can be introduced into the channel segment 402 from a separate channel. The frequency or concentration of the biological particles in the aqueous fluid 408 in the channel segment 402 may be controlled by controlling the frequency in which the biological particles are introduced into the channel segment 402 and/or the relative flow rates of the fluids in the channel segment 402 and the separate channel. In some instances, the biological particles can be introduced into the channel segment 402 from a plurality of different channels, and the frequency controlled accordingly. In some instances, a first separate channel can introduce beads and a second separate channel can introduce biological particles into the channel segment 402. The first separate channel introducing the beads may be upstream or downstream of the second separate channel introducing the biological particles.

The second fluid 410 can comprise an oil, such as a fluorinated oil, that includes a fluorosurfactant for stabilizing the resulting droplets, for example, inhibiting subsequent coalescence of the resulting droplets.

In some instances, the second fluid 410 may not be subjected to and/or directed to any flow in or out of the reservoir 404. For example, the second fluid 410 may be substantially stationary in the reservoir 404. In some instances, the second fluid 410 may be subjected to flow within the reservoir 404, but not in or out of the reservoir 404, such as via application of pressure to the reservoir 404 and/or as affected by the incoming flow of the aqueous fluid

408 at the junction 406. Alternatively, the second fluid 410 may be subjected and/or directed to flow in or out of the reservoir 404. For example, the reservoir 404 can be a channel directing the second fluid 410 from upstream to downstream, transporting the generated droplets.

The channel structure 400 at or near the junction 406 may have certain geometric features that at least partly determine the sizes of the droplets formed by the channel structure 400. The channel segment 402 can have a height, $h_0$ and width, w, at or near the junction 406. By way of example, the channel segment 402 can comprise a rectangular cross-section that leads to a reservoir 404 having a wider cross-section (such as in width or diameter). Alternatively, the cross-section of the channel segment 402 can be other shapes, such as a circular shape, trapezoidal shape, polygonal shape, or any other shapes. The top and bottom walls of the reservoir 404 at or near the junction 406 can be inclined at an expansion angle, a. The expansion angle, a, allows the tongue (portion of the aqueous fluid 408 leaving channel segment 402 at junction 406 and entering the reservoir 404 before droplet formation) to increase in depth and facilitate decrease in curvature of the intermediately formed droplet. Droplet size may decrease with increasing expansion angle. The resulting droplet radius, $R_d$, may be predicted by the following equation for the aforementioned geometric parameters of $h_0$, w, and α:

$$R_d \approx 0.44\left(1 + 2.2\sqrt{\tan \alpha}\,\frac{w}{h_0}\right)\frac{h_0}{\sqrt{\tan \alpha}}$$

By way of example, for a channel structure with w=21 μm, h=21 μm, and α=3°, the predicted droplet size is 121 μm. In another example, for a channel structure with w=25 μm, h=25 μm, and α=5°, the predicted droplet size is 123 μm. In another example, for a channel structure with w=28 μm, h=28 μm, and α=7°, the predicted droplet size is 124 μm.

In some instances, the expansion angle, a, may be between a range of from about 0.5° to about 4°, from about 0.1° to about 10°, or from about 0° to about 90°. For example, the expansion angle can be at least about 0.01°, 0.1°, 0.2°, 0.3°, 0.4°, 0.5°, 0.6°, 0.7°, 0.8°, 0.9°, 1°, 2°, 3°, 4°, 5°, 6°, 7°, 8°, 9°, 10°, 15°, 20°, 25°, 30°, 35°, 40°, 45°, 50°, 55°, 60°, 65°, 70°, 75°, 80°, 85°, or higher. In some instances, the expansion angle can be at most about 89°, 88°, 87°, 86°, 85°, 84°, 83°, 82°, 81°, 80°, 75°, 70°, 65°, 60°, 55°, 50°, 45°, 40°, 35°, 30°, 25°, 20°, 15°, 10°, 9°, 8°, 7°, 6°, 5°, 4°, 3°, 2°, 1°, 0.1°, 0.01°, or less. In some instances, the width, w, can be between a range of from about 100 micrometers (μm) to about 500 μm. In some instances, the width, w, can be between a range of from about 10 μm to about 200 μm. Alternatively, the width can be less than about 10 μm. Alternatively, the width can be greater than about 500 μm. In some instances, the flow rate of the aqueous fluid 408 entering the junction 406 can be between about 0.04 microliters (μL)/minute (min) and about 40 L/min. In some instances, the flow rate of the aqueous fluid 408 entering the junction 406 can be between about 0.01 microliters (μL)/minute (min) and about 100 μL/min. Alternatively, the flow rate of the aqueous fluid 408 entering the junction 406 can be less than about 0.01 μL/min. Alternatively, the flow rate of the aqueous fluid 408 entering the junction 406 can be greater than about 40 μL/min, such as 45 μL/min, 50 μL/min, 55 μL/min, 60 μL/min, 65 μL/min, 70 μL/min, 75 μL/min, 80 μL/min, 85 μL/min, 90 μL/min, 95 μL/min, 100 μL/min, 110 μL/min, 120 μL/min, 130 μL/min, 140 μL/min, 150 μL/min, or greater. At lower flow rates, such as flow rates of about less than or equal to 10 microliters/minute, the droplet radius may not be dependent on the flow rate of the aqueous fluid 408 entering the junction 406.

In some instances, at least about 50% of the droplets generated can have uniform size. In some instances, at least about 55%, 60%, 65%, 70%, 75%, 80%, 85%, 90%, 95%, 96%, 97%, 98%, 99%, or greater of the droplets generated can have uniform size. Alternatively, less than about 50% of the droplets generated can have uniform size.

The throughput of droplet generation can be increased by increasing the points of generation, such as increasing the number of junctions (e.g., junction 406) between aqueous fluid 408 channel segments (e.g., channel segment 402) and the reservoir 404. Alternatively or in addition, the throughput of droplet generation can be increased by increasing the flow rate of the aqueous fluid 408 in the channel segment 402.

Figure 5:
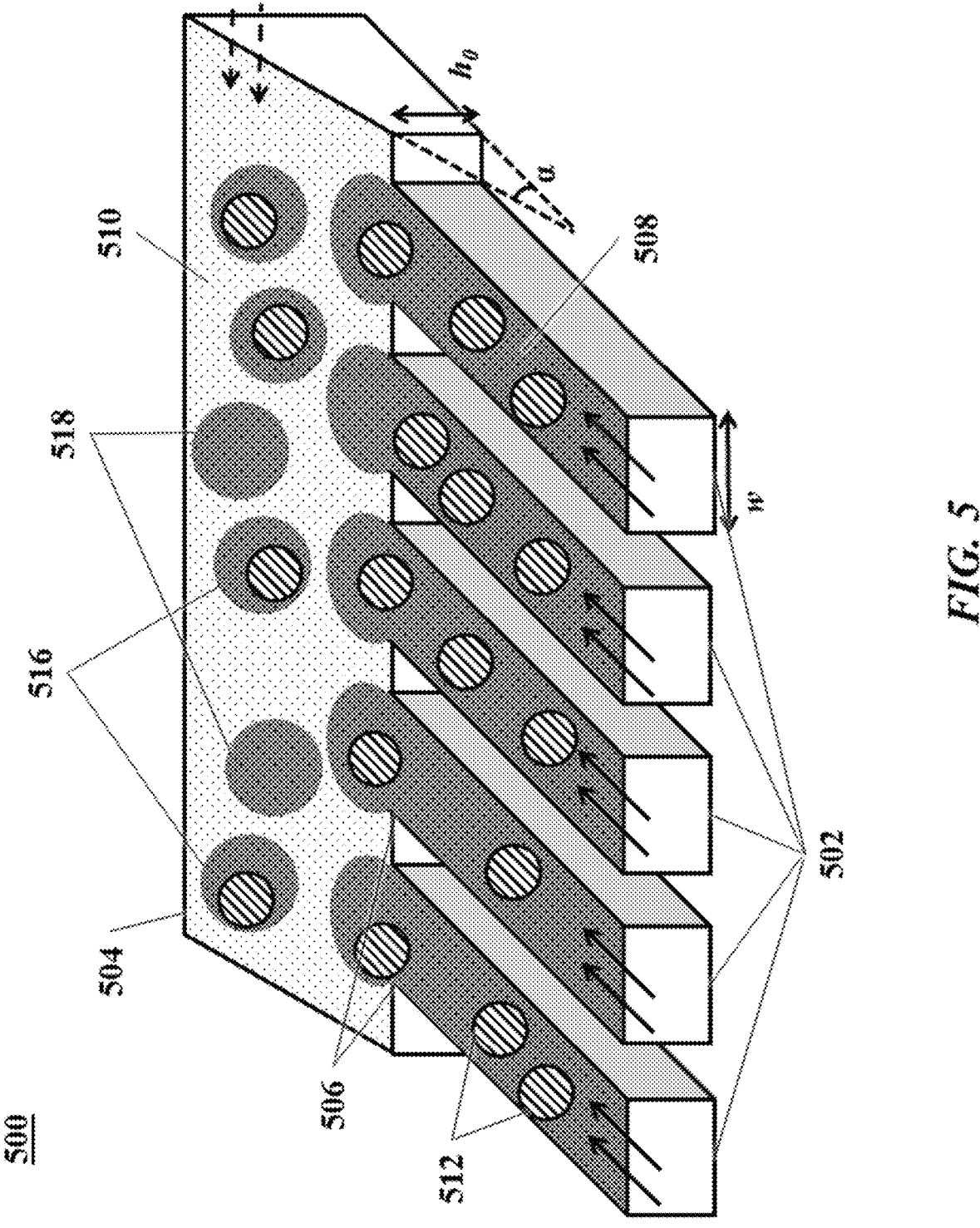
FIG. 5 shows an example of a microfluidic channel structure for increased droplet generation throughput.

FIG. 5 shows an example of a microfluidic channel structure for increased droplet generation throughput. A microfluidic channel structure 500 can comprise a plurality of channel segments 502 and a reservoir 504. Each of the plurality of channel segments 502 may be in fluid communication with the reservoir 504. The channel structure 500 can comprise a plurality of channel junctions 506 between the plurality of channel segments 502 and the reservoir 504. Each channel junction can be a point of droplet generation. The channel segment 402 from the channel structure 400 in FIG. 4 and any description to the components thereof may correspond to a given channel segment of the plurality of channel segments 502 in channel structure 500 and any description to the corresponding components thereof. The reservoir 404 from the channel structure 400 and any description to the components thereof may correspond to the reservoir 504 from the channel structure 500 and any description to the corresponding components thereof.

Each channel segment of the plurality of channel segments 502 may comprise an aqueous fluid 508 that includes suspended beads 512. The reservoir 504 may comprise a second fluid 510 that is immiscible with the aqueous fluid 508. In some instances, the second fluid 510 may not be subjected to and/or directed to any flow in or out of the reservoir 504. For example, the second fluid 510 may be substantially stationary in the reservoir 504. In some instances, the second fluid 510 may be subjected to flow within the reservoir 504, but not in or out of the reservoir 504, such as via application of pressure to the reservoir 504 and/or as affected by the incoming flow of the aqueous fluid 508 at the junctions. Alternatively, the second fluid 510 may be subjected and/or directed to flow in or out of the reservoir 504. For example, the reservoir 504 can be a channel directing the second fluid 510 from upstream to downstream, transporting the generated droplets.

In operation, the aqueous fluid 508 that includes suspended beads 512 may be transported along the plurality of channel segments 502 into the plurality of junctions 506 to meet the second fluid 510 in the reservoir 504 to create droplets 516, 518. A droplet may form from each channel segment at each corresponding junction with the reservoir 504. At the junction where the aqueous fluid 508 and the second fluid 510 meet, droplets can form based on factors such as the hydrodynamic forces at the junction, flow rates of the two fluids 508, 510, fluid properties, and certain geometric parameters (e.g., w, $h_0$, α, etc.) of the channel structure 500, as described elsewhere herein. A plurality of droplets can be collected in the reservoir 504 by continuously injecting the aqueous fluid 508 from the plurality of channel segments 502 through the plurality of junctions 506. Throughput may significantly increase with the parallel channel configuration of channel structure 500. For example, a channel structure having five inlet channel segments comprising the aqueous fluid 508 may generate droplets five times as frequently than a channel structure having one inlet channel segment, provided that the fluid flow rate in the channel segments are substantially the same. The fluid flow rate in the different inlet channel segments may or may not be substantially the same. A channel structure may have as many parallel channel segments as is practical and allowed for the size of the reservoir. For example, the channel structure may have at least about 2, 3, 4, 5, 6, 7, 8, 9, 10, 20, 30, 40, 50, 60, 70, 80, 90, 100, 150, 500, 250, 300, 350, 400, 450, 500, 600, 700, 800, 900, 1000, 1500, 5000 or more parallel or substantially parallel channel segments.

The geometric parameters, w, $h_0$, and α, may or may not be uniform for each of the channel segments in the plurality of channel segments 502. For example, each channel segment may have the same or different widths at or near its respective channel junction with the reservoir 504. For example, each channel segment may have the same or different height at or near its respective channel junction with the reservoir 504. In another example, the reservoir 504 may have the same or different expansion angle at the different channel junctions with the plurality of channel segments 502. When the geometric parameters are uniform, beneficially, droplet size may also be controlled to be uniform even with the increased throughput. In some instances, when it is desirable to have a different distribution of droplet sizes, the geometric parameters for the plurality of channel segments 502 may be varied accordingly.

In some instances, at least about 50% of the droplets generated can have uniform size. In some instances, at least about 55%, 60%, 65%, 70%, 75%, 80%, 85%, 90%, 95%, 96%, 97%, 98%, 99%, or greater of the droplets generated can have uniform size. Alternatively, less than about 50% of the droplets generated can have uniform size.

Figure 6:
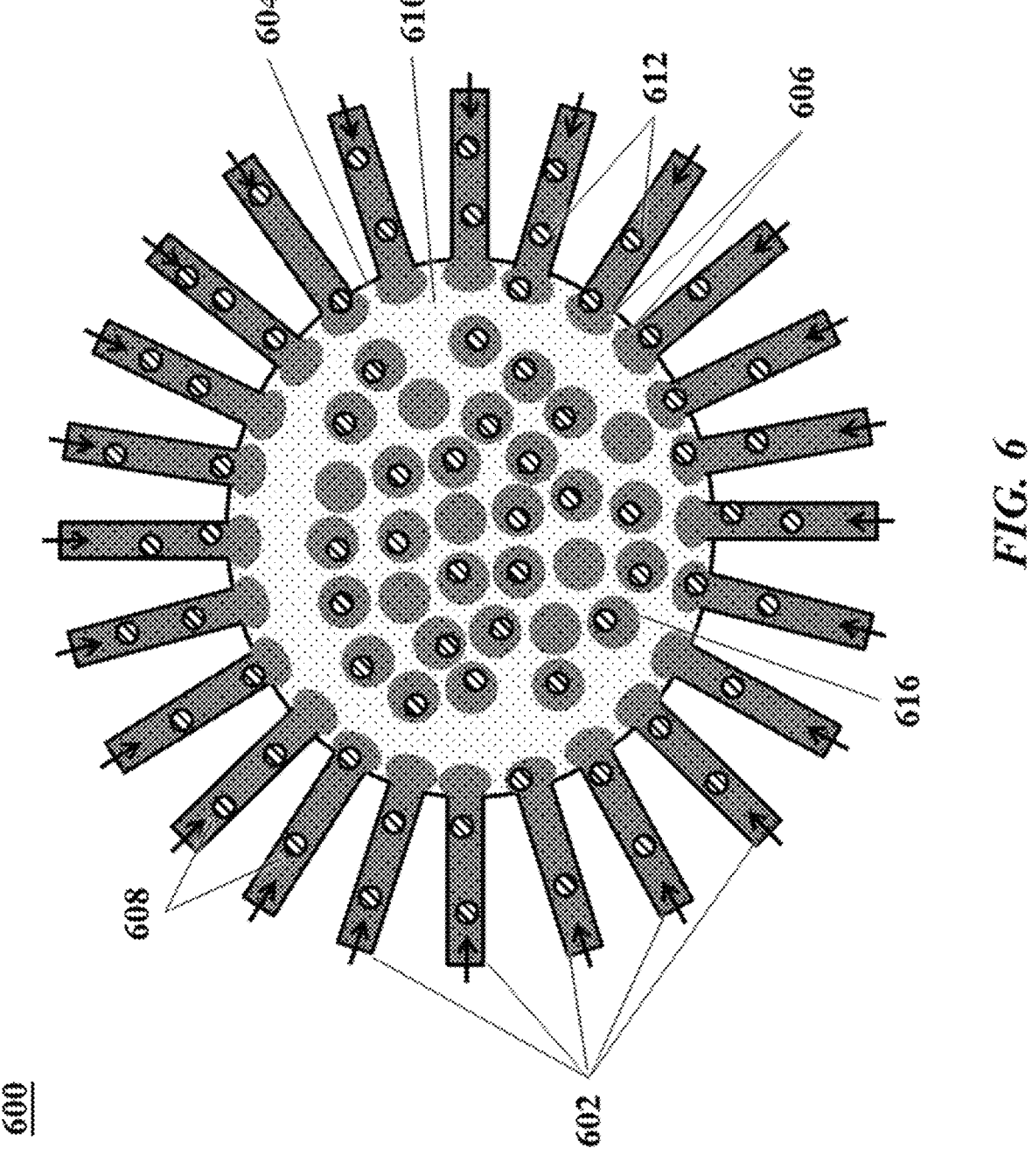
FIG. 6 shows another example of a microfluidic channel structure for increased droplet generation throughput.

FIG. 6 shows another example of a microfluidic channel structure for increased droplet generation throughput. A microfluidic channel structure 600 can comprise a plurality of channel segments 602 arranged generally circularly around the perimeter of a reservoir 604. Each of the plurality of channel segments 602 may be in fluid communication with the reservoir 604. The channel structure 600 can comprise a plurality of channel junctions 606 between the plurality of channel segments 602 and the reservoir 604. Each channel junction can be a point of droplet generation. The channel segment 402 from the channel structure 400 in FIG. 4 and any description to the components thereof may correspond to a given channel segment of the plurality of channel segments 602 in channel structure 600 and any description to the corresponding components thereof. The reservoir 404 from the channel structure 400 and any description to the components thereof may correspond to the reservoir 604 from the channel structure 600 and any description to the corresponding components thereof.

Each channel segment of the plurality of channel segments 602 may comprise an aqueous fluid 608 that includes suspended beads 612. The reservoir 604 may comprise a second fluid 610 that is immiscible with the aqueous fluid 608. In some instances, the second fluid 610 may not be subjected to and/or directed to any flow in or out of the reservoir 604. For example, the second fluid 610 may be substantially stationary in the reservoir 604. In some instances, the second fluid 610 may be subjected to flow within the reservoir 604, but not in or out of the reservoir 604, such as via application of pressure to the reservoir 604 and/or as affected by the incoming flow of the aqueous fluid 608 at the junctions. Alternatively, the second fluid 610 may be subjected and/or directed to flow in or out of the reservoir 604. For example, the reservoir 604 can be a channel directing the second fluid 610 from upstream to downstream, transporting the generated droplets.

In operation, the aqueous fluid 608 that includes suspended beads 612 may be transported along the plurality of channel segments 602 into the plurality of junctions 606 to meet the second fluid 610 in the reservoir 604 to create a plurality of droplets 616. A droplet may form from each channel segment at each corresponding junction with the reservoir 604. At the junction where the aqueous fluid 608 and the second fluid 610 meet, droplets can form based on factors such as the hydrodynamic forces at the junction, flow rates of the two fluids 608, 610, fluid properties, and certain geometric parameters (e.g., widths and heights of the channel segments 602, expansion angle of the reservoir 604, etc.) of the channel structure 600, as described elsewhere herein. A plurality of droplets can be collected in the reservoir 604 by continuously injecting the aqueous fluid 608 from the plurality of channel segments 602 through the plurality of junctions 606. Throughput may significantly increase with the substantially parallel channel configuration of the channel structure 600. A channel structure may have as many substantially parallel channel segments as is practical and allowed for by the size of the reservoir. For example, the channel structure may have at least about 2, 3, 4, 5, 6, 7, 8, 9, 10, 20, 30, 40, 50, 60, 70, 80, 90, 100, 150, 200, 250, 300, 350, 400, 450, 500, 600, 700, 800, 900, 1000, 1500, 5000 or more parallel or substantially parallel channel segments. The plurality of channel segments may be substantially evenly spaced apart, for example, around an edge or perimeter of the reservoir. Alternatively, the spacing of the plurality of channel segments may be uneven.

The reservoir 604 may have an expansion angle, a (not shown in FIG. 6) at or near each channel junction. Each channel segment of the plurality of channel segments 602 may have a width, w, and a height, $h_0$, at or near the channel junction. The geometric parameters, w, $h_0$, and α, may or may not be uniform for each of the channel segments 602. For example, each channel segment may have the same or different widths at or near its respective channel junction with the reservoir 604. For example, each channel segment may have the same or different height at or near its respective channel junction with the reservoir 604.

The reservoir 604 may have the same or different expansion angle at the different channel junctions with the plurality of channel segments 602. For example, a circular reservoir (as shown in FIG. 6) may have a conical, dome-like, or hemispherical ceiling (e.g., top wall) to provide the same or substantially same expansion angle for each channel segments 602 at or near the plurality of channel junctions 606. When the geometric parameters are uniform, beneficially, resulting droplet size may be controlled to be uniform even with the increased throughput. In some instances, when it is desirable to have a different distribution of droplet sizes, the geometric parameters for the plurality of channel segments 602 may be varied accordingly.

In some instances, at least about 50% of the droplets generated can have uniform size. In some instances, at least about 55%, 60%, 65%, 70%, 75%, 80%, 85%, 90%, 95%, 96%, 97%, 98%, 99%, or greater of the droplets generated can have uniform size. Alternatively, less than about 50% of the droplets generated can have uniform size. The beads and/or biological particle injected into the droplets may or may not have uniform size.

Figures 7A, 7B:
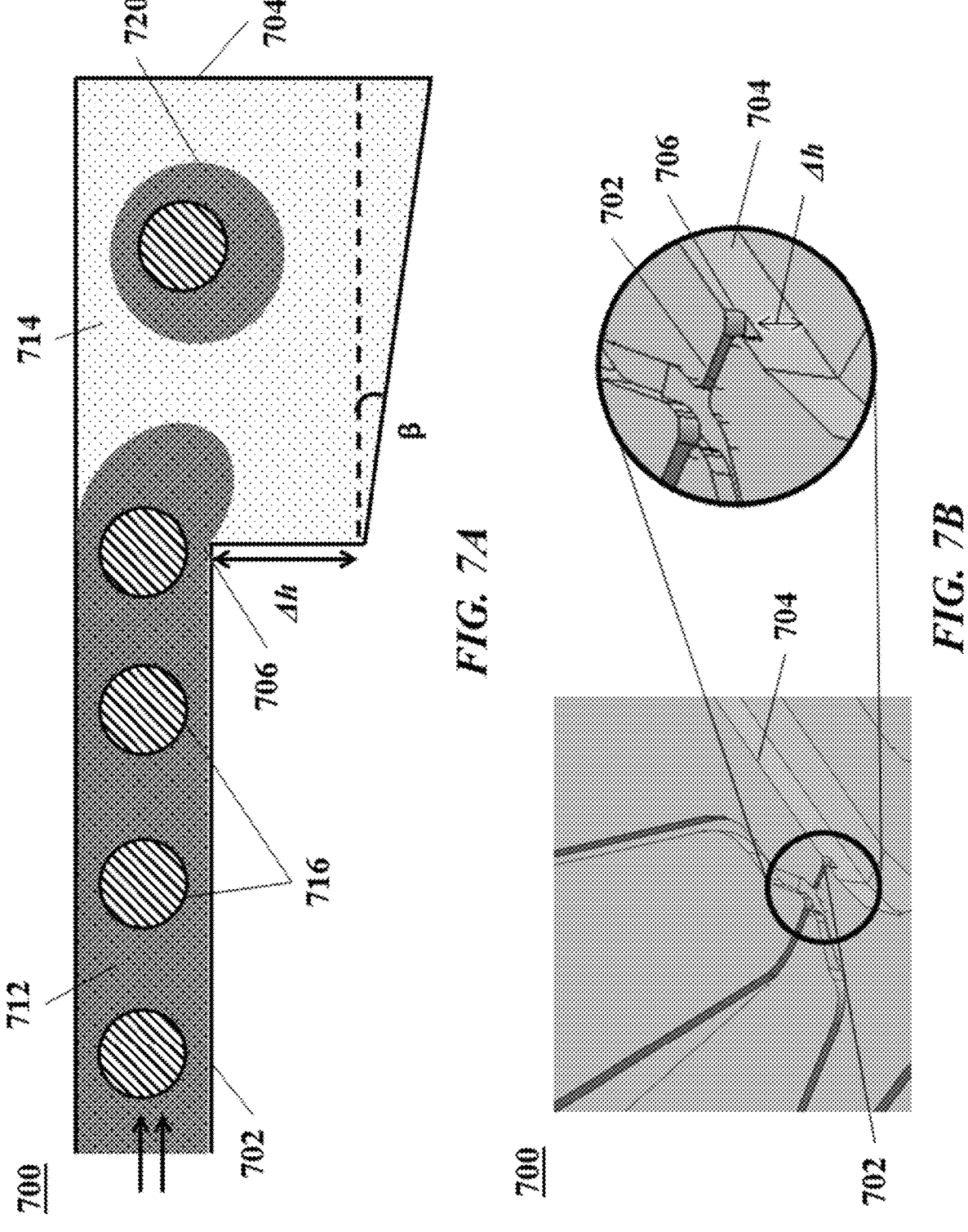
FIG. 7A shows a cross-section view of another example of a microfluidic channel structure with a geometric feature for controlled partitioning.
FIG. 7B shows a perspective view of the channel structure of FIG. 7A.

FIG. 7A shows a cross-section view of another example of a microfluidic channel structure with a geometric feature for controlled partitioning. A channel structure 700 can include a channel segment 702 communicating at a channel junction 706 (or intersection) with a reservoir 704. In some instances, the channel structure 700 and one or more of its components can correspond to the channel structure 100 and one or more of its components. FIG. 7B shows a perspective view of the channel structure 700 of FIG. 7A.

An aqueous fluid 712 comprising a plurality of particles 716 may be transported along the channel segment 702 into the junction 706 to meet a second fluid 714 (e.g., oil, etc.) that is immiscible with the aqueous fluid 712 in the reservoir 704 to create droplets 720 of the aqueous fluid 712 flowing into the reservoir 704. At the junction 706 where the aqueous fluid 712 and the second fluid 714 meet, droplets can form based on factors such as the hydrodynamic forces at the junction 706, relative flow rates of the two fluids 712, 714, fluid properties, and certain geometric parameters (e.g., 4h, etc.) of the channel structure 700. A plurality of droplets can be collected in the reservoir 704 by continuously injecting the aqueous fluid 712 from the channel segment 702 at the junction 706.

A discrete droplet generated may comprise one or more particles of the plurality of particles 716. As described elsewhere herein, a particle may be any particle, such as a bead, cell bead, gel bead, biological particle, macromolecular constituents of biological particle, or other particles. Alternatively, a discrete droplet generated may not include any particles.

In some instances, the aqueous fluid 712 can have a substantially uniform concentration or frequency of particles 716. As described elsewhere herein (e.g., with reference to FIG. 4), the particles 716 (e.g., beads) can be introduced into the channel segment 702 from a separate channel (not shown in FIG. 7). The frequency of particles 716 in the channel segment 702 may be controlled by controlling the frequency in which the particles 716 are introduced into the channel segment 702 and/or the relative flow rates of the fluids in the channel segment 702 and the separate channel. In some instances, the particles 716 can be introduced into the channel segment 702 from a plurality of different channels, and the frequency controlled accordingly. In some instances, different particles may be introduced via separate channels. For example, a first separate channel can introduce beads and a second separate channel can introduce biological particles into the channel segment 702. The first separate channel introducing the beads may be upstream or downstream of the second separate channel introducing the biological particles.

In some instances, the second fluid 714 may not be subjected to and/or directed to any flow in or out of the reservoir 704. For example, the second fluid 714 may be substantially stationary in the reservoir 704. In some instances, the second fluid 714 may be subjected to flow within the reservoir 704, but not in or out of the reservoir 704, such as via application of pressure to the reservoir 704 and/or as affected by the incoming flow of the aqueous fluid 712 at the junction 706. Alternatively, the second fluid 714 may be subjected and/or directed to flow in or out of the reservoir 704. For example, the reservoir 704 can be a channel directing the second fluid 714 from upstream to downstream, transporting the generated droplets.

The channel structure 700 at or near the junction 706 may have certain geometric features that at least partly determine the sizes and/or shapes of the droplets formed by the channel structure 700. The channel segment 702 can have a first cross-section height, $h_1$, and the reservoir 704 can have a second cross-section height, $h_2$. The first cross-section height, $h_1$, and the second cross-section height, $h_2$, may be different, such that at the junction 706, there is a height difference of $\Delta h$. The second cross-section height, $h_2$, may be greater than the first cross-section height, $h_1$. In some instances, the reservoir may thereafter gradually increase in cross-section height, for example, the more distant it is from the junction 706. In some instances, the cross-section height of the reservoir may increase in accordance with expansion angle, $\beta$, at or near the junction 706. The height difference, $\Delta h$, and/or expansion angle, $\delta$, can allow the tongue (portion of the aqueous fluid 712 leaving channel segment 702 at junction 706 and entering the reservoir 704 before droplet formation) to increase in depth and facilitate decrease in curvature of the intermediately formed droplet. For example, droplet size may decrease with increasing height difference and/or increasing expansion angle.

The height difference, $\Delta h$, can be at least about 1 μm. Alternatively, the height difference can be at least about 1, 2, 3, 4, 5, 6, 7, 8, 9, 10, 11, 12, 13, 14, 15, 16, 17, 18, 19, 20, 25, 30, 35, 40, 45, 50, 60, 70, 80, 90, 100, 200, 300, 400, 500 μm or more. Alternatively, the height difference can be at most about 500, 400, 300, 200, 100, 90, 80, 70, 60, 50, 45, 40, 35, 30, 25, 20, 19, 18, 17, 16, 15, 14, 13, 12, 11, 10, 9, 8, 7, 6, 5, 4, 3, 2, 1 μm or less. In some instances, the expansion angle, $\beta$, may be between a range of from about 0.5° to about 4°, from about 0.1° to about 10°, or from about 0° to about 90°. For example, the expansion angle can be at least about 0.01°, 0.1°, 0.2°, 0.3°, 0.4°, 0.5°, 0.6°, 0.7°, 0.8°, 0.9°, 1°, 2°, 3°, 4°, 5°, 6°, 7°, 8°, 9°, 10°, 15°, 20°, 25°, 30°, 35°, 40°, 45°, 50°, 55°, 60°, 65°, 70°, 75°, 80°, 85°, or higher. In some instances, the expansion angle can be at most about 89°, 88°, 87°, 86°, 85°, 84°, 83°, 82°, 81°, 80°, 75°, 70°, 65°, 60°, 55°, 50°, 45°, 40°, 35°, 30°, 25°, 20°, 15°, 10°, 9°, 8°, 7°, 6°, 5°, 4°, 3°, 2°, 1°, 0.1°, 0.01°, or less.

In some instances, the flow rate of the aqueous fluid 712 entering the junction 706 can be between about 0.04 microliters (μL)/minute (min) and about 40 μL/min. In some instances, the flow rate of the aqueous fluid 712 entering the junction 706 can be between about 0.01 microliters (μL)/minute (min) and about 100 μL/min. Alternatively, the flow rate of the aqueous fluid 712 entering the junction 706 can be less than about 0.01 L/min. Alternatively, the flow rate of the aqueous fluid 712 entering the junction 706 can be greater than about 40 L/min, such as 45 μL/min, 50 μL/min, 55 μL/min, 60 L/min, 65 μL/min, 70 μL/min, 75 μL/min, 80 μL/min, 85 μL/min, 90 μL/min, 95 μL/min, 100 μL/min, 110 μL/min, 120 L/min, 130 μL/min, 140 μL/min, 150 μL/min, or greater. At lower flow rates, such as flow rates of about less than or equal to 10 microliters/minute, the droplet radius may not be dependent on the flow rate of the aqueous fluid 712 entering the junction 706. The second fluid 714 may be stationary, or substantially stationary, in the reservoir 704. Alternatively, the second fluid 714 may be flowing, such as at the above flow rates described for the aqueous fluid 712.

In some instances, at least about 50% of the droplets generated can have uniform size. In some instances, at least about 55%, 60%, 65%, 70%, 75%, 80%, 85%, 90%, 95%, 96%, 97%, 98%, 99%, or greater of the droplets generated can have uniform size. Alternatively, less than about 50% of the droplets generated can have uniform size.

While FIGS. 7A and 7B illustrate the height difference, $\Delta h$, being abrupt at the junction 706 (e.g., a step increase), the height difference may increase gradually (e.g., from about 0 μm to a maximum height difference). Alternatively, the height difference may decrease gradually (e.g., taper) from a maximum height difference. A gradual increase or decrease in height difference, as used herein, may refer to a continuous incremental increase or decrease in height difference, wherein an angle between any one differential segment of a height profile and an immediately adjacent differential segment of the height profile is greater than 90°. For example, at the junction 706, a bottom wall of the channel and a bottom wall of the reservoir can meet at an angle greater than 90°. Alternatively or in addition, a top wall (e.g., ceiling) of the channel and a top wall (e.g., ceiling) of the reservoir can meet an angle greater than 90°. A gradual increase or decrease may be linear or non-linear (e.g., exponential, sinusoidal, etc.). Alternatively or in addition, the height difference may variably increase and/or decrease linearly or non-linearly. While FIGS. 7A and 7B illustrate the expanding reservoir cross-section height as linear (e.g., constant expansion angle, $\beta$), the cross-section height may expand non-linearly. For example, the reservoir may be defined at least partially by a dome-like (e.g., hemispherical) shape having variable expansion angles. The cross-section height may expand in any shape.

The channel networks, e.g., as described above or elsewhere herein, can be fluidly coupled to appropriate fluidic components. For example, the inlet channel segments are fluidly coupled to appropriate sources of the materials they are to deliver to a channel junction. These sources may include any of a variety of different fluidic components, from simple reservoirs defined in or connected to a body structure of a microfluidic device, to fluid conduits that deliver fluids from off-device sources, manifolds, fluid flow units (e.g., actuators, pumps, compressors) or the like. Likewise, the outlet channel segment (e.g., channel segment 208, reservoir 604, etc.) may be fluidly coupled to a receiving vessel or conduit for the partitioned cells for subsequent processing. Again, this may be a reservoir defined in the body of a microfluidic device, or it may be a fluidic conduit for delivering the partitioned cells to a subsequent process operation, instrument or component.

The methods and systems described herein may be used to greatly increase the efficiency of single cell applications and/or other applications receiving droplet-based input. For example, following the sorting of occupied cells and/or appropriately-sized cells, subsequent operations that can be performed can include generation of amplification products, purification (e.g., via solid phase reversible immobilization (SPRI)), further processing (e.g., shearing, ligation of functional sequences, and subsequent amplification (e.g., via PCR)). These operations may occur in bulk (e.g., outside the partition). In the case where a partition is a droplet in an emulsion, the emulsion can be broken and the contents of the droplet pooled for additional operations. Additional reagents that may be co-partitioned along with the barcode bearing bead may include oligonucleotides to block ribosomal RNA (rRNA) and nucleases to digest genomic DNA from cells. Alternatively, rRNA removal agents may be applied during additional processing operations. The configuration of the constructs generated by such a method can help minimize (or avoid) sequencing of the poly-T sequence during sequencing and/or sequence the 5' end of a polynucleotide sequence. The amplification products, for example, first amplification products and/or second amplification products, may be subject to sequencing for sequence analysis. In some cases, amplification may be performed using the Partial Hairpin Amplification for Sequencing (PHASE) method.

A variety of applications require the evaluation of the presence and quantification of different biological particle or organism types within a population of biological particles, including, for example, microbiome analysis and characterization, environmental testing, food safety testing, epidemiological analysis, e.g., in tracing contamination or the like.

Computer Systems

Figure 12:
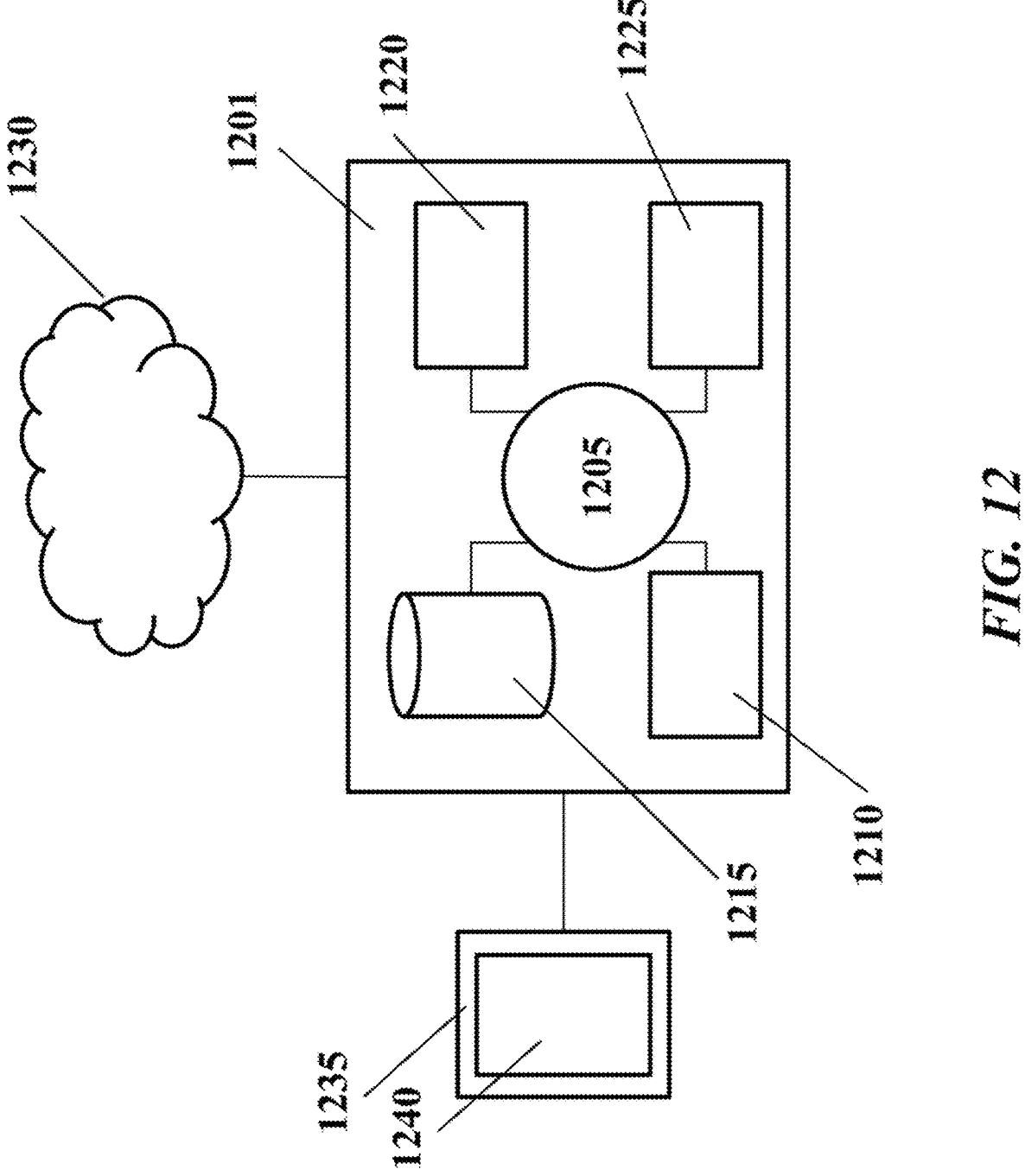
FIG. 12 shows a computer system that is programmed or otherwise configured to implement methods provided herein.

The present disclosure provides computer systems that are programmed to implement methods of the disclosure. FIG. 12 shows a computer system 1201 that is programmed or otherwise configured to measure and receive, and/or control instructions for detecting, one or more signals corresponding to a fluorescent tag from a nucleic acid probe, process such signals, and/or determine one or more parameters or characteristics of a bead, a partition, or otherwise a partition occupant. The computer system 1201 can regulate various aspects of the present disclosure. The computer system 1201 can be an electronic device of a user or a computer system that is remotely located with respect to the electronic device. The electronic device can be a mobile electronic device.

The computer system 1201 includes a central processing unit (CPU, also "processor" and "computer processor" herein) 1205, which can be a single core or multi core processor, or a plurality of processors for parallel processing. The computer system 1201 also includes memory or memory location 1210 (e.g., random-access memory, read-only memory, flash memory), electronic storage unit 1215 (e.g., hard disk), communication interface 1220 (e.g., network adapter) for communicating with one or more other systems, and peripheral devices 1225, such as cache, other memory, data storage and/or electronic display adapters. The memory 1210, storage unit 1215, interface 1220 and peripheral devices 1225 are in communication with the CPU 1205 through a communication bus (solid lines), such as a motherboard. The storage unit 1215 can be a data storage unit (or data repository) for storing data. The computer system 1201 can be operatively coupled to a computer network ("network") 1230 with the aid of the communication interface 1220. The network 1230 can be the Internet, an internet and/or extranet, or an intranet and/or extranet that is in communication with the Internet. The network 1230 in some cases is a telecommunication and/or data network. The network 1230 can include one or more computer servers, which can enable distributed computing, such as cloud computing. The network 1230, in some cases with the aid of the computer system 1201, can implement a peer-to-peer network, which may enable devices coupled to the computer system 1201 to behave as a client or a server.

The CPU 1205 can execute a sequence of machine-readable instructions, which can be embodied in a program or software. The instructions may be stored in a memory location, such as the memory 1210. The instructions can be directed to the CPU 1205, which can subsequently program or otherwise configure the CPU 1205 to implement methods of the present disclosure. Examples of operations performed by the CPU 1205 can include fetch, decode, execute, and writeback.

The CPU 1205 can be part of a circuit, such as an integrated circuit. One or more other components of the system 1201 can be included in the circuit. In some cases, the circuit is an application specific integrated circuit (ASIC).

The storage unit 1215 can store files, such as drivers, libraries and saved programs. The storage unit 1215 can store user data, e.g., user preferences and user programs. The computer system 1201 in some cases can include one or more additional data storage units that are external to the computer system 1201, such as located on a remote server that is in communication with the computer system 1201 through an intranet or the Internet.

The computer system 1201 can communicate with one or more remote computer systems through the network 1230. For instance, the computer system 1201 can communicate with a remote computer system of a user (e.g., operator). Examples of remote computer systems include personal computers (e.g., portable PC), slate or tablet PC's (e.g., Apple® iPad, Samsung® Galaxy Tab), telephones, Smart phones (e.g., Apple® iphone, Android-enabled device, Blackberry®), or personal digital assistants. The user can access the computer system 1201 via the network 1230.

Methods as described herein can be implemented by way of machine (e.g., computer processor) executable code stored on an electronic storage location of the computer system 1201, such as, for example, on the memory 1210 or electronic storage unit 1215. The machine executable or machine readable code can be provided in the form of software. During use, the code can be executed by the processor 1205. In some cases, the code can be retrieved from the storage unit 1215 and stored on the memory 1210 for ready access by the processor 1205. In some situations, the electronic storage unit 1215 can be precluded, and machine-executable instructions are stored on memory 1210.

The code can be pre-compiled and configured for use with a machine having a processor adapted to execute the code, or can be compiled during runtime. The code can be supplied in a programming language that can be selected to enable the code to execute in a pre-compiled or as-compiled fashion.

Aspects of the systems and methods provided herein, such as the computer system 1201, can be embodied in programming. Various aspects of the technology may be thought of as "products" or "articles of manufacture" typically in the form of machine (or processor) executable code and/or associated data that is carried on or embodied in a type of machine readable medium. Machine-executable code can be stored on an electronic storage unit, such as memory (e.g., read-only memory, random-access memory, flash memory) or a hard disk. "Storage" type media can include any or all of the tangible memory of the computers, processors or the like, or associated modules thereof, such as various semiconductor memories, tape drives, disk drives and the like, which may provide non-transitory storage at any time for the software programming. All or portions of the software may at times be communicated through the Internet or various other telecommunication networks. Such communications, for example, may enable loading of the software from one computer or processor into another, for example, from a management server or host computer into the computer platform of an application server. Thus, another type of media that may bear the software elements includes optical, electrical and electromagnetic waves, such as used across physical interfaces between local devices, through wired and optical landline networks and over various air-links. The physical elements that carry such waves, such as wired or wireless links, optical links or the like, also may be considered as media bearing the software. As used herein, unless restricted to non-transitory, tangible "storage" media, terms such as computer or machine "readable medium" refer to any medium that participates in providing instructions to a processor for execution.

Hence, a machine readable medium, such as computer-executable code, may take many forms, including but not limited to, a tangible storage medium, a carrier wave medium or physical transmission medium. Non-volatile storage media include, for example, optical or magnetic disks, such as any of the storage devices in any computer(s) or the like, such as may be used to implement the databases, etc. shown in the drawings. Volatile storage media include dynamic memory, such as main memory of such a computer platform. Tangible transmission media include coaxial cables; copper wire and fiber optics, including the wires that comprise a bus within a computer system. Carrier-wave transmission media may take the form of electric or electromagnetic signals, or acoustic or light waves such as those generated during radio frequency (RF) and infrared (IR) data communications. Common forms of computer-readable media therefore include for example: a floppy disk, a flexible disk, hard disk, magnetic tape, any other magnetic medium, a CD-ROM, DVD or DVD-ROM, any other optical medium, punch cards paper tape, any other physical storage medium with patterns of holes, a RAM, a ROM, a PROM and EPROM, a FLASH-EPROM, any other memory chip or cartridge, a carrier wave transporting data or instructions, cables or links transporting such a carrier wave, or any other medium from which a computer may read programming code and/or data. Many of these forms of computer readable media may be involved in carrying one or more sequences of one or more instructions to a processor for execution.

The computer system 1201 can include or be in communication with an electronic display 1235 that comprises a user interface (UI) 1240 for providing, for example, signal detection results, optical images, and results of parameter and/or characterization determinations. Examples of UIs include, without limitation, a graphical user interface (GUI) and web-based user interface.

Methods and systems of the present disclosure can be implemented by way of one or more algorithms. An algorithm can be implemented by way of software upon execution by the central processing unit 1205. The algorithm can, for example, process optical signal data and/or perform image processing.

Devices, systems, compositions and methods of the present disclosure may be used for various applications, such as, for example, processing a single analyte (e.g., RNA, DNA, or protein) or multiple analytes (e.g., DNA and RNA, DNA and protein, RNA and protein, or RNA, DNA and protein) from a single cell. For example, a biological particle (e.g., a cell or cell bead) is partitioned in a partition (e.g., droplet), and multiple analytes from the biological particle are processed for subsequent processing. The multiple analytes may be from the single cell. This may enable, for example, simultaneous proteomic, transcriptomic and genomic analysis of the cell.

Example 1. Processing an Optically Tagged Bead

A nucleic acid probe with a fluorescent tag (Alexa Fluor 488) on the 5' end is added with a bead. The nucleic acid probe comprises a sequence complementary to a binding sequence of the bead. The tagged nucleic acid hybridizes to the binding sequence in a selected region of the bead, forming an optically tagged bead. The 3' end of the nucleic acid probe is modified to render the probe substantially unreactive in subsequent chemical reactions. A 3 carbon spacer (C3 spacer) is attached to a 3' end of the probe to have SEQ ID: 5'-Alexa488N/AAGAGCGTCGTGTAG/3SpC3 (SEQ ID NO: 1).

The fluorescent signal emitted from the Alexa Fluor 488 along with the forward and side scatter is detected with a flow cytometer. The detected signals are analyzed to determine the concentration of primers of the bead and the size of the bead, assuming the beads have about the same concentration of the nucleic acid probes. The bead is partitioned and the fluorescent signal is again detected to determine additional parameters including cell occupancy, bead occupancy, and concentration of the reagent in the partition. Alternatively, a fluorescent signal may be determined once after partitioning to determine the abovementioned parameters.

Sample mRNA is co-partitioned with the tagged bead and hybridizes to the priming sequence of the nucleic acid molecule attached to the bead. The mRNA-nucleic acid molecule is subject to further processing, and its derivative is sequenced in further analysis.

Example 2. Quality Control of Optically Tagged Beads

A quality control procedure for gel beads was performed. The procedure generally comprised hybridizing beads with nucleic acid probes and analyzing the hybridized beads to determine the homogeneity and/or bead-to-bead variation of the population of hybridized beads. The beads used for this procedure are described elsewhere herein, e.g., the barcoded bead shown in FIG. 8 which comprises nucleic acid molecules coupled thereto, comprising one or more functional sequences. For an example of other functional sequences that may be attached to beads, see, e.g., U.S. Pat. Nos. 9,951,386; 10,011,872; U.S. Pat. Pub. 20180340171; and U.S. Pat. Pub. 20190249226; the disclosures of which are each incorporated by reference herein in their entireties. The procedure was performed on different types of gel beads, including functionalized gel beads and unfunctionalized gel beads for comparison. The functionalized gel beads contained different functional sequences as described elsewhere herein (e.g., primer/primer binding sequences, such as a sequencing primer/primer binding sequence (such as a R1 or partial R1 sequencing primer binding sequence); capture sequences, such as a poly-T sequence or a TSO sequence). The gel beads were washed to prepare for probe hybridization. The fluorescent nucleic acid probes comprised fluorophores such as FAM, Alexa, or other fluorophores listed elsewhere herein. The fluorescent probes were prepared for probe hybridization to one or more functional sequences on the gel beads by diluting the probes in suitable buffers to predetermined concentrations. In some instances, probes are selected such that each probe specific for a particular sequence on a bead-bound molecule has a different and/or distinguishable fluorophore (e.g., fluorophores with different excitation/emission wavelengths). In this way, multiple sequences on a bead-bound oligonucleotide can be independently verified and interrogated. Once the samples were prepared, the probes and gel beads were mixed and subjected to conditions (e.g., with suitable thermal conditions, agitation, etc.) to hybridize the fluorescent probes to the gel beads. The resulting mixture was subject to one or more post-hybridization washes with a suitable buffer. The washing steps involved adding buffer to the sample comprising the beads in a container, centrifuging the mixture, allowing the beads to settle, removing part or all of the supernatant (e.g., without substantially removing the beads) and repeating where/if suitable, thereby preparing a sample of hybridized gel beads. The hybridized gel beads used in this procedure comprise a fluorescent probe attached to a sequence of the gel bead, such as the hybridized beads shown in FIG. 9 or FIG. 10.

The sample of hybridized beads were further processed and prepared to be analyzed on a flow cytometer (e.g., a Guava EasyCyte HT Instrument). The beads were transferred to suitable containers (e.g., microcentrifuge tubes compatible with the instrument used). Samples containing the hybridized beads were diluted in a proper buffer to pre-determined concentrations and were read on the flow cytometer. The signals detected by the flow cytometer were used to determine bead-to-bead variability in primer loading and/or ligation efficiency. Metrics such as mean, median, standard deviation, coefficient of variance, and other metrics of the signals were calculated and used to determine qualities and/or parameters of the beads, such as bead-to-bead variability.

While preferred embodiments of the present invention have been shown and described herein, it will be obvious to those skilled in the art that such embodiments are provided by way of example only. It is not intended that the invention be limited by the specific examples provided within the specification. While the invention has been described with reference to the aforementioned specification, the descriptions and illustrations of the embodiments herein are not meant to be construed in a limiting sense. Numerous variations, changes, and substitutions will now occur to those skilled in the art without departing from the invention. Furthermore, it shall be understood that all aspects of the invention are not limited to the specific depictions, configurations or relative proportions set forth herein which depend upon a variety of conditions and variables. It should be understood that various alternatives to the embodiments of the invention described herein may be employed in practicing the invention. It is therefore contemplated that the invention shall also cover any such alternatives, modifications, variations or equivalents. It is intended that the following claims define the scope of the invention and that methods and structures within the scope of these claims and their equivalents be covered thereby.

---

---

What is claimed is:

1. A method, comprising:
   (a) hybridizing a bead and a probe to generate an optically-tagged bead, wherein the optically-tagged bead comprises a binding sequence,
   wherein the probe hybridizes to the binding sequence,
   wherein the probe comprises: (i) a fluorescent tag; and (ii) at a 3' end of the probe, a moiety selected from the group consisting of a fluorophore, a carbon spacer, a biotin molecule, an inverted terminal base, a sequence that destabilizes hybridization between the bead and the probe, and an unlocked nucleic acid, and
   wherein the moiety renders the probe hybridized to the bead at least 60% less reactive in a base incorporation reaction as compared to an equivalent nucleic acid probe lacking the moiety; and
   (b) detecting one or more signals indicative of the fluorescent tag from the optically-tagged bead,
   wherein the optically-tagged bead comprises: i) a molecule comprising the binding sequence hybridized to the probe, and ii) a nucleic acid barcode molecule, wherein the molecule is different from the nucleic acid barcode molecule.

2. The method of claim 1, wherein the probe comprises the fluorescent tag at a 5' end of the probe.

3. The method of claim 1, further comprising, prior to (a), subjecting a nucleic acid probe comprising the fluorescent tag to conditions sufficient to modify the nucleic acid probe to yield the probe.

4. The method of claim 3, further comprising adding the moiety to the nucleic acid probe.

5. The method of claim 1, further comprising conducting the base incorporation reaction with or in a presence of the optically-tagged bead.

6. The method of claim 5, wherein the base incorporation reaction is an extension reaction.

7. The method of claim 5, wherein (b) is performed prior to conducting the base incorporation reaction with or in the presence of the optically-tagged bead.

8. The method of claim 5, wherein (b) is performed subsequent to conducting the base incorporation reaction with or in the presence of the optically-tagged bead.

9. The method of claim 1, wherein the optically-tagged bead comprises a gel bead.

10. The method of claim 1, the method further comprises determining a parameter of the optically-tagged bead based on the one or more signals.

11. The method of claim 10, wherein the optically-tagged bead comprises a plurality of primers and wherein the parameter is a concentration of the plurality of primers on the optically-tagged bead, and wherein the probe comprises a probe sequence configured to hybridize to a sequence common to the plurality of primers.

12. The method of claim 10, wherein the parameter is a size of the optically-tagged bead.

13. The method of claim 1, further comprising, subsequent to (a), partitioning the optically-tagged bead into a partition among a plurality of partitions.

14. The method of claim 13, further comprising using the one or more signals to assess a bead occupancy of the partition.

15. The method of claim 13, wherein the partition is a droplet or a well.

16. The method of claim 1, further comprising, subsequent to (a), co-partitioning the optically-tagged bead with an analyte in a partition among a plurality of partitions.

17. The method of claim 1, wherein the carbon spacer comprises a 3 carbon atom spacer, a 6 carbon spacer, a 9 carbon spacer, or an 18 carbon spacer.

\* \* \* \* \*